(12) United States Patent
Sayre et al.

(10) Patent No.: US 10,294,475 B2
(45) Date of Patent: *May 21, 2019

(54) PARATRANSGENIC SYSTEM FOR THE BIOCONTROL OF DISEASE-TRANSMITTING MOSQUITOS

(71) Applicant: Pebble Labs, Inc., Los Alamos, NM (US)

(72) Inventors: Richard Sayre, Los Alamos, NM (US); Jiaannong Xu, Las Cruces, NM (US)

(73) Assignee: PEBBLE LABS, INC., Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,904

(22) Filed: Mar. 15, 2018

(65) Prior Publication Data

US 2018/0216110 A1    Aug. 2, 2018

Related U.S. Application Data

(63) Continuation-in-part of application No. PCT/US2017/052118, filed on Sep. 19, 2017.

(60) Provisional application No. 62/395,791, filed on Sep. 16, 2016.

(51) Int. Cl.
   *C12N 15/113*   (2010.01)
   *A01N 25/00*    (2006.01)
   *A01N 57/16*    (2006.01)
   *A01N 63/00*    (2006.01)
   *A01N 63/02*    (2006.01)

(52) U.S. Cl.
   CPC ........ *C12N 15/1131* (2013.01); *A01N 25/006* (2013.01); *A01N 57/16* (2013.01); *A01N 63/00* (2013.01); *C12N 2310/111* (2013.01); *C12N 2310/14* (2013.01); *C12N 2330/51* (2013.01)

(58) Field of Classification Search
   None
   See application file for complete search history.

(56) References Cited

U.S. PATENT DOCUMENTS

| 8,933,042 B2 | 1/2015 | Raemaekers et al. |
| 2011/0182859 A1* | 7/2011 | Hyde ...................... A61K 35/74 424/93.2 |

FOREIGN PATENT DOCUMENTS

| GB | 1415502.2 | 11/2014 |
| WO | 2013117910 A1 | 8/2013 |

OTHER PUBLICATIONS

Wilke and Marrelli, Paratransgenesis: a promising new strategy for mosquito vector control, Parasites & Vectors (2015) 8:342, pp. 1-9.*
Franz et al, Engineering RNA interference-based resistance to dengue virus type 2 in genetically modified Aedes aegypti, PNAS, 2006, pp. 4198-4203.*
Munjal et al, Advances in Developing THerapies to Combat Zlka Virus: Current Knowledge and Future Perspective, Frontiers in Microbioolgy, 2017, pp. 1-19.*
Kim et al, A Transformed Bacterium Expressing Double-Stranded RNA Specific to Integrin β1 Enhances Bt Toxin Efficacy against a Polyphagous Insect Pest, Spodoptera exigua, PLOS one, 2015, pp. 1-15.*
Klausen, et al., "Biofilm formation by Pseudomonas aeruginosa wild type, flagella and type IV pili mutants", Molecular Microbiology, Feb. 18, 2003, pp. 1511-1524, vol. 48, No. 6, Blackwell Publishing, Ltd.
Puglise, et al., "Expression Profiles and RNAi Silencing of Inhibitor of Apoptosis Transcripts in Aedes, Anopheles, and Culex Mosquitoes (Diptera: Culicidae)", Journal of Medical Entomology, Dec. 11, 2015, pp. 304-314, vol. 53, No. 2, Oxford University Press on behalf of Entomological Society of America.
Zhang, et al., "Chitosan/Interfering RNA Nanoparticle Mediated Gene Silencing in Disease Vector Mosquito Larvae", Journal of Visualized Experiments, Mar. 25, 2015, pp. 1-11, vol. 97, Journal of Visualized Experiments.
Rani, et al., "Bacterial diversity analysis of larvae and adult midgut microflora using culture-dependent and culture-independent methods in lab-reared and field-collected Anopheles stephensi—an Asian malarial vector", BioMed Central Microbiology, May 19, 2009, pp. 1-22, vol. 9, http://www.biomedcentral.com/1471-2180/9/96.
Wang, et al., "Dynamic Gut Microbiome across Life History of the Malaria Mosquito Anopheles gambiae in Kenya", PLoS ONE, Sep. 21, 2011, pp. 1-9, vol. 6, Issue 9, PLoS ONE.
Kumar, et al., "Development of an RNAi based microalgal larvicide to control mosquitoes", MalariaWorld Journal, Mar. 2013, pp. 1-7, vol. 4, No. 6, (GCE special issue).
Jose, "Movement of Regulatory RNA Between Animal Cells", Genesis, Jun. 29, 2015, pp. 395-416, vol. 53, Wiley Periodicals, Inc.
Faye, et al., "Molecular Evolution of Zika Virus during Its Emergence in the 20th Century", PLOS Neglected Tropical Diseases, Jan. 9, 2014, pp. 1-10, vol. 8, Issue 1.

(Continued)

*Primary Examiner* — Maria Marvich
(74) *Attorney, Agent, or Firm* — Berg Hill Greenleaf Ruscitti LLP.

(57) ABSTRACT

The inventive technology relates to novel paratransgenic strategies for the control of pathogens. The inventive technology may specifically include a novel paratransgenic system configured to deliver one or more inhibitory RNA molecules to pathogen/disease-transmitting organisms. In a preferred embodiment, the invention may include one or more genetically engineered enteric bacteria configured to deliver one or more interfering RNA molecules to pathogen/disease-transmitting mosquitos.

14 Claims, 26 Drawing Sheets

Specification includes a Sequence Listing.

(56) References Cited

OTHER PUBLICATIONS

Pei, et al., "The waaL gene mutation compromised the inhabitation of *Enterobacter* sp. Ag1 in the mosquito gut environment", Parasites & Vectors, 2015, pp. 1-10, vol. 8, Biology Department, New Mexico State University.

Mukherjee, et al., "RNA interference modulates replication of dengue virus in *Drosophila melanogaster* cells", BMC Microbiology, 2010, pp. 1-14, vol. 10, Molecular Biology Program, New Mexico State University.

Hanley, et al., "Superior infectivity for mosquito vectors contributes to competitive displacement among strains of dengue virus", BioMed Central, Feb. 13, 2008, pp. 1-10, vol. 8, No. 1, http://www.biomedcentral.com/1472-6785/8/1.

Scott, et al., "Towards the elements of successful insect RNAi", Journal Insect Physiology, Dec. 1, 2013, pp. 1-22, vol. 29, No. 12, Elsevier Ltd.

Hegde, et al., "The microbiome modulates arbovirus transmission in mosquitoes", Current Opinion in Virology, Sep. 11, 2015, pp. 97-102, vol. 15, Elsevier, B.V.

Foy, et al., "Development of a new Sindbis virus transducing system and its characterization in three Culicine mosquitoes and two *Lepidopteran* species", Insect Molecular Biology, 2004, pp. 89-100, vol. 13, No. 1, The Royal Entomological Society.

Ramakrishnan, et al., "Determination of 50% endpoint titer using a simple formula", World Journal of Virology, May 12, 2016, pp. 85-86, vol. 5, Issue 2, Baishideng Publishing Group, Inc.

Olson, et al., "Arbovirus-mosquito interactions: RNAi pathway", Current Opinion in Virology, 2015, pp. 119-126, vol. 15, Elsevier, B.V.

Franz, et al., "Engineering RNA interference-based resistance to dengue virus type 2 in genetically modified Aedes aegypti", PNAS, Mar. 14, 2006, pp. 4198-4203, vol. 103, No. 11, The National Academy of Sciences of the USA.

Sánchez-Vargas, et al., "Dengue Virus Type 2 Infections of Aedes aegypti Are Modulated by the Mosquito's RNA Interference Pathway", PLoS Pathogens, Feb. 13, 2009, pp. 1-11, vol. 5, Issue 2.

Timmons, et al., "Ingestion of bacterially expressed dsRNAs can produce specific and potent genetic interference in Caenorhabditis elegans", Gene: An International Journal on Genes and Genomes, 2001, pp. 103-112, vol. 263, Elsevier Science B.V.

Pande, et al., "Metabolic cross-feeding via intercellular nanotubes among bacteria", Nature Communications, Feb. 23, 2015, pp. 1-13, Macmillan Publishers Limited.

Takiff, et al., "Genetic Analysis of the Inc Operon of *Escherichia coli*", Journal of Bacteriology, May 1989, pp. 2581-2590, vol. 171, No. 5, American Society for Microbiology.

Derouiche, et al., "Protein Complex within *Escherichia coli* Inner Membrane: TolA N-Terminal Domain Interacts with TolQ and TolR Proteins", The Journal of Biological Chemistry, May 12, 1995, pp. 11078-11084, vol. 270, No. 19, Issue of May 12, The American Society for Biochemistry and Molecular Biology, Inc., Printed in the U.S.A.

Song, et al., "A new Vibrio cholerae sRNA modulates colonization and affects release of outer membrane vesicles", Molecular Microbiology, Aug. 15, 2008, pp. 100-111, vol. 70, Issue 1, Blackwell Publishing Ltd.

Shih, et al., "The SID-1 double-stranded RNA transporter is not selective for dsRNA length", RNA, 2009, retrieved online on Dec. 17, 2017, pp. 384-390, vol. 15, Cold Spring Harbor Laboratory Press, rnajournal.cshlp.org.

McEwan, et al., "Uptake of Extracellular Double-Stranded RNA by SID-2", Molecular Cell, Sep. 14, 2012, pp. 146-754, vol. 47, Elsevier Inc.

Campbell, et al., "Comparative genomics of small RNA regulatory pathway components in vector mosquitoes", BMC Genomics, Sep. 18, 2008, pp. 1-16, vol. 9, Issue 425.

Kim, et al., "YmdB: a stress-responsive ribonuclease-binding regulator of *E. coli* RNase III activity", Genes & Development, Oct. 16, 2008, pp. 3497-3508, vol. 22, Cold Spring Harbor Laboratory Press.

Ren, et al., "Staufen Negatively Modulates MicroRNA Activity in Caenorhabditis elegans", G3: Genes, Genomes, Genetics, May 2016, pp. 1227-1237, vol. 6, Genetics Society of America.

Raman, et al., "The double-stranded RNA binding protein RDE-4 can act cell autonomously during feeding RNAi in C. elegans", Nucleic Acids Research, May 24, 2017, pp. 8463-8473, vol. 45, No. 14, Oxford University Press on behalf of Nucleic Acids Research.

Zhang, et al., "Functional Replacement of the Hemolysin A Transport Signal by a Different Primary Sequence", PNAS, May 1, 1993, pp. 4211-4215, vol. 90, No. 9, National Academy of Sciences.

Natale, et al., "Sec- and Tat-mediated protein secretion across the bacterial cytoplasmic membrane—Distinct translocases and mechanisms", Biochimica et Biophysica Acta, 2008, pp. 1735-1756, vol. 1778, Elsevier.

Jones, et al., "Characterisation of cell-penetrating peptide-mediated peptide delivery", British Journal of Pharmacology, 2005, pp. 1093-1102, vol. 145, Nature Publishing Group.

Provost, et al., "Ribonuclease activity and RNA binding of recombinant human Dicer", The EMBO Journal, 2002, pp. 5864-5874, vol. 21, No. 21, European Molecular Biology Organization.

Hammond, et al., "Argonaute2, a Link Between Genetic and Biochemical Analyses of RNAi", Science, Aug. 10, 2001, pp. 1146-1150, The American Association for the Advancement of Science.

Scott, et al., "Comparison of Dengue Virus Type 2-Specific Small RNAs from RNA Interference-Competent and -Incompetent Mosquito Cells", PLoS Neglected Tropical Diseases, Oct. 26, 2010, pp. 1-13, vol. 4, Issue 10.

Hess, et al., "Small RNA profiling of Dengue virus-mosquito interactions implicates the PIWI RNA pathway in anti-viral defense", BioMed Central, 2011, pp. 1-12, vol. 11, No. 45.

Campbell, et al., "Aedes aegypti uses RNA interference in defense against Sindbis virus infection", BMC Microbiology, Mar. 17, 2008, pp. 1-12, vol. 8, No. 47, BioMed Central Ltd.

Bettencourt, et al., "Hemolin gene silencing by ds-RNA injected into Cecropia pupae is lethal to next generation embryos", Insect Molecular Biology, Feb. 14, 2002, pp. 267-271, vol. 11, No. 3, Royal Entomological Society.

Amdam, et al., "Disruption of vitellogenin gene function in adult honeybees by intra-abdominal injection of double-stranded RNA", BioMed Central Biotechnology, Jan. 20, 2003, pp. 1-8, BioMed Central Ltd.

Tomoyasu, et al., "Larval RNAi in Tribolium (Coleoptera) for analyzing adult development", Dev. Genes Evol., Sep. 9, 2004, pp. 575-578, vol. 214, Springer-Verlag.

Singh, et al., "Oral Delivery of Double-Stranded RNA in Larvae of the Yellow Fever Mosquito, Aedes aegypti: Implications for Pest Mosquito Control", Journal of Insect Science, 2013, pp. 1-18, vol. 13, Article 69, Entomological Society of America.

Turner, et al., "RNA interference in the light brown apple moth, *Epiphyas postvittana* (Walker) induced by double-stranded RNA feeding", Insect Molecular Biology, 2006, pp. 383-391, vol. 15, Issue 3, The Royal Entomological Society.

Wang, et al., "Genome Mining Demonstrates the Widespread Occurrence of Gene Clusters Encoding Bacteriocins in Cyanobacteria", PLoS One, Jul. 20, 2011, pp. 1-10, vol. 6, Issue 7.

Katoch, et al., "RNAi for Insect Control: Current Perspective and Future Challenges", Appl. Biochem. Biotechnol., Aug. 1, 2013, pp. 847-873, vol. 171, Springer Science + Business Media, New York.

Bonizzoni, et al., "Complex Modulation of the Aedes aegypti Transcriptome in Response to Dengue Virus Infection", PLoS One, Nov. 27, 2012, pp. 1-14, vol. 7, Issue 11.

Wilke, et al., "Paratransgenesis: a promising new strategy for mosquito vector control", Parasites & Vectors, 2015, pp. 1-9, vol. 8, No. 342.

Favia, et al., "Bacteria of the genus *Asaia stably* associate with *Anopheles stephensi*, an Asian malarial mosquito vector", PNAS, May 22, 2007, pp. 9047-9051, vol. 104, No. 21, The National Academy of Sciences of the USA.

(56) References Cited

OTHER PUBLICATIONS

Yoshida, et al., "Bacteria expressing single-chain immunotoxin inhibit malaria parasite development in mosquitoes", Molecular & Biochemical Parasitology, 2001, pp. 89-96, vol. 113, Elsevier Science B.V.

Coutinho-Abreu, et al., "Transgenesis and paratransgenesis to control insect-borne diseases: Current status and future challenges", Parasitol Int., Mar. 2010, pp. 1-19, vol. 59, Issue 1, Elsevier Ireland LTD.

Gonzalez-Ceron, et al., "Bacteria in Midguts of Field-Collected Anopheles albimanus Block Plasmodium vivax Sporogonic Development", Journal of Medical Entomology, 2003, pp. 371-374, vol. 40, Issue 3, Entomological Society of America.

Lindh, et al., "16S rRNA Gene-Based Identification of Midgut Bacteria from Field-Caught Anopheles gambiae Sensu Lato and A. funestus Mosquitoes Reveals New Species Related to Known Insect Symbionts", Applied and nvironmental Microbiology, Nov. 2005, pp. 7217-7223, vol. 71, No. 11, American Society for Microbiology.

Damiani, et al., "Paternal transmission of symbiotic bacteria in malaria vectors", Current Biology, 2008, pp. R1087-R1088, vol. 18, No. 23.

Terenius, et al., "16S rRNA Gene Sequences from Bacteria Associated with Adult Anopheles darlingi (Diptera: Culicidae) Mosquitoes", Journal of Medical Entomology, 2008, pp. 172-175, vol. 45, Issue 1, Entomological Society of America.

Rani, et al., "Bacterial diversity annalysis of larvae and adult midgut microflora using culture-dependent and culture-independent methods in lab-reared and field-collected Anopheles stephensi—an Asian malarial vector", BioMed Central Microbiology, May 19, 2009, pp. 1-22, vol. 9, No. 96, BioMed Central Ltd.

Hillesland, et al., "Identification of Aerobic Gut Bacteria from the Kala Azar Vector, Phlebotomus argentipes: A Platform for Potential Paratransgenic Manipulation of Sand Flies", American Journal of Tropical Medicine and Hygiene, 2008, pp. 881-886, vol. 79, Issue 6, The American Society of Tropical Medicine and Hygiene.

Gaio, et al., "Contribution of midgut bacteria to blood digestion and egg production in aedes aegypti (diptera: *Culicidae*) (L.)", Parasites & Vectors, 2011, pp. 1-10, vol. 4, No. 105, BioMed Central Ltd.

Sayler, et al., "Field applications of genetically engineered microorganisms for bioremediation processes", Current Opinion in Biotechnology, 2000, pp. 286-289, vol. 11, Elsevier Science Ltd.

Briones, et al., "Thorsellia anophelis is the dominant bacterium in a Kenyan population of adult Anopheles gambiae mosquitoes", The ISME Journal, 2008, pp. 74-82, vol. 2, International Society for Microbial Ecology.

Wang, et al., "Fighting malaria with engineered symbiotic bacteria from vector mosquitoes", PNAS Early Edition, Jun. 7, 2012, pp. 1-6.

GenBank: KU321639.1, Zika virus strain ZikaSPH2015, complete genome, Nucleotide-NCBI, accessed online on Mar. 15, 2018, https://www.ncbi.nlm.nih.gov/nuccore/KU321639, pp. 1-5.

Witten, et al., "Gene silencing in non-model insects: Overcoming hurdles using symbiotic bacteria for trauma-free sustainable delivery of RNA interference", Bioessays, www.bioessays-journal.com, 2017, pp. 1-12, vol. 39, No. 3, Wiley Periodicals, Inc.

\* cited by examiner

| Strain Name | Biotyper ID | 16S 1st match | 16S 2nd match | Plasmid used to label |
|---|---|---|---|---|
| AE001 | Enterobacter cloacae | Enterobacter tabaci strain YIM Hb-3 | Pantoea agglomerans strain JCM1236 | mini Tn7 eYFP |
| AE008 | Enterobacter cloacae | Enterobacter tabaci strain YIM Hb-3 | Pantoea agglomerans strain JCM1236 | mini Tn7 eYFP |
| AE053 | Enterobacter kobei | Enterobacter tabaci strain YIM Hb-3 | Pantoea agglomerans strain JCM1236 | mini Tn7 eYFP |
| AE058 | Enterobacter kobei | Enterobacter tabaci strain YIM Hb-3 | Pantoea agglomerans strain JCM1236 | mini Tn7 eYFP |
| AE073 | Enterobacter kobei | Enterobacter tabaci strain YIM Hb-1 | Pantoea agglomerans strain JCM1236 | mini Tn7 eYFP |
| AE077 | Enterobacter cloacae | Enterobacter tabaci strain YIM Hb-3 | Pantoea agglomerans strain JCM1236 | mini Tn7 eYFP |
| AE090 | Enterobacter cloacae | Enterobacter tabaci strain YIM Hb-3 | Pantoea agglomerans strain JCM1236 | mini Tn7 eYFP |
| AE138 | Enterobacter kobei | Enterobacter tabaci strain YIM Hb-3 | Pantoea agglomerans strain JCM1236 | mini Tn7 eYFP |
| AE157 | Enterobacter kobei | Enterobacter tabaci strain YIM Hb-3 | Pantoea agglomerans strain JCM1236 | mini Tn7 eYFP |
| AE163 | Enterobacter kobei | Enterobacter tabaci strain YIM Hb-3 | Pantoea agglomerans strain JCM1236 | mini Tn7 eYFP |
| AE005 | Pseudomonas mosselii/putida | Pseudomonas mosselii strain CFML 90-83 | Pseudomonas entomophila strain L48 | mini Tn7 eYFP |
| AE062 | Pseudomonas mosselii/putida | Pseudomonas mosselii strain CFML 90-83 | Pseudomonas entomophila strain L48 | mini Tn7 eYFP |
| AE074 | Pseudomonas mosselii/putida | Pseudomonas mosselii strain CFML 90-83 | Pseudomonas entomophila strain L48 | mini Tn7 eYFP |
| AE076 | Pseudomonas putida group | Pseudomonas plecoglossicida strain NBRC 103162 | Pseudomonas taiwanensis strain BCRC 17751 | mini Tn7 eYFP |
| AE078 | Pseudomonas mosselii/putida | Pseudomonas mosselii strain CFML 90-83 | Pseudomonas entomophila strain L48 | mini Tn7 eYFP |
| AE099 | Pseudomonas mosselii/putida | Pseudomonas mosselii strain CFML 90-83 | Pseudomonas entomophila strain L48 | mini Tn7 eYFP |
| AE109 | Pseudomonas mosselii/putida | Pseudomonas mosselii strain CFML 90-83 | Pseudomonas entomophila strain L48 | mini Tn7 eYFP |
| AE139 | Pseudomonas mosselii/putida | Pseudomonas mosselii strain CFML 90-83 | Pseudomonas entomophila strain L48 | mini Tn7 eYFP |
| AE140 | Pseudomonas mosselii/putida | Pseudomonas mosselii strain CFML 90-83 | Pseudomonas entomophila strain L48 | mini Tn7 eYFP |
| AE143 | Pseudomonas putida group | Pseudomonas plecoglossicida strain NBRC 103162 | Pseudomonas taiwanensis strain BCRC 17751 | mini Tn7 eYFP |
| AE171 | Pseudomonas putida group | Pseudomonas plecoglossicida strain NBRC 103162 | Pseudomonas taiwanensis strain BCRC 17751 | mini Tn7 eYFP |
| AE180 | Pseudomonas putida group | Pseudomonas plecoglossicida strain NBRC 103162 | Pseudomonas taiwanensis strain BCRC 17751 | mini Tn7 eYFP |

FIGURE 2

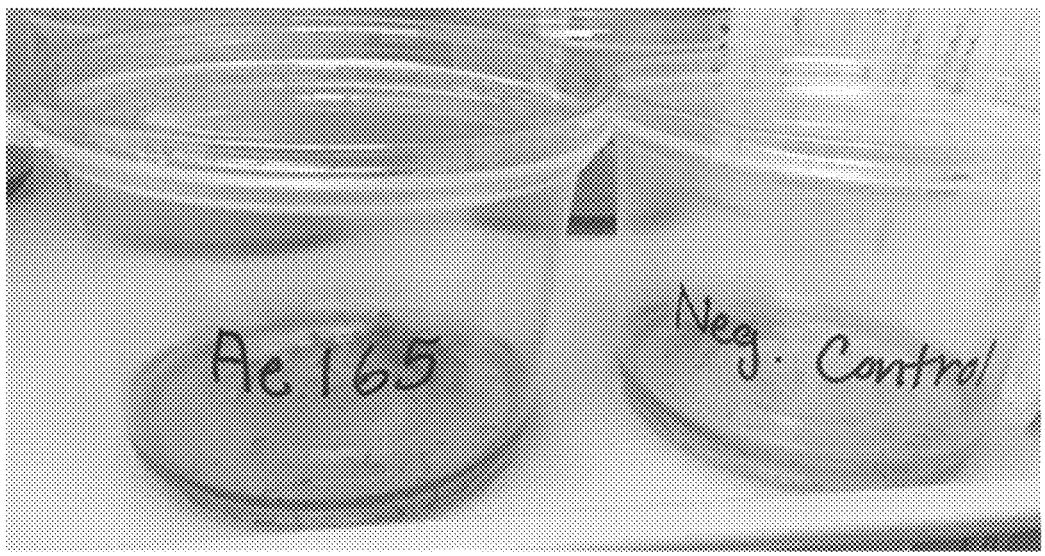
FIGURE 5

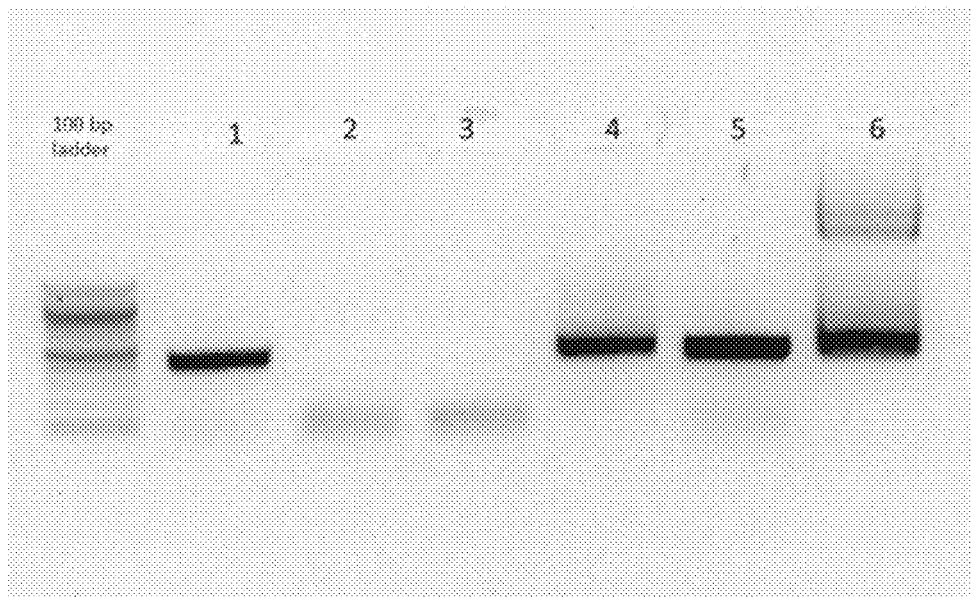

1 – PCR product from reverse transcribed filtrate of HT115 T7-dsGFP bacteria
2 – PCR product from reverse transcribed filtrate from HT115 puc19-DL (non-target, - control)
3 – Lack of PCR product from reverse transcribed filtrate from HT115, no plasmid (- control)
4 – PCR product from H115-dsGFP plasmid (+ control)
5 – PCR product from reverse transcribed filtrate of HT115 T7-dsGFP
6 – PCR product using isolated T7-dsGFP plasmid as a template (+ control)

FIGURE 8

| dsRNA | 4 dpi % Positive | | | | 5 dpi % Positive | | | |
|---|---|---|---|---|---|---|---|---|
| Flour-escence level | ++ | Weak | - | Sample number | ++ | Weak | - | Sample number |
| βGal | 44 | 11 | 44 | 9 | 63 | - | 37 | 8 |
| eGFP | 0 | 12 | 88 | 8 | 8 | 36 | 56 | 25 |

Dpi is days post infection. Average # bacteria expressing dsRNA/insect = 655

| ZIKV strain | Injection group | ZIKV infection date | Days post-infection | Number of mosquitoes analyzed | Number of mosquitoes infected | % Infection | Mean titer |
|---|---|---|---|---|---|---|---|
| PRABC59 (Puerto Rico) | PBS | 12/8/17 | 7 | 16 | 16 | 100 | 7.44E+04 |
| | | | 14 | 16 | 16 | 100 | 4.78E+05 |
| | Non-injected | | 7 | 15 | 13 | 86.7 | 5.13E+04 |
| | | | 14 | 16 | 14 | 87.5 | 4.27E+05 |
| | dsBgal | | 7 | 16 | 15 | 93.8 | 1.68E+04 |
| | | | 14 | 16 | 15 | 93.8 | 2.09E+05 |
| | dsZIKV#1 | | 7 | 16 | 1 | 6.3 | 5.46E+00 |
| | | | 14 | 16 | 5 | 31.3 | 3.88E+03 |
| | dsZIKV#2 | | 7 | 16 | 4 | 25 | 4.48E+03 |
| | | | 14 | 16 | 4 | 25 | 5.41E+03 |
| | dsZIKV#3 | | 7 | 16 | 2 | 12.5 | 4.23E+04 |
| | | | 14 | 15 | 3 | 20 | 1.19E+03 |
| | dsZIKV#4 | | 7 | 16 | 5 | 31.3 | 4.53E+03 |
| | | | 14 | 16 | 2 | 12.5 | 4.37E+03 |
| | dsZIKV#5 | | 7 | 16 | 0 | 0 | 0.00E+00 |
| | | | 14 | 16 | 1 | 6.3 | 4.19E-01 |
| 41525 (West Africa) | PBS | | 7 | 11 | 11 | 100 | 2.63E+06 |
| | | | 14 | 15 | 15 | 100 | 2.53E+06 |
| | Non-injected | | 7 | 11 | 11 | 100 | 2.65E+06 |
| | | | 14 | 15 | 14 | 93.4 | 3.28E+06 |
| | dsBgal | | 7 | 11 | 11 | 100 | 4.01E+06 |
| | | | 14 | 14 | 14 | 100 | 1.98E+06 |
| | dsZIKV#1 | | 7 | 15 | 1 | 6.7 | 3.56E+04 |
| | | | 14 | 15 | 6 | 40 | 2.13E+05 |
| | dsZIKV#2 | | 7 | 10 | 9 | 90 | 3.42E+05 |
| | | | 14 | 15 | 11 | 73.4 | 3.25E+05 |
| | dsZIKV#3 | | 7 | 9 | 5 | 55.6 | 1.57E+05 |
| | | | 14 | 15 | 1 | 6.7 | 7.11E+04 |
| | dsZIKV#4 | | 7 | 10 | 6 | 60 | 1.01E+05 |
| | | | 14 | 15 | 4 | 26.7 | 4.72E+04 |
| | dsZIKV#5 | | 7 | 9 | 5 | 55.6 | 5.56E+04 |
| | | | 14 | 15 | 7 | 46.7 | 9.65E+04 |
| MR677 (East Africa) | PBS | | 7 | 16 | 15 | 93.8 | 9.28E+05 |
| | | | 14 | 16 | 16 | 100 | 6.53E+06 |
| | Non-injected | | 7 | 16 | 15 | 93.8 | 2.42E+06 |
| | | | 14 | 16 | 16 | 100 | 6.62E+06 |
| | dsBgal | | 7 | 16 | 16 | 100 | 2.00E+06 |
| | | | 14 | 16 | 16 | 100 | 4.86E+06 |
| | dsZIKV#1 | | 7 | 16 | 2 | 12.5 | 5.32E+03 |
| | | | 14 | 16 | 3 | 18.8 | 6.62E+05 |
| | dsZIKV#2 | | 7 | 16 | 8 | 50 | 4.39E+05 |
| | | | 14 | 16 | 10 | 62.5 | 2.10E+06 |
| | dsZIKV#3 | | 7 | 16 | 9 | 56.3 | 3.17E+03 |
| | | | 14 | 15 | 6 | 40 | 1.60E+05 |
| | dsZIKV#4 | | 7 | 16 | 6 | 37.5 | 4.02E+04 |
| | | | 14 | 16 | 7 | 43.8 | 3.52E+05 |
| | dsZIKV#5 | | 7 | 16 | 2 | 12.5 | 4.40E+03 |
| | | | 14 | 16 | 6 | 37.5 | 2.53E+05 |

FIGURE 17

PARATRANSGENIC SYSTEM FOR THE BIOCONTROL OF DISEASE-TRANSMITTING MOSQUITOS

This U.S. Nonprovisional Application is a bypass continuation-in-part which claims the benefit of and priority to International Application No. PCT/US17/52118, filed Sep. 19, 2017, which claims the benefit of and priority to U.S. Provisional Application No. 62/395,791, filed Sep. 16, 2016. The entire specification and figures of the above-referenced applications are hereby incorporated in their entirety by reference.

SEQUENCE LISTING

The instant application contains a Sequence Listing which has been submitted electronically in ASCII format and is hereby incorporated by reference in its entirety. Said ASCII copy, created on Mar. 15, 2018, is named MosquitoCIP-PCT.txt and is 18 Kbytes in size.

TECHNICAL FIELD

Generally, the inventive technology relates to novel paratransgenic strategies for the control of mosquito-borne diseases. Specifically, the invention may comprise novel techniques, systems, and methods for the biocontrol of disease-transmitting mosquitos and/or mosquito larvae.

BACKGROUND OF THE INVENTION

Regulating gene expression either by increasing expression or decreasing expression is considered beneficial for treatment of human diseases. This is especially important in those diseases in which master regulatory genes have been identified. While a majority of efforts have been extended toward enhancing gene expression, down-regulating specific gene expression is equally important. A naturally occurring gene-silencing mechanism triggered by double-stranded RNA (dsRNA), designated as small interfering RNA (siRNA), has emerged as a very important tool to suppress or knock down gene expression in many systems. RNA interference is triggered by dsRNA that is cleaved by an RNase-III-like enzyme, Dicer, into 21-25 nucleotide fragments with characteristic 5' and 3' termini. These siRNAs act as guides for a multiprotein complex, including a PAZ/PIWI domain containing the protein Argonaute2, that cleaves the target mRNA. These gene-silencing mechanisms are highly specific and potent and can potentially induce inhibition of gene expression throughout an organism.

The last two decades have also seen tremendous progress in gene expression technology, including the continued development of both non-viral and viral vectors. The non-viral approach to gene expression involves the use of plasmid DNAs (pDNAs), which have a number of advantages, including ease of use and preparation, stability and heat resistance, and unlimited size. The plasmids do not replicate in mammalian hosts and do not integrate into host genomes, yet they can persist in host cells and express the cloned gene for a period of weeks to months.

One area that has seen renewed interest in the use of inhibitory RNA molecules is infectious diseases, and in particular mosquito-borne infectious diseases. For example, over 500 arthropod-borne viruses (arboviruses) have been identified, among which approximately 100 are harmful to humans. Such diseases, typically spread by mosquitos, impact nearly half the world's population, account for over 1 million deaths per year, and result in substantial economic losses associated with disease burden. Importantly, the US is facing increasing threats from existing and emerging mosquito-transmitted diseases, e.g. Zika virus, due to accelerated global travel, global warming, and expansion of mosquito habitat. Furthermore, for many mosquito-borne diseases, including malaria, dengue, and Zika, there are currently no vaccines. For these diseases, mosquito control remains the best option for limiting disease spread.

Traditional methods for controlling mosquito or other disease vector populations include the use of pesticides and vector control methods. Existing traditional insecticidal control methods rely upon field technicians, who may fail to find and treat many breeding sites, which can be numerous, and oftentimes inaccessible. Additional methods consist of area-wide treatment via airplane or wind-assisted dispersal from truck-mounted foggers. Unfortunately, the latter fail to treat many breeding sites and are complicated by variable environmental conditions. Additionally, surveys of natural and artificial water containers demonstrate mosquitoes and other arthropods to be highly efficient in finding, inhabiting and laying eggs in variously sized, cryptic water pools, including tree holes and gutters high above ground level. As a result, these traditional methods are inadequate to effectively control disease-carrying mosquito populations and ultimately prevent the pathogens they carry from being transmitted to human hosts.

In one specific example, the majority of vector-control strategies in the last century were based on chemical agents such as dichloro-diphenyl-trichloroethane (DDT). Although insecticides have been successfully used to control mosquitoes of the genera *Aedes* and *Anopheles*, current ecological and environmental protection standards do not allow such approaches because of the adverse effects of many insecticides on non-target species, including humans, their environmental impact, the contamination of soil and water, and the development of selective processes and subsequent mosquito resistance to insecticides. New strategies therefore had to be created to replace the use of insecticides.

In particular, the great reproductive capacity and high genomic flexibility of mosquitoes make management of these insects very difficult. Their high genomic flexibility is demonstrated by the resistance of mosquito populations to chemical and biological insecticides as well as by their ability to adapt to different environmental conditions and to climate changes. Therefore, effective alternative forms of control that can be used on a large scale and are environmentally friendly are urgently needed.

As noted above, mosquitos, acting as carriers of human pathogens, are particularly difficult to control. A typical process of vector infection begins when the pathogen enters the mosquito within a blood meal containing sufficient numbers of the pathogen to ensure some will encounter the epithelium, where the blood has been deposited in the arthropod's midgut. The pathogen must be able to cross the epithelium that has been termed the midgut infection barrier (MIB). Once in the epithelium the pathogen must replicate, cross the epithelium and escape the midgut into the hemocoel in a process termed the midgut escape barrier (MEB). The pathogen then must replicate in various mosquito tissues, but ultimately some sufficient quantity of the pathogen must invade the mosquito's salivary glands in a process overcoming the salivary gland infection barrier (SIB). There the pathogen replicates and ultimately must escape the salivary gland in the process described as the salivary gland escape barrier (SEB) upon subsequent blood feeding when it is injected into a susceptible animal host to complete the transmission cycle. This entire process can take several days to complete in the mosquito during a period called the extrinsic incubation period (EIP). Along the way, there are other arthropod related factors including various barriers to the pathogen that may also influence the pathogen and the arthropod's vector competence. The pathogen encounters arthropod digestive enzymes and digestive processes, intracellular processes, and the arthropod's immune system.

Horizontal arbovirus infection of the vector may be established upon blood-feeding of a susceptible female mosquito on a viremic vertebrate host. Within the insect vector, arboviruses have a complex life cycle that includes replication in the midgut, followed by systemic dissemination via the hemolymph and replication in the salivary glands. Transmission of an arbovirus to a naive vertebrate host during blood-feeding requires high viral titers in the saliva. Anatomical and immunological barriers affect the ability of the virus to reach such titers and thus to accomplish successful transmission to a native host. Despite efficient replication, arboviruses do not cause pathology, suggesting that the insect immune system restricts virus infection to non-pathogenic levels. Innate immunity provides the first line of defense against microbial invaders and is defined by its rapid activation following pathogen recognition by germline-encoded receptors. These receptors recognize small molecular motifs that are conserved among classes of microbes, but are absent from the host, such as bacterial cell wall components and viral double-stranded (ds) RNA. Collectively, these motifs are called pathogen-associated molecular patterns (PAMP).

For example, RNAi is one of the molecular mechanisms for regulation of gene expression generally known as RNA silencing. It has a central role in insect antiviral immunity. Notably, the RNAi response, mechanism or pathway, inhibits virus replication without causing death of the infected cell. For example, it has been shown that RNAi can eliminate Dengue virus (DENV2) from transgenic mosquitoes expressing inverted-repeat RNA to trigger the RNAi pathway against the virus. However, arboviruses are able to persistently infect vectors despite being targeted by the RNAi machinery, as shown by the presence of 21 nt virus-derived small interfering RNAs (viRNAs) in arbovirus-infected, transmission-competent mosquito vectors (Scott et al. (2010) *PLOS Negl Trop Dis* 4: e848; Hess et al. (2011) *BMC Microbiol* 11: 45).

Notably, a number of insect pathogenic viruses express a virus-encoded protein suppressor of RNAi (VSR) during replication. Expression of VSRs in insect virus-infected cells results in enhanced virus production, but in most cases these are virulence factors that greatly increase the pathogenicity of the viral infection. For example, temporally induced silencing of the RNAi machinery in *Ae. aegypti* led to significantly increased SINV (sindbis virus) and DENV2 (Dengue virus) titres combined with increased midgut infection and dissemination rates and a shortened extrinsic incubation period (Campbell et al. (2008) BMC Microbiol 8: 47; Sanchez-Vargas el al. (2009) *PLOS Pathog* 5: e1000299; Khoo et al. (2010) *BMC Microbiol* 10: 130). In studies involving insects, administration (e.g. by direct injections) of in vitro-synthesized dsRNA into virtually any developmental stage can produce loss-of-function mutants (Bettencourt et al. (2002) *Insect Molecular Biology* 11:267-271; Amdam et al. (2003) *BMC Biotechnology* 3: 1; Tomoyasu and Denell (2004) *Development Genes and Evolution* 214: 575-578; Singh et al. (2013) *J Insect Sci.* 13: 69).

Studies on feeding dsRNA revealed effective gene knockdown effects in many insects, including insects of the orders Hemiptera, Coleoptera, and Lepidoptera. Feeding dsRNA to *E. postvittana* larvae has been shown to inhibit the expression of the carboxylesterase gene EposCXE1 in the larval midgut and also inhibit the expression of the pheromone-binding protein EposPBP1 in adult antennae (Turner et al. (2006) *Insect Molecular Biology* 15: 383-391). The feeding of dsRNA also inhibited the expression of the nitrophorin 2 (NP2) gene in the salivary gland of *R. prolixus*, leading to a shortened coagulation time of plasma (Araujo et al. (2006) *Insect Biochemistry and Molecular Biology* 36: 683-693).

Similarly, direct spray of dsRNA on newly hatched *Ostrinia* furnalalis larvae has been reported (Wang et al. (2011) *PloS One* 6: e18644). The studies have shown that after spraying dsRNAs (50 ng/pL) of the DS10 and DS28 genes (i.e. chymotrypsin-like serine protease C3 (DS10) and an unknown protein (DS28), respectively) on the newly hatched larvae placed on the filter paper, the larval mortalities were around 40-50%, whereas, after dsRNAs of ten genes were sprayed on the larvae along with artificial diet, the mortalities were significantly higher to the extent of 73-100%. It was proposed through these results that in a lepidopteron insect, dsRNAs are able to penetrate the integument and could retread larval developmental, ultimately leading to death (Katoch (2013) *Appl Biochem Biotechnol.*, 171(4): 847-73).

In mosquitoes, RNAi method using chitosan/dsRNA self-assembled nanoparticles to mediate gene silencing through larval feeding in the African malaria mosquito (*Anopheles gambiae*) was shown (Zhang et al. (2010) *Insect Molecular Biology* (2010) 19(5): 683-693). Oral-delivery of dsRNAs to larvae of the yellow fever mosquito, *Ae. aegypti* was also shown to be insecticidal. It was found that a relatively brief soaking in dsRNA, without the use of transfection reagents or dsRNA carriers, was sufficient to induce RNAi, and can either stunt growth or kill mosquito larvae (Singh et al. (2013), supra). Furthermore, dsRNA targeting RNAi pathway genes were described to increase Dengue virus (DENV) replication in the *Ae. Aegypti* mosquito and to decrease the extrinsic incubation period required for virus transmission (Sanchez-Vargas et al. (2009), supra).

A recently published RNA sequence analysis describing mosquito transcriptional profiles during DENV infection show that all transcripts representing immunity-related genes with differential accumulation in midgut samples were always more abundant in control than DENV mosquitoes, supporting the conclusion that there is a suppression of the insect immune system following infection. This result may reflect the general 'DENV downregulation trend" observed. A similar pattern was seen in carcass samples at early time points postinfection, but the opposite was observed at 14 days post infection (dpi), reflecting a possible change in immune modulation during the course of the infection (Bonizzoni et al. (2012) PLoS ONE 7(11): e50512).

Another method for the biocontrol of vector-born pathogens includes paratransgenesis. Paratransgenesis generally refers to systems whereby symbiotic bacteria are genetically modified and reintroduced in the pathogen-bearing vector, such as mosquitos, where they express effector molecules. However, paratransgenesis has several technical limitations. For example, bacteria to be used in paratransgenesis must generally have three key components: an effector molecule that achieves the desired effect; a mechanism to display or excrete the effector molecule on the surface of the bacteria; and bacteria that can survive in the mosquito long enough to produce the expected amount of effector molecules and thereby achieve the desired effect in the mosquito. Therefore, finding such suitable bacteria that fit all of these criteria is very difficult.

Paratransgenesis is generally understood as a technique that attempts to eliminate a pathogen from vector populations through transgenesis of a symbiont of the vector. The goal of this technique is to control vector-borne diseases. The first step is to identify proteins that prevent the vector species from transmitting the pathogen. The genes coding for these proteins are then introduced into the symbiont, so that they can be expressed in the vector. The final step in the strategy is to introduce these transgenic symbionts into vector populations in the wild. Characteristics of a successful paratransgenesis system may include:

The symbiotic bacteria can be grown in vitro easily.
They can be genetically modified, such as through transformation with a plasmid containing the desired gene.
The engineered symbiont is stable and safe.
The association between vector and symbiont cannot be attenuated.
Field delivery is easily handled.

A paratransgenic system is a system that can achieve paratransgenesis in a target organism.

Identification of suitable commensal bacteria that are non-pathogenic to humans or animals among the many organisms that insects harbor, particularly in their digestive systems, is paramount for the success of a paratransgenic system. In mosquitoes, these bacteria are involved in various biological functions associated with digestion, primarily in the midgut. There is a close association between blood-dependent insects and symbiotic microorganisms that help the anabolic processes of vitellogenesis and ovogenesis. Eradication of these bacteria leads to a decline in fecundity and a slower growth rate. Interference with the digestion of proteins in mosquito blood meals can reduce fecundity and may represent a new approach for controlling mosquito populations and preventing the transmission of pathogens.

For example, the chosen bacteria should be capable of colonizing a wide variety of mosquito species so that they can be deployed in different species and isolated strains. Furthermore, the number of bacteria increases dramatically (100 to 1000 of times) after ingestion of blood, resulting in a proportional increase in the amount of effector molecules expressed and secreted by GM bacteria, leading to various possible outcomes: obstructing pathogen transmission, reducing the mosquito's vector capacity, preventing fertilization of eggs, interfering with embryogenesis and causing the death of the mosquito. These technical and physiological challenges make the development of paratransgenic systems extremely difficult. Importantly, these technical issues are such that many paratransgenic systems are neither effective nor appropriate as an effective biocontrol strategy. These difficulties may also prevent many paratransgenic systems from being appropriately scaled-up to be effective for environmental deployment. Generally, biocontrol means utilizing disease-suppressive microorganisms to eliminate, control or prevent infection, expression and/or transmission of selected pathogens.

To address the shortcomings of these traditional control methods, several other biological or non-chemical control strategies have been developed to control adult mosquito populations, including bacterial infection of mosquitoes to manipulate fitness in the wild and release of sterile males. Although these technologies have potential to control mosquito populations, they also have limitations, such as requirements for on-site rearing and limited local release of millions of engineered or infested mosquitoes at substantial costs. Furthermore, each of these strategies focuses on the control of adult mosquito populations, which must breed (requires a blood meal) for introduction and dissemination of the control strategy. Thus, there is a need for new and effective biocontrol strategies that are robust, effective over long periods of time, and cause the least possible negative environmental impact. To meet these objectives, strategies for vector control must be 1) pathogen (virus)-specific and not kill off-target organisms, 2) robust or catalytic in mode of action, 3) stable and not easily lost throughout mosquito development, 4) efficient to deliver, 5) simple to manage and low cost, and 6) self-sustainable or regenerating.

The foregoing problems regarding the biocontrol of disease-transmitting mosquito populations may represent a long-felt need for an effective and economical solution to the same. While implementing elements may have been available, actual attempts to meet this need may have been lacking to some degree. This may have been due to a failure of those having ordinary skill in the art to fully appreciate or understand the nature of the problems and challenges involved. As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field. As will be discussed in more detail below, the current inventive technology overcomes the limitations of traditional mosquito control systems and in particular paratransgenic systems of biocontrol, while meeting the objectives of a truly effective, and scalable, vector biocontrol strategy.

BRIEF SUMMARY OF THE INVENTION

In one preferred embodiment, the invention may include novel systems and strategies to control mosquito borne disease using a novel, cross-kingdom mechanism to incapacitate and potentially kill mosquitos and their larvae by introducing engineered microorganisms that target mosquito and/or larval health.

One aim of the present invention may include novel paratransgenic biocontrol strategies. In this embodiment, the inventive technology includes various cross-kingdom mechanisms for the knockdown of essential viral genes in all developmental stages of mosquitoes from larvae to adults. This may be accomplished through the introduction of engineered microorganisms into mosquito populations that express specific inhibitory RNA molecules that may downregulate and/or suppress selected viral and/or host genes.

Another aim of the present invention may include infecting mosquitos with novel genetically engineered microorganisms that may express specific inhibitory RNA molecules that may downregulate key viral genes. In one preferred embodiment, one or more microorganisms may be genetically engineered to express dsRNAs that may simultaneously suppress multiple essential viral genes to increase mortality and reduce the likelihood of evolution of resistance mechanisms. One aim of the invention may include the generation of a novel paratransgenic system which may include the transformation of one or more microorganisms to express dsRNAs that may target and suppress one or more pathogen virus genes. This system may include the screening and selection of an appropriate enteric bacteria capable of colonizing the gut of a pathogen-carrying mosquito that may further the transformed to express select dsRNAs that may target and suppress one or more pathogen virus genes. Such targets may include, but not be limited to structural and/or essential genetic elements necessary for virion replication.

Another specific aim of the invention may provide a novel paratransgenic system that may suppress expression and propagation of the Zika virus in mosquitos. This system may include the screening and selection of an appropriate enteric bacteria capable of colonizing the gut of a Zika-carrying mosquito, that may further the transformed to express select dsRNAs that may target and suppress one or more pathogen virus genes. Such targets may include, but not be limited to the generally conserved region of the Zika genome coding for the NS2B-NS3 and NS4 genes.

Another aim of the inventive biocontrol systems may be to optimize dsRNA survival and/or delivery to a disease-carrying vector, such as a mosquito, by co-expression of helper genes that may enhance the uptake, stabilization, and intercellular transfer and/or mobilization of dsRNA in mosquitoes. Examples of such helper genes are provided below in Table 2. For example, one or more microorganisms that may colonize, or be endosymbiotic with the mosquito gut may be genetically modified to express selected interfering RNA molecules, such as dsRNA. Such genetically engineered endosymbiotic bacteria may be introduced into various mosquito populations, for example through oral delivery and/or infection of larvae. For Zika virus control, one or more genetically modified enteric bacteria may express dsRNAs that target the single transcript that encodes structural and/or non-structural genes targets.

Another aim of the invention may include methods of targeting multiple essential virus-specific gene targets for silencing, such that it may be possible to selectively diminish human viral pathogens in adult mosquitoes. As siRNAs may be catalytic in activity, their potential effectiveness and safety may well be greater than that of broad spectrum chemical insecticides thereby overcoming some of the limitations outlined above. In addition, in certain embodiments the inhibitory RNAs are non-immunogenic, such that they can be designed to be species specific so that non-target organisms are not harmed. Finally, since a bacterial-based dsRNA delivery system may be self-sustaining and long-lasting, many fewer applications, such as aerial spraying may be needed.

Another aim of the invention provides for methods of environmental dispersal of these engineered microorganisms. Such methods may utilize aerial (e.g., crop dusters) spraying to cover the greatest land area at the lowest cost. Additional methods of dispersion known within the field may also be contemplated within the inventive technology. Significantly, many microorganisms can persist dried in the soil for multiple years allowing for the re-population of dry areas after precipitation. This is particularly suitable for areas where larval habitats appear and vanish alternatively between dry and rainy seasons. Again, such attributes overcome the limitations of traditional mosquito control systems previously outlined.

Another aim of the inventive technology may include testing procedures to evaluate the acquisition and persistence of the modified microorganism, such as a bioengineered enteric species, in adult mosquitoes as well as dsRNA distribution in adult mosquito tissues and/or larvae. In one preferred embodiment, the effectiveness of an enteric bacterial delivery of siRNA on Zika, or other pathogen's persistence and replication, in mosquitoes may be determined. In this embodiment, mosquitoes carrying an engineered enteric bacteria as well as control mosquitoes may be fed on artificial blood meals containing live Zika virus, incubated for designated periods of time, killed and assayed for presence of virus.

In one embodiment, mosquito gut samples from mosquito larvae and adults captured from the wild (multiple sites may include Brazil, US, and Borneo, and the like) may be collected. These samples may further be analyzed to determine their associated metagenome to identify larval-preferred food microorganisms (algae, cyanobacteria, bacteria) as well as microorganisms that persist in both adults and larvae. Then, it may be possible to down-select and introduce dsRNA validated in Aim 1 into microorganisms that are genetically transformable to enhance dsRNA delivery and dsRNA-mediated killing. As discussed earlier, certain larval gut microbes may persist through instar development into the adult stage. These microbes are particularly attractive for long-term delivery of siRNAs that target mosquitoes, as well as siRNAs that target the human pathogens transmitted by adult mosquitoes, thus providing another layer of disease control.

Other features and advantages of the invention will be apparent from the detailed description, and from the claims.

BRIEF DESCRIPTION OF THE FIGURES

The accompanying figures, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the figures:

FIG. 2: Listing of preliminarily identified target bacteria based on MALDI biotyping and 16S rRNA sequencing.

FIG. 5: Representative growth promotion of mosquitoes by selected endosymbiotic bacteria in one embodiment thereof. Specifically, representative larvae reared with bacterial endosymbionts (Left panel, bacterial isolate Ae165 shown) develop faster than those without bacteria added to the mosquito rearing solution (right panel, negative control).

FIG. 8: Demonstrates secretion of dsRNA from the bacteria.

Figure 1:
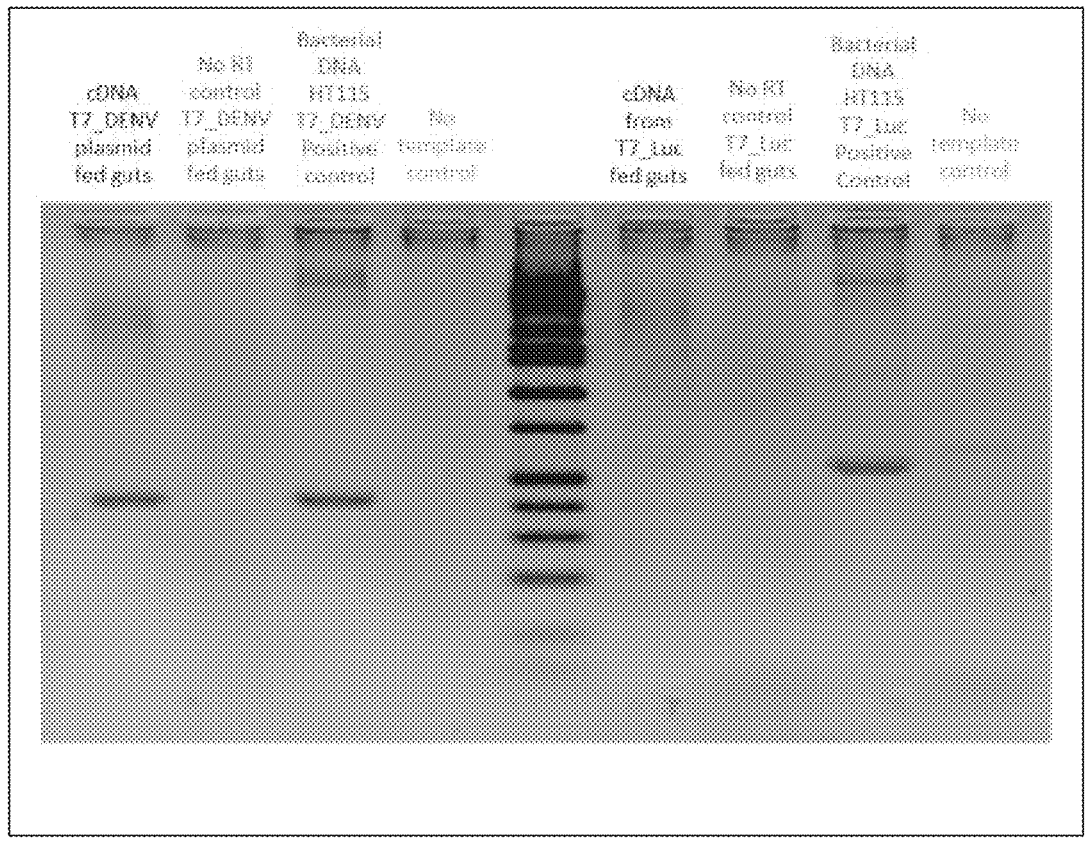
FIG. 1: ds-RNA-Dengue detection in mosquito gut infected with H115 *E. coli* expressing dsRNA-Dengue.

As noted above, in one embodiment the present invention includes a novel paratransgenic system which may further include a novel method for implementation of an RNAi-based strategy in which natural mosquito symbiotic bacteria are transformed with plasmids that express dsRNA derived from specific arbovirus genomes in the *Ae. aegypti* midgut, or gut, to reduce or eliminate transmission of arboviruses.

As noted above, mosquitos, such as the in *Ae. aegypti* species, possess a natural anti-arboviral defense mechanism RNA interference (RNAi). Briefly, by use of the exo-siRNA RNAi pathway, Ae *aegypti* recognizes arboviral long double-stranded (ds)RNA generated during virus replication, digests it to 21-bp short interfering RNA (siRNA) segments with an RNase III family enzyme called Dicer 2, and uses these as effectors to identify, cleave and inactivate replicating virus genomes.

Thus, according to one aspect of the present invention there is provided a method of controlling a pathogenically infected mosquito, the method comprising administering to a larva of a mosquito an isolated nucleic acid agent comprising a nucleic acid sequence which specifically downregulates an expression of at least one mosquito pathogen resistance gene product of the mosquito, wherein downregulation of the expression of the at least one mosquito pathogen resistance gene in the larva renders an adult stage of the mosquito lethally susceptible to the pathogen, thereby controlling the pathogenically infected mosquito. In one preferred embodiment, such a nucleic acid agent may include SEQ ID NOs 1-5. Additional embodiments may include any nucleic acid that spans a region of greater than average homology between the genomes of various strains of a pathogen. In one preferred embodiment, may include any nucleic acid that spans a region of greater than average homology between the genomes of various strains of a Zika or Dengue virus. In the example of a Zika genome, this may include, as shown generally below in the region encoding non-structural proteins NS2B-NS3-NS4 among others.

In one embodiment the present invention includes the generation of a novel paratransgenic system for the biocontrol of pathogen-vectors. The invention may specifically include a paratransgenic system configured to deliver one or more inhibitory RNA molecules to pathogen/disease-transmitting organisms. In one embodiment, the invention may include one or more genetically engineered microorganisms configured to deliver one or more inhibitory RNA molecules to pathogen/disease-transmitting mosquitos. In a preferred embodiment, the invention may include one or more genetically engineered enteric bacteria configured to deliver one or more dsRNA molecules to pathogen/disease-transmitting mosquitos.

Other embodiments of the current invention include the generation of one or more enteric bacteria that may be endosymbiotic with the target disease-transmitting organism, in this case a mosquito. These endosymbiotic enteric bacteria may persist in the gut throughout all stages of mosquito development. This preferred embodiment may include the generation of one or more enteric bacteria that may be endosymbiotic with the target disease-transmitting organism and that may colonize the gut, or mid-gut of the target disease-transmitting organism, in this case a mosquito.

Another embodiment of the invention includes the generation of one or more enteric bacteria that may be endosymbiotic with the target disease-transmitting organism and that may colonize the gut, or mid-gut of the target disease-transmitting organism, in this case mosquitoes that are further genetically modified, or transformed, to produce one or more dsRNA (double-stranded) molecules. These dsRNA molecules may correspond to one or more pathogen genes. Moreover, dsRNA molecules may generate an RNA-mediated downregulation or suppression of select viral genes. This RNA-mediated downregulation or suppression of select viral genes may be through an interfering RNA process as generally described here.

Another embodiment includes the generation of one or more enteric bacteria that may be endosymbiotic with the target disease-transmitting organism and that may colonize the gut, or mid-gut of a Zika-infected mosquito and further configured to continuously deliver dsRNA molecules that correspond to one or more pathogen genes of the Zika virus (ZIKAV), or Dengue virus (DENGV), among other identified herein, and may further elicit an interfering RNA-mediated reaction causing the suppression of the target viral genes.

Additional embodiments of the present invention includes the generation of one or more enteric bacteria that may be endosymbiotic with the target disease-transmitting organism and that may colonize the gut, or mid-gut of a Zika-infected mosquito, and further configured to continuously deliver lethal siRNAs to target mosquito-borne pathogens, such as the Zika virus. The siRNA molecule is preferably an RNA duplex, comprising a sense region and an antisense region, wherein the antisense region includes a plurality of contiguous nucleotides that are complementary to a messenger RNA sequence encoded by the target gene. In one embodiment, the polynucleotide encoding the siRNA comprises at least one nucleotide sequence selected from the group consisting of SEQ ID NO: 1, SEQ ID NO:2, SEQ ID NO:3, SEQ ID NO:4 and SEQ ID NO:5. In a preferred embodiment, a messenger RNA sequence encoded by the target pathogen gene may include a gene located in a region of higher than average homology, or in other words, a gene fully or partially located in the most conserved region of a pathogens genome, when compared to the sequences of other strains of the pathogens of genes. In one specific embodiment, SEQ ID NO:1, SEQ ID NO:2, SEQ ID NO:3, SEQ ID NO:4 and SEQ ID NO:5 correspond to non-structural proteins coding regions in SEQ ID NO:6. Naturally, such sequences are exemplary, as they may be alternatively, redundant or overlapped across one or more distinct gene coding segments.

The present invention may further include one or more vectors for modulating multiple pathogen genes, wherein the vector comprising one, or plurality of dsRNAs may correspond to one or more select pathogen genes. This embodiment may include the use of a plasmid expression system. In some embodiments, this plasmid may have one or more expression cassettes, including: at least one gene suppressing cassette containing a polynucleotide operably-linked to a promoter sequence, wherein the polynucleotide encodes an interfering RNA molecule, such as a dsRNA, or a molecule that will subsequently generate interfering RNA molecule, such as a dsRNA, that reduces expression of a target pathogen gene by RNA interference.

A preferred embodiment of the present invention includes a vector for modulating multiple host genes, wherein the vector comprising one, or plurality of dsRNAs may correspond to one or more select host genes. This embodiment may include the use of a plasmid expression system. In some embodiments, this plasmid may have one or more expression cassettes, including: at least one gene suppressing cassette containing a polynucleotide operably-linked to a promoter sequence, wherein the polynucleotide encodes an interfering RNA molecule, such as a dsRNA, or a molecule that will subsequently generate interfering RNA molecule, such as a dsRNA, that reduces expression of a target host gene by RNA interference.

Another embodiment of the present invention includes a vector for modulating host and pathogen genes, wherein the vector comprising one, or plurality of dsRNAs that may correspond to one or more select host and pathogen genes. This embodiment may include the use of a plasmid expression system. In some embodiments, this plasmid may have one or more expression cassettes, including: at least one gene suppressing cassette containing a first polynucleotide operably-linked to a promoter sequence, wherein the polynucleotide encodes an interfering RNA molecule, such as a dsRNA, or a molecule that will subsequently generate an interfering RNA molecule, such as a dsRNA, that reduces expression of a target host gene by RNA interference. This gene cassette may further contain a second polynucleotide operably-linked to a promoter sequence, wherein the polynucleotide encodes an interfering RNA molecule, such as a dsRNA, or a molecule that will subsequently generate interfering RNA molecule, such as a dsRNA, that reduces expression of a target pathogen gene by RNA interference.

In another aspect, the present invention includes a method of modulating the expression of one or more pathogen genes within a host by administering a vector of the present invention to the host, wherein the first polynucleotide sequence is expressed in the host, wherein this first polynucleotide is transcribed to produce the RNA molecule, and wherein the RNA molecule is capable of reducing expression of a target gene by RNA interference. Additional embodiments, may include a second polynucleotide sequence which may express a helper gene as described elsewhere.

The present invention also includes a vector for inhibiting the expression of viral or bacterial genes in a host, wherein the vector comprises at least one gene suppressing cassette containing a polynucleotide operably-linked to a promoter sequence, wherein the polynucleotide encodes an siRNA molecule that reduces expression of a target pathogen gene within the host by RNA interference. In one embodiment, the polynucleotide encoding the siRNA comprises the nucleotide sequence of SEQ ID NO:1, SEQ ID NO:2, SEQ ID NO:3, SEQ ID NO:4, SEQ ID NO:5.

Likewise, the vectors of the present invention can include a plurality of gene suppressing cassettes, wherein each gene suppressing cassette contains a polynucleotide encoding an siRNA molecule, such as a dsRNA, that targets the same mRNA sequence or different mRNA sequences. For example, each gene suppressing cassette can encode a dsRNA molecule that targets an mRNA sequence of two or more different genes. Furthermore, each vector of the present invention can include a plurality of gene promoting cassettes and a plurality of gene suppressing cassettes.

Examples of suitable promoters for gene suppressing cassettes include, but are not limited to, T7 promoter, bla promotor, U6 promoter, pol II promoter, EII promoter, and CMV promoter and the like. Optionally, each of the promoter sequences of the gene promoting cassettes and the gene suppressing cassettes can be inducible and/or tissue-specific.

The vectors of the present invention can be non-viral, such as plasmids, or viral vectors, such as adenovirus, adeno associated virus, poliovirus, lentivirus, FISV, or murine Maloney-based virus. Any pathogen gene may be targeted for interference. In one embodiment, the viral gene may be a viral gene of an arbovirus pathogen such as Alphaviruses pathogens (e.g. Eastern Equine encephalitis virus, Western Equine encephalitis virus, Venezuelan Equine encephalitis virus, Ross River virus, Sindbis Virus and Chikungunya virus), Flavivirus pathogens (e.g. Zika virus, Japanese Encephalitis virus, Murray Valley Encephalitis virus, West Nile Fever virus, Yellow Fever virus, Dengue Fever virus, St. Louis encephalitis virus, and Tick-borne encephalitis virus), Bunyavirus pathogens (e.g. La Crosse Encephalitis virus, Rift Valley Fever virus, and Colorado Tick Fever virus), Orthobunyavirus pathogens (e.g. Oropouche virus), and Orbivirus (e.g. Bluetongue disease virus)).

Additional pathogen genes may be targeted for interference. In one embodiment, the worm pathogen gene may be a viral gene of nematodes that may infect mosquitos, or other organisms, e.g. filarial nematodes such as *Wuchereria bancrofti, Bmgia malayi, Bmgia pahangi, Brugia timori* and heartworm (*Dirofilaria immitis*).

Additional pathogen genes may be targeted for interference. In one embodiment, the bacterial gene may be a viral gene of gram negative and gram positive bacteria that infect mosquitos, or other organisms, including *Yersinia pestis, Borellia* spp, *Rickettsia* spp, and *Erwinia carotovora*.

Additional pathogen genes may be targeted for interference. In one embodiment, the bacterial gene may be a viral gene of a pathogen that may be transmitted by mosquitoes including the Malaria parasite of the genus *Plasmodium* e.g. *Plasmodium falciparum, Plasmodium vivax, Plasmodium ovale, Plasmodium malariae, Plasmodium berghei, Plasmodium gallinaceum*, and *Plasmodium knowlesi*.

A target gene may include sequences encoding polypeptides or polynucleotide sequences that regulate the replication, transcription, translation or other process important to the expression of the gene. The target gene need not necessarily encode a polypeptide but may encode other cellular components, such as ribosomal RNA, splicosome RNA, transfer RNA, etc. For example, regulatory sequences of pathogen, such as a Zika virus can be targeted. The target sequence may be the entire sequence of the target gene, or, preferably, only a portion of the target gene.

In a preferred embodiment, a siRNA having a dinucleotide 3' overhang, has been demonstrated to bypass the antiviral response and induce gene specific silencing in mammalian cells. In one preferred embodiment, the sense region and the antisense region of the siRNA molecule are connected. Preferably, the sense region and antisense region are covalently connected via a linker molecule (also referred to herein as a "space"), such as a polynucleotide linker. The polynucleotide linker can be various lengths. Preferably, the linker is in the range of about 6 to 12 nucleotides in length.

In a preferred embodiment, the siRNA molecule is partially self-complementary and, therefore, forms a stem and loop structure. The sense region and antisense region of the RNA duplex contain one or more mismatches, such that a bulge or secondary structure (such as a hairpin structure) is formed. Preferably, the RNA duplex contains within the range of about 4 to about 23 nucleotide base pair mismatches. More preferably, the RNA duplex contains within the range of about 7 to about 9 nucleotide base pair mismatches. In an alternative embodiment, the siRNA molecule comprises two separate strands (a sense strand and antisense strand) that are substantially complementary so that they form a duplex upon provision of appropriate conditions.

In yet another aspect, the present invention includes a method of modulating the expression of one or more pathogen genes within a host by administering a vector of the present invention to the host, wherein the first polynucleotide sequence is expressed in the host, wherein this first polynucleotide is transcribed to produce the dsRNA molecule, and wherein the dsRNA molecule is capable of reducing expression of a target gene by RNA interference. Additional embodiments may include a second polynucleotide sequence which may express a helper gene as described elsewhere.

The present invention may also include a vector for inhibiting the expression of viral or bacterial genes in a host, wherein the vector comprises at least one gene suppressing cassette containing a polynucleotide operably-linked to a promoter sequence, wherein the polynucleotide encodes an siRNA molecule that may be configured to reduce expression of a target viral or bacterial gene within the host by RNA interference. Any viral or bacterial gene may be targeted for interference. In one embodiment, the viral gene is a Dengue virus (DV) gene. Any gene of the Dengue virus genome (approximately 11,000 nucleotides) can be targeted. The target gene can encode a structural protein or non-structural protein, for example. Typically, the target Dengue gene will encode at least one protein selected from the group consisting of C, prM, E, NS1, NS2a, NS3, NS4a, NS4b, and NS5. A gene region may also be targeted based, in some embodiments on conserved sequence homology across various Dengue strains. Optionally, the vector further includes at least one gene promoting cassette comprising a polynucleotide operably-linked to a promoter sequence. In another aspect, the present invention includes a method of inhibiting the expression of bacterial or viral genes (such as Dengue virus genes) within a host by administering the vector to the host, wherein the polynucleotide sequence is transcribed to produce the siRNA molecule, and wherein the siRNA molecule is capable of reducing expression of a target bacterial or viral gene (such as Dengue virus) within the host by RNA interference. Thus, the present invention includes methods of inhibiting bacterial or viral infections (such as Dengue virus) by administering such vectors to the host.

The present invention also includes a vector for inhibiting the expression of viral or bacterial genes in a host, wherein the vector comprises at least one gene suppressing cassette containing a polynucleotide operably-linked to a promoter sequence, wherein the polynucleotide encodes an siRNA molecule that may be configured to reduce expression of a target viral or bacterial gene within the host by RNA interference. Any viral or bacterial gene may be targeted for interference. In one embodiment, the viral gene is a Zika virus gene. Any gene of the Zika virus genome (approximately 11,000 nucleotides) can be targeted. The target gene can encode a structural protein or non-structural protein, for example. Typically, the target Dengue gene will encode at least one protein selected from the group consisting of C, prM, E, NS1, NS2A, NS2B, NS3, NS4A, 2K, NS4B, and NS5. A gene region may also be targeted based, in some embodiments on conserved sequence homology across various Zika strains. Optionally, the vector further includes at least one gene promoting cassette comprising a polynucleotide operably-linked to a promoter sequence. In another aspect, the present invention includes a method of inhibiting the expression of bacterial or viral genes (such as Zika virus genes) within a host, by administering the vector to the host, wherein the polynucleotide sequence is transcribed to produce the siRNA molecule, and wherein the siRNA molecule is capable of reducing expression of a target bacterial or viral gene (such as Zika virus) within the host by RNA interference. Thus, the present invention includes methods of inhibiting bacterial or viral infections (such as Zika virus) by administering such vectors to the host.

In further aspects, the present invention includes pharmaceutical compositions comprising a therapeutically effective amount of any the vectors of the present invention and a pharmaceutically acceptable carrier.

Another aim of the present invention may be novel methods to control the levels and timing of the expression of inhibitory RNA molecules (e.g., dsRNA) in the target bacteria. In one preferred embodiment, the expression of one or more asRNA molecules may be under the control of a novel gene switch that may be incorporated into a plasmid vector. This gene switch may be controlled by a switch molecule, which may be a water-soluble and food-grade molecule that can be added to a host organism's environment or a food supply. The presence of this switch molecule may activate, for example, dsRNA production. In its absence, dsRNA production may not occur, or may only occur at negligible levels.

An additional aspect of the invention may include novel methods to provide genetically engineered enteric-bacteria that may be configured to colonize the mosquito's midgut and prevent viral pathogens from escaping the midgut into the surrounding epithelium. More specifically, one aim of the invention may be to introduce genetically engineered enteric-bacteria to the mosquito's midgut and be further configured to produce and secrete dsRNA into the midgut. These dsRNA molecules may be taken up by the surrounding epithelial cells causing a strong RNAi cascade preventing viral replication, and/or suppressing pathogen levels such that no significant number of virions can migrate from the epithelial cells surrounding the mosquito's midgut to a mosquito's salivary glands.

One preferred embodiment of the present invention may be to provide bacteria that may further be genetically engineered to express inhibitory RNA molecules, such as dsRNA, shRNA (that may contain an intron from a targeted organism located at the hairpin loop of the dsRNA), siRNA, and microRNAs. These inhibitory RNA molecules may inactivate and/or knock-down expression of targeted genes in pathogens through generation of ~21-22 nucleotide siRNAs mediated by the host's Dicer/RISC complex. This process may generally be referred to as RNA interference or RNAi.

As noted above, in one embodiment, the novel paratransgenic system may comprise systems and methods to control the virulence of specific pathogens by selective inactivation of pathogenic, essential or other genes. This targeted gene inactivation may be accomplished by the expression and delivery of inhibitory RNA molecules, such as double stranded RNA (dsRNA) or small hairpin (shRNA), to the target host cells where virus replication may occur. In a preferred embodiment, the dsRNA generated by the genetically modified bacteria now colonized in the mosquito gut may be taken up by the surrounding epithelial cells which may recognize the dsRNA and initiate an RNA-mediated interfering cascade preventing viral replication, and/or suppressing pathogen levels such that no significant number of virions can migrate from the epithelial cells surrounding the mosquito's midgut to a mosquito's salivary glands.

Specifically, in the target host's epithelial cells, the dsRNA may be processed into small interfering RNAs (siRNAs) of—approximately 21 nucleotides in length through the action of the enzyme, Dicer. These siRNAs may further interact with the Ago and RISC protein complexes to bind to the targeted pathogen-specific mRNA sequence. Finally, the RISC complex may cleave the pathogen-specific mRNA silencing or knocking down the expression of the targeted pathogenic or other target gene and blocking pathogen virulence, replication and/or proliferation.

Delivery of the inhibitory RNA molecules to a target animal/cell/tissue may be accomplished through a trans-kingdom delivery system. In a preferred embodiment, the delivery of inhibitory RNA molecules may be accomplished through the introduction of genetically modified host-specific microorganisms, such as enteric or other bacteria. Since bacteria cannot process dsRNA to siRNA as they lack the Dicer/RISC machinery, dsRNA delivered to a target host must be processed by the host into siRNAs that may inactivate the targeted viral gene. Such genetically modified host-specific microorganisms may include: 1) microorganisms that are part of the target animals normal internal or external bacterial microbiome; 2) microorganisms that have been modified to be capable of colonizing a target animal, tissue, cell or host environment; 3) microorganisms that that are utilized as a food or energy source by the target host; or 4) microorganisms that have been modified to colonize a specific animal, tissue, cell or host environment. In this embodiment, the colonized bacteria may express inhibitory RNA molecules, such as dsRNA/shRNAs, that may further be processed by the host's DICER/RISC complex allowing pathogen-specific mRNA silencing/inactivation of essential pathogen genes. Moreover, these colonized enteric bacteria, having become a part of the host's natural microbiome, may continuously deliver the dsRNA molecules via the intestine from the earliest larval stages to the adult stage providing pathogen-specific mRNA silencing/inactivation of essential pathogen genes throughout the host's lifecycle. In addition, as the enteric bacteria vector may be an already naturally occurring part of the host's microbiome, its' presence may not pose any risk to the organism, environment or end-consumers.

In additional embodiment, target epithelial cells may uptake dsRNA secreted by transformed paratransgenic bacteria located in the mosquito's gut through endocytic, vesicular trafficking, phagocytosis and/or other active or passive polynucleotide transport processes.

The present invention, in some embodiments thereof, relate to isolated nucleic acid agents, and, more particularly, but not exclusively, to the use of the same for controlling pathogenically infected mosquitoes. Insects are vectors for numerous pathogens, including viruses, bacteria, protozoa and nematodes.

Another aspect of the inventive technology may include a novel paratransgenic system for the biocontrol of pathogens. The inventive technology may further include a novel paratransgenic system for the biocontrol of mosquito-borne pathogens, and in particular mosquito-borne viral pathogens that may be pathogenic to humans, such as the Dengue or Zika viruses respectively. It should be noted that the action of, for example downregulating a pathogen gene, may also specifically encompass downregulation of a pathogen's gene from being transcribed. It should not be considered to be limited to either a downregulation of merely transcription or translations, but explicitly both.

Another aspect of the inventive technology may include novel methods and systems for the generation of genetically modified microorganisms configured to deliver one or more dsRNA capable of inducting an siRNA inhibitory cascade reaction, for example, through the action of mosquito-endogenous Dicer processing of the dsRNA, thereby reducing expression of, or in some cases silencing a pathogen encoded gene. The present invention may generate a paratransgenic system directed to suppressing pathogens in mosquitos, where the mosquito is of a species selected from the group consisting of *Aedes aegypti*, *Aedes albopictus* and *Anopheles gambiae*. This paratransgenic system may be employed for the biocontrol of: a viral infection, a nematode infection, a protozoa infection and a bacterial infection.

Another embodiment of the present invention may include novel methods generating a paratransgenic system directed to suppressing arbovirus pathogens, where the arbovirus may be selected from the group consisting of an alphavirus, a flavivirus, a bunyavirus and an orbivirus. According to some embodiments of the invention, the arbovirus is selected from the group consisting of a La Crosse encephalitis virus, an Eastern equine encephalitis virus, a Japanese encephalitis virus, a Western equine encephalitis virus, a St. Louis encephalitis virus, a Tick-borne encephalitis virus, a Ross River virus, a Venezuelan equine encephalitis virus, a Chikungunya virus, a West Nile virus, a Dengue virus, a Yellow fever virus, a Bluetongue disease virus, a Sindbis Virus, a Rift Valley Fever virus, a Colorado tick fever virus, a Murray Valley encephalitis virus, an Oropouche virus, a Flock House virus and a Zika virus and the like.

Alternative aspects of the present invention may include novel methods to generate a paratransgenic system directed to suppressing protozoa pathogens, such as infections caused by a *Plasmodium*. According to some embodiments of the invention, the protozoa infection causes malaria. Another embodiment of the present invention is to generate a paratransgenic system directed to suppressing nematode pathogens. According to some embodiments of the invention, the nematode infection is caused by a Heartworm (*Dirofilaria immitis*) or a *Wuchereria bancrofti*.

Another inventive aspect of the present invention may be to provide a mosquito larva-ingestible compound comprising an isolated nucleic acid agent and a nucleic acid sequence, as a dsRNA, which specifically downregulates expression of at least one mosquito pathogen gene in a mosquito and a microorganism or algae on which mosquito larva feed. According to some embodiments of the invention, the mosquito larva-ingestible compound of some embodiments of the invention may be formulated as a solution. According to some embodiments of the invention, the mosquito larva-ingestible compound is formulated in a solid or semi-solid formulation.

According to some embodiments of the invention, the gene is selected from the group consisting of one or more target pathogen genes that are essential to virulence, coat proteins, metabolic activity, infection pathways and/or energy-production and the like. A target gene may include one or more genes that are responsible for pathogenicity, or the capacity to cause a disease condition in the host. Examples of such target genes may also include one or more virulence factors. Examples of such virulence factors may include, but not be limited to:

Adherence Factors: This group may include genes that help bacterial pathogens adhere to certain cells;

Invasion Factors: This group may include genes for surface components that allow the bacterium to invade host cells;

Capsules: This group may include genes for structural capsules that may protect bacteria from opsonization and phagocytosis;

Endotoxins: This group may include genes for several types of toxic lipopolysaccharides that may elicit an immune response;

Exotoxins: This group may include genes for several types of protein toxins and enzymes produced and/or secreted from pathogenic bacteria. Major categories include cytotoxins, neurotoxins, and enterotoxins;

Siderophores: This group may include genes for several types of iron-binding factors that allow some bacteria to compete with the host for iron, which is bound to hemoglobin, transferrin, and lactoferrin;

Host-Conversion Factors: This group may include genes that alter the metabolism of the host to the benefit of the pathogen, including but not limited to evading host defenses.

One preferred embodiment of the present invention may include an isolated nucleic acid agent, comprising a polynucleotide expressing a nucleic acid sequence which specifically downregulates an expression of at least one pathogen gene. In a preferred embodiment, this isolated nucleic acid agent may comprise a polynucleotide expressing a dsRNA sequence which specifically downregulates an expression of at least one mosquito pathogen through a siRNA process. Another embodiment of the present invention may include a nucleic acid construct comprising a nucleic acid sequence encoding the isolated nucleic acid agent, such as a dsRNA or a nucleic acid agent that may form into a dsRNA, of some embodiments of the invention.

Bacterial RNAse IIIs may degrade inhibitory RNA molecules such as dsRNA. In one embodiment, the inventive technology may include modification of the previously identified host-specific bacteria to have decreased RNase III expression, or inactivated RNase III function or activity. This decrease or inactivation in RNAase III expression and/or activity may inhibit or decrease RNase III-mediated processing of dsRNA into smaller RNA species. In one preferred embodiment, the previously identified host-specific bacteria may be genetically modified to efficiently express inhibitory RNA molecules in an RNAse III deficient background. In this preferred embodiment, the RNAse IIIs genes of the host-specific bacteria may be knocked out by homologous recombination or other appropriate methods.

Another embodiment of the inventive technology may include systems and methods to facilitate the overexpression of host-specific bacterial genes known to enhance stabilization and/or mobilization of inhibitory RNA molecules. In this preferred embodiment, one or more genes known to stabilize dsRNA may be over-expressed to enhance its lifetime and that facilitate its movement within host organism/cell/tissue. In another preferred embodiment, one or more genes that regulate or suppress genes that are known to stabilize dsRNA may be knocked-out, resulting in their upregulation, thereby enhancing dsRNA's lifetime to facilitate its movement within the host organism to enhance the viral gene inhibition. Additional embodiments may also overexpress genes or target gene knockouts that may result in the up-regulation of membrane vesicular trafficking to facilitate dsRNA mobilization and delivery to the host organism.

Each of the aforementioned systems may be embodied in genetic constructs that may include transcription regulation elements such as promoters, terminators, co-activators and co-repressors and other control elements at may be regulated in prokaryotic as well as eukaryotic systems. Such systems may allow for control of the type, timing and amount of, inhibitory RNA molecules or other proteins, expressed within the system. Additional embodiments may include genetic constructs that may be induced through additional outside and/or environmental factors, such as the presence of a specific protein or compound, such as stress related proteins generated in response to a pathogen or even proteins and other precursor compounds generated by pathogens and the like. Such beneficial co-expressed polypeptides may generally be referred to as "helper" genes or "helper" proteins.

Another embodiment of the present invention may include a cell comprising the isolated nucleic acid agent, such as a dsRNA, or the nucleic acid construct, such as a plasmid, of some embodiments of the invention. The present invention may further include a cell comprising the isolated nucleic acid agent, such as a dsRNA, or the nucleic acid construct, such as a plasmid, of some embodiments of the invention that may further include one or more "helper" genes that may aid in pathogen gene suppression, dsRNA survival, dsRNA uptake, dsRNA secretion and the like. Another aim of the present invention may include the use of an autotrophic bacteria, as well as an RNase III deficient strain of bacteria as a nucleic acid agent (e.g., dsRNA) transmission vector.

Another embodiment of the present invention may include a cell comprising the isolated nucleic acid agent, such as a dsRNA, or the nucleic acid construct, such as a plasmid, of some embodiments of the invention wherein the cell is selected from the group consisting of a bacterial cell, an algae call, an enteric bacteria, and a cell of a water surface microorganism. According to an aspect of some embodiments of the present invention there is provided a mosquito larva-ingestible compound comprising the cell of some embodiments of the invention.

According to some embodiments of the invention, the nucleic acid agent is a dsRNA. According to some embodiments of the invention, the dsRNA is selected from the group consisting of siRNA, shRNA and miRNA. According to other embodiments of the invention, the nucleic acid agent is a polynucleotide that initiates siRNA mediated gene suppression. In some embodiments of the invention, the nucleic acid sequence is between 15 and 530 base pairs in length. According to some embodiments of the invention, the nucleic acid sequence is between 15 and 2650 base pairs in length. According to some embodiments of the invention, the nucleic acid sequence is greater than 2650 base pairs in length. According to some embodiments of the invention, the nucleic acid sequence is 530 base pairs in length.

According to alternative embodiments of the invention, the nucleic acid sequence directly corresponds with a pathogen gene, while in alternative embodiments the nucleic acid sequence corresponds, or overlaps with one or more pathogen genes. According to some embodiments of the invention, the dsRNA nucleic acid sequence directly corresponds with a pathogen gene, while in alternative embodiments the dsRNA nucleic acid sequence corresponds, or overlaps with one or more pathogen genes.

As noted above, according to some embodiments of the invention, the nucleic acid sequence directly corresponds with a Zika virus gene (e.g., NS2B, NS3, or NS4 genes), while in alternative embodiments the nucleic acid sequence corresponds, or overlaps with one or more Zika virus genes (e.g., one or more portions of the sequencing spanning the NS2B-NS3-NS4 genes). According to some embodiments of the invention, the dsRNA nucleic acid sequence corresponds with a Zika virus gene, while in alternative embodiments the dsRNA nucleic acid sequence corresponds, or overlaps with one or more pathogen genes.

According to additional embodiments of the present invention, the nucleic acid sequence directly corresponds with a genome sequence that has a higher degree of homology to the same genome segments in other strains of the pathogen compared to other corresponding genome portions. According to some embodiments of the invention, the dsRNA nucleic acid sequence corresponds with a genome sequence of a Zika virus that has a higher degree of homology to the same genome segments in other strains of the pathogen compared to other corresponding genome portions.

One embodiment of the present invention may include a novel in vitro and/or in vivo method to select optimized dsRNA sequences to selected portions of a pathogens genome based on homology between different strains. The optimized dsRNA sequences may provide higher rates of gene and/or pathogen suppression in vitro and/or in vivo.

Alternative embodiments of the present invention may include a novel in vitro and/or in vivo method to select endosymbiotic bacteria that may be utilized in an effective paratransgenic system of pathogen gene suppression. In particular, another aim of the present invention may include a novel in vitro and/or in vivo method to select endosymbiotic mosquito enteric bacteria that may utilized in an effective paratransgenic system of pathogen gene suppression. These endosymbiotic mosquito enteric bacteria may be non-pathogenic in humans, culturability, transformability, plasmid mobilization, able to secrete target nucleic acids such as dsRNA and the like, endemic or able to become endemic in wild mosquito populations, dispersible, for example through aerosolization, able to survive in the environment and be eaten or taken up by mosquitos at all stages of life with limited exposure, feedings of uptake required by the target mosquito.

In another aspect, the present invention includes methods for producing the vectors of the present invention. In yet another aspect, the present invention includes methods for producing the transformed or genetically modified microorganisms of the present invention, for example through transformation with a recombinant plasmid such as the one shown in FIG. 10.

The term "mosquito" or "mosquitoes" as used herein, refers to an insect of the family Culicidae. The mosquito of the invention may include an adult mosquito, a mosquito larva, a pupa or an egg thereof. Typically, a mosquito's life cycle includes four separate and distinct stages: egg, larva, pupa, and adult. Thus, a mosquito's life cycle begins when eggs are laid on a water surface (e.g. *Culex, Culiseta*, and *Anopheles* species) or on damp soil that is flooded by water (e.g. *Aedes* species). Most eggs hatch into larvae within 48 hours. The larvae live in the water, feeding on microorganisms and organic matter and come to the surface to breathe. They shed their skin four times, growing larger after each molting, and on the fourth molt the larva changes into a pupa. The pupal stage is a resting, non-feeding stage of about two days. At this time the mosquito turns into an adult. When development is complete, the pupal skin splits and the mosquito emerges as an adult.

According to one embodiment, the mosquitoes are of the sub-families Anophelinae and Culicinae. According to one embodiment, the mosquitoes are of the genus *Culex, Culiseta, Anopheles* and *Aedes*. Exemplary mosquitoes include, but are not limited to, *Aedes* species e.g. *Aedes aegypti, Aedes albopictus, Aedes polynesiensis, Aedes australis, Aedes cantator, Aedes cinereus, Aedes rusticus, Aedes vexans', Anopheles* species e.g. *Anopheles gambiae, Anopheles freeborni, Anopheles arabiensis, Anopheles funestus, Anopheles gambiae Anopheles moucheti, Anopheles balabacensis, Anopheles baimaii, Anopheles culicifacies, Anopheles dims, Anopheles latens, Anopheles leucosphyrus, Anopheles maculatus, Anopheles minimus, Anopheles fluviatilis* sd., *Anopheles sundaicus Anopheles superpictus, Anopheles farauti, Anopheles punctulatus, Anopheles sergentii, Anopheles stephensi, Anopheles sinensis, Anopheles atroparvus, Anopheles pseudopunctipennis, Anopheles bellator* and *Anopheles cruzii', Culex* species e.g. *C. annulirostris, C. antennatus, C. jenseni, C. pipiens, C. pusillus, C. quinquefasciatus, C. rajah, C. restuans, C. salinarius, C. tarsalis, C. territans, C. theileri* and *C. tritaeniorhynchus*; and *Culiseta* species e.g. *Culiseta incidens, Culiseta impatiens, Culiseta inornata* and *Culiseta particeps.*

According to one embodiment, the mosquitoes are capable of transmitting disease-causing pathogens. The pathogens transmitted by mosquitoes include viruses, protozoa, worms and bacteria.

As used herein, the phrase "host" or "pathogenically infected mosquito" refers to a mosquito carrying a disease-causing pathogen. Typically the mosquito is infected with the pathogen (e.g. via a blood meal) and acts as a vector for the pathogen, enabling replication of the pathogen (e.g. in the mid gut and salivary glands of the mosquito) and transmission thereof into a host.

Non-limiting examples of mosquitoes and the pathogens which they transmit include species of the genus *Anopheles* (e.g. *Anopheles gambiae*) which transmit malaria parasites as well as microfilariae, arboviruses (including encephalitis viruses) and some species also transmit *Wuchereria bancrofti*; species of the genus *Culex* (e.g. *C. pipiens*) which transmit West Nile virus, filariasis, Japanese encephalitis, St. Louis encephalitis and avian malaria; species of the genus *Aedes* (e.g. *Aedes aegypti, Aedes albopictus* and *Aedes* polynesiensis) which transmit nematode worm pathogens (e.g. heartworm (*Dirofilaria immitis*)), arbovirus pathogens such as Alphaviruses pathogens that cause diseases such as Eastern Equine encephalitis, Western Equine encephalitis, Venezuelan equine encephalitis and Chikungunya disease; Flavivirus pathogens that cause diseases such as Japanese encephalitis, Murray Valley Encephalitis, West Nile fever, Yellow fever, Dengue fever, and Bunyavirus pathogens that cause diseases such as LaCrosse encephalitis, Rift Valley Fever, and Colorado tick fever.

According to one embodiment, pathogens that may be transmitted by *Aedes aegypti* are Dengue virus, Yellow fever virus, Chikungunya virus and heartworm (*Dirofilaria immitis*). According to one embodiment, pathogens that may be transmitted by *Aedes albopictus* include West Nile Virus, Yellow Fever virus, St. Louis Encephalitis virus, Dengue virus, and Chikungunya fever virus. According to one embodiment, pathogens that may be transmitted by *Anopheles gambiae* include malaria parasites of the genus *Plasmodium* such as, but not limited to, *Plasmodium falciparum, Plasmodium vivax, Plasmodium ovale, Plasmodium malariae, Plasmodium berghei, Plasmodium gallinaceum*, and *Plasmodium knowlesi.*

As used herein, the term "controlling" and/or "bio-control" refers to reducing and/or regulating pathogen/disease progression and/or transmission.

The term "nucleic acid" as used herein, refers to a polymer of ribonucleotides or deoxyribonucleotides. Typically, "nucleic acid or "nucleic acid agent" polymers occur in either single or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed, over-expressed, under expressed or not expressed at all.

The terms "genetically modified," "bio-transformed," "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation into its genetic material is a genetically altered organism.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An "expression vector" is a nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, expression vectors are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassette assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is "operably linked to an expression control sequence(s)" (e.g., a promoter and, optionally, an enhancer) when the expression control sequence controls and regulates the transcription and/or translation of that polynucleotide sequence. As used herein, the phrase "gene product" refers to an RNA molecule or a protein.

This invention utilizes routine techniques in the field of molecular biology. Basic texts disclosing the general methods of use in this invention include Green and Sambrook, 4th ed. 2012, Cold Spring Harbor Laboratory; Kriegler, Gene Transfer and Expression: A Laboratory Manual (1993); and Ausubel et al., eds., Current Protocols in Molecular Biology, 1994-current, John Wiley & Sons. Unless otherwise noted, technical terms are used according to conventional usage. Definitions of common terms in molecular biology maybe found in e.g., Benjamin Lewin, Genes IX, published by Oxford University Press, 2007 (ISBN 0763740632); Krebs, et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The present teachings contemplate the targeting of homologs and orthologs according to the selected mosquito species. Homologous sequences include both orthologous and paralogous sequences. The term "paralogous" relates to gene-duplications within the genome of a species leading to paralogous genes. The term "orthologous" relates to homologous genes in different organisms due to ancestral relationship. Thus, orthologs are evolutionary counterparts derived from a single ancestral gene in the last common ancestor of given two species (Koonin EV and Galperin MY (Sequence—Evolution—Function: Computational Approaches in Comparative Genomics. Boston: Kluwer Academic; 2003. Chapter 2, Evolutionary Concept in Genetics and Genomics. Available from: ncbi(dot)nlm(dot)nih (dot)gov/books/NBK20255) and therefore have great likelihood of having the same function. As such, orthologs usually play a similar role to that in the original species in another species.

Homology (e.g., percent homology, sequence identity+ sequence similarity) can be determined using any homology comparison software computing a pairwise sequence alignment. As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9], According to a specific embodiment, the homolog sequences are at least 60%, 65%, 70%, 75%, 80%, 85%, 90%, 95% or even identical to the sequences (nucleic acid or amino acid sequences) provided herein. Homolog sequences of SEQ ID Nos 1-6 of between 50%-99% may be included in certain embodiments of the present invention.

Downregulating expression of a pathogen resistance gene product of a mosquito can be monitored, for example, by direct detection of gene transcripts (for example, by PCR), by detection of polypeptide(s) encoded by the gene (for example, by Western blot or immunoprecipitation), by detection of biological activity of polypeptides encode by the gene (for example, catalytic activity, ligand binding, and the like), or by monitoring changes in the mosquitoes (for example, reduced motility of the mosquito etc). Additionally or alternatively downregulating expression of a pathogen resistance gene product may be monitored by measuring pathogen levels (e.g. viral levels, bacterial levels etc.) in the mosquitoes as compared to wild type (i.e. control) mosquitoes not treated by the agents of the invention.

As generally noted above, according to some aspects of the invention, there is provided an isolated nucleic acid agent comprising a nucleic acid sequence, which specifically downregulates the expression of at least one mosquito pathogen resistance gene product. According to one embodiment, the agent is a polynucleotide agent, such as an RNA silencing agent. In a preferred embodiment, agent is a polynucleotide agent, such as dsRNA, configured to induce RNA interference.

As used herein, the term "interfering RNA molecules" or "interfering RNA" refers to an RNA which is capable of inhibiting or "silencing" the expression of a target gene. In certain embodiments, the RNA silencing agent is capable of preventing complete processing (e.g. the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

In some embodiments of the invention, the nucleic acid agent is a double stranded RNA (dsRNA). As used herein the term "dsRNA" relates to two strands of anti-parallel polyribonucleic acids held together by base pairing. Examples include SEQ ID NOs 1-5. The two strands can be of identical length or of different lengths provided there is enough sequence homology between the two strands that a double stranded structure is formed with at least 60%, 70% 80%, 90%, 95% or 100% complementary over the entire length. According to an embodiment of the invention, there are no overhangs for the dsRNA molecule. According to another embodiment of the invention, the dsRNA molecule comprises overhangs. According to other embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed.

It will be noted that the dsRNA can be defined in terms of the nucleic acid sequence of the DNA encoding the target gene transcript, and it is understood that a dsRNA sequence corresponding to the coding sequence of a gene comprises an RNA complement of the gene's coding sequence, or other sequence of the gene which is transcribed into RNA.

The inhibitory RNA sequence can be greater than 90% identical, or even 100% identical, to the portion of the target gene transcript. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60 degrees C. hybridization for 12-lb hours; followed by washing). The length of the double-stranded nucleotide sequences complementary to the target gene transcript may be at least about 18, 19, 21, 25, 50, 100, 200, 300, 400, 491, 500, 550, 600, 650, 700, 750, 800, 900, 1000 or more bases. In some embodiments of the invention, the length of the double-stranded nucleotide sequence is approximately from about 18 to about 530, or longer, nucleotides in length.

The present teachings relate to various lengths of dsRNA, whereby the shorter version i.e., x is shorter or equals 50 bp (e.g., 17-50), is referred to as siRNA or miRNA. Longer dsRNA molecules of 51-600 are referred to herein as dsRNA, which can be further processed for siRNA molecules. According to some embodiments, the nucleic acid sequence of the dsRNA is greater than 15 base pairs in length. According to yet other embodiments, the nucleic acid sequence of the dsRNA is 19-25 base pairs in length, 30-100 base pairs in length, 100-250 base pairs in length or 100-500 base pairs in length. According to still other embodiments, the dsRNA is 500-800 base pairs in length, 700-800 base pairs in length, 300-600 base pairs in length, 350-500 base pairs in length or 400-450 base pairs in length. In some embodiments, the dsRNA is 400 base pairs in length. In some embodiments, the dsRNA is 750 base pairs in length.

The term "siRNA" refers to small inhibitory RNA duplexes (generally between 17-30 base pairs, but also longer e.g., 31-50 bp) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC. It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

In certain embodiment, dsRNA can come from 2 sources; one derived from gene transcripts generated from opposing gene promoters on opposite strands of the DNA and 2) from fold back hairpin structures produced from a single gene promoter but having internal complimentary. For example, strands of a double-stranded interfering RNA (e.g., a siRNA) may be connected to form a hairpin or stem-loop structure (e.g., a shRNA). Thus, as mentioned the RNA silencing agent may also be a short hairpin RNA (shRNA). The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550, SEQ ID NO: 302) and 5'-UUU-GUGUAG-3' (Castanotto, D. et al. (2002) RNA 8:1454, SEQ ID NO: 303). It will be recognized by one of skill in the art that the resulting single chain oligonucleotide forms a stem-loop or hairpin structure comprising a double-stranded region capable of interacting with the RNAi machinery.

As used herein, the phrase "microRNA (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence, essentially complementary to the nucleotide sequence of the miRNA molecule. Typically, a miRNA molecule is processed from a "pre-miRNA" or as used herein a precursor of a pre-miRNA molecule by proteins, such as DCL proteins, and loaded onto a RISC complex where it can guide the cleavage of the target RNA molecules. Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides, which can adopt a secondary structure comprising an imperfect double stranded RNA stem and a single stranded RNA loop (also referred to as "hairpin"), and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nucleotides in length. The complementarity between the miRNA and its complement need not be perfect, and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand, which at its 5' end, is the least involved in hydrogen bonding between the nucleotides of the different strands of the cleaved dsRNA stem, is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bonds, or G and U involving two hydrogen bonds is less strong that between G and C involving three hydrogen bonds.

Naturally occurring miRNA molecules may be comprised within their naturally occurring pre-miRNA molecules, but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA.

According to the present teachings, the dsRNA molecules may be naturally occurring or synthetic. The dsRNA can be a mixture of long and short dsRNA molecules such as, dsRNA, siRNA, siRNA+dsRNA, siRNA+miRNA, or a combination of same.

In a preferred embodiment, one or more nucleic acid agents are designed for specifically targeting a target gene of interest (e.g. a pathogen non-structural gene). It will be appreciated that the nucleic acid agent can be used to downregulate one or more target genes (e.g. as described in detail above). If a number of target genes are targeted, a heterogenic composition which comprises a plurality of nucleic acid agents for targeting a number of target genes is used. Alternatively the plurality of nucleic acid agents is separately formulated. According to a specific embodiment, a number of distinct nucleic acid agent molecules for a single target are used, which may be used separately or simultaneously (i.e., co-formulation) applied.

For example, in order to silence the expression of an mRNA of interest, synthesis of the dsRNA suitable for use with some embodiments of the invention can be selected as follows. First, the mRNA sequence is scanned including the 3' UTR and the 5' UTR. Second, the mRNA sequence is compared to an appropriate genomic database using any sequence alignment software, such as the BLAST software available from the NCBI server (wwwdotncbidotnlmdotnihdotgov/BLAST/). Putative regions in the mRNA sequence which exhibit significant homology to other coding sequences are filtered out. Qualifying target sequences are selected as templates for dsRNA synthesis. Preferred sequences are those that have as little homology to other genes in the genome to reduce an "off-target" effect.

It will be appreciated that the RNA silencing agent of some embodiments of the invention need not be limited to those molecules containing only RNA, but further encompasses chemically-modified nucleotides and non-nucleotides.

According to one embodiment, the dsRNA specifically targets a gene selected from the group consisting of SEQ ID Nos 1-5 or a variant of homolog thereof. In addition, the term AMPLICON means a piece of DNA or RNA. AN rRNA can be SEQ ID NO. 7, or a homolog thereof which include a sequence having about 80-99% homology therein.

According to a specific embodiment, the nucleic acid agent is provided to the mosquito in a configuration devoid of a heterologous promoter for driving recombinant expression of the dsRNA (exogenous), rendering the nucleic acid molecule of the instant invention a naked molecule. The nucleic acid agent may still comprise modifications that may affect its stability and bioavailability (e.g., PNA).

In certain embodiment, expression of the dsRNA molecule doesn't require a cis-acting regulatory sequence (e.g., heterologous) transcribing the dsRNA. As used herein, the term "heterologous" refers to exogenous, not-naturally occurring within a native cell of the mosquito or in a cell in which the dsRNA is fed to the larvae or mosquito (such as by position of integration, or being non-naturally found within the cell).

The nucleic acid agent can be further comprised within a nucleic acid construct comprising additional regulatory elements. For example, transcription from an expression cassette, a regulatory region (e.g., promoter, enhancer, silencer, leader, intron and polyadenylation) may be used to modulate the transcription of the RNA strand (or strands). Therefore, in one embodiment, there is provided a nucleic acid construct comprising the nucleic acid agent. The nucleic acid construct can have polynucleotide sequences constructed to facilitate transcription of the RNA molecules of the present invention operably linked to one or more promoter sequences functional in a mosquito cell. The polynucleotide sequences may be placed under the control of an endogenous promoter normally present in the mosquito genome. The polynucleotide sequences of the present invention, under the control of an operably linked promoter sequence, may further be flanked by additional sequences that advantageously effect its transcription and/or the stability of a resulting transcript. Such sequences are generally located upstream of the promoter and/or downstream of the 3' end of the expression construct. The term "operably linked," as used in reference to a regulatory sequence and a structural nucleotide sequence, means that the regulatory sequence causes regulated expression of the linked structural nucleotide sequence.

Genetic "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

It will be appreciated that the nucleic acid agents can be delivered to the mosquito and/or mosquito larva in a variety of ways. According to one embodiment, the composition of some embodiments comprises cells, which comprise the nucleic acid agent. As used herein, the term "cell" or "cells," with respect to mosquitos may refer to a mosquito cell in any stage of its lifecycle, such as a larva ingestible cell or an adult. In certain embodiment, the paratransgenic system may establish genetically modified bacteria that may be endogenous through all life cycles of the mosquito.

Specific examples of bacterial vectors include bacteria (e.g., cocci and rods), filamentous algae and detritus. Specific embodiments of transformable bacterial vectors cells that may be endogenous through all life cycles of the mosquito may include all those listed in FIG. 1. Additional embodiment may include one or more bacterial strains selected from Table 1 below. Naturally, such a list is not exclusive, and is merely exemplary of certain preferred embodiments of paratransgenic bacterial strains.

According to a specific embodiment, the cell is an algae cell. Various algae species can be used in accordance with the teachings of the invention since they are a significant part of the diet for many kinds of mosquito larvae that feed opportunistically on microorganisms as well as on small aquatic animals such as rotifers. Examples of algae that can be used in accordance with the present teachings include, but are not limited to, blue-green algae as well as green algae. Specifically, *Actinastrum hantzschii, Ankistrodesmus falcatus, Ankistrodesmus spiralis, Aphanochaete elegans, Chlamydomonas sp., Chlorella ellipsoidea, Chlorella pyrenoidosa, Chlorella variegate, Chlorococcum hypnosporum, Chodatella brevispina, Closterium acerosum, Closteriopsis acicularis, Coccochloris peniocystis, Crucigenia lauterbomii, Crucigenia tetrapedia, Coronastrum ellipsoideum, Cosmarium botrytis, Desmidium swartzii, Eudorina elegans, Gloeocystis gigas, Golenkinia minutissima, Gonium multicoccum, Nannochloris oculata, Oocystis marssonii, Oocystis minuta, Oocystis pusilla, Palmella texensis, Pandorina morum, Paulschulzia pseudovolvox, Pediastrum clathratum, Pediastrum duplex, Pediastrum simplex, Planktosphaeria gelatinosa, Polyedriopsis spinulosa, Pseudococcomyxa adhaerans, Quadrigula closterioides, Radiococcus nimbatus, Scenedesmus basiliensis, Spirogyra*

*pratensis, Staurastrum gladiosum, Tetraedron bitridens, Trochiscia hystrix. Anabaena catenula, Anabaena spiroides, Chroococcus turgidus, Cylindrospermum licheniforme, Bucapsis* sp. (U. Texas No. 1519), *Lyngbya spiralis, Microcystis aeruginosa, Nodularia spumigena, Nostoc linckia, Oscillatoria lutea, Phormidiumfaveolarum, Spinilina platensis.*

In a further embodiment, a composition including a genetically modified bacteria configured to express dsRNA may be formulated as a water dispersible granule or powder that may further be configured to be dispersed into the environment. In yet a further embodiment, the compositions of the present invention may also comprise a wettable powder, spray, emulsion, colloid, aqueous or organic solution, dust, pellet, or colloidal concentrate. Dry forms of the compositions may be formulated to dissolve immediately upon wetting, or alternatively, dissolve in a controlled-release, sustained-release, or other time-dependent manner. Alternatively or additionally, the composition may comprise an aqueous solution. Such aqueous solutions or suspensions may be provided as a concentrated stock solution which is diluted prior to application, or alternatively, as a diluted solution ready-to-apply. Such compositions may be formulated in a variety of ways. They may be employed as wettable powders, granules or dusts, by mixing with various inert materials, such as inorganic minerals (silicone or silicon derivatives, phyllosilicates, carbonates, sulfates, phosphates, and the like) or botanical materials (powdered corncobs, rice hulls, walnut shells, and the like). The formulations or compositions containing paratransgenic bacteria may include spreader-sticker adjuvants, stabilizing agents, other pesticidal additives, or surfactants. Liquid formulations may be employed as foams, suspensions, emulsifiable concentrates, or the like. The ingredients may include Theological agents, surfactants, emulsifiers, dispersants, or polymers.

As mentioned, the dsRNA of the invention may be administered as a naked dsRNA. Alternatively, the dsRNA of the invention may be conjugated to a carrier known to one of skill in the art, such as a transfection agent e.g. PEI or chitosan or a protein/lipid carrier or coupled to nanoparticles. The compositions may be formulated prior to administration in an appropriate means such as lyophilized, freeze-dried, microencapsulated, desiccated, or in an aqueous carrier, medium or suitable diluent, such as saline or other buffer. Suitable agricultural carriers can be solid, semi-solid or liquid and are well known in the art. Such compositions may be considered "agriculturally-acceptable carriers", which may covers all adjuvants, e.g., inert components, dispersants, surfactants, tackifiers, binders, etc. that are ordinarily used in pesticide formulation technology.

As mentioned, the nucleic acid agents can be delivered to the mosquito larva in various ways. Thus, administration of the composition to the mosquito larva may be carried out using any suitable or desired manual or mechanical technique for application of a composition comprising a nucleic acid agent, including, but not limited to, spraying, soaking, brushing, dressing, dripping, and coating, spreading, applying as small droplets, a mist or an aerosol. According to one embodiment, the composition is administered to the larvae by soaking or by spraying According to one embodiment, the composition is administered to the larvae by feeding. Feeding the larva with the composition can be effected for about 2 hours to 120 hours, about 2 hours to 108 hours, about 2 hours to 96 hours, about 2 hours to 84 hours, about 2 hours to 72 hours, for about 2 hours to 60 hours, about 2 hours to 48 hours, about 2 hours to 36 hours, about 2 hours to 24 hours, about 2 hours to 12 hours, 12 hours to 24 hours, about 24 hours to 36 hours, about 24 hours to 48 hours, about 36 hours to 48 hours, for about 48 hours to 60 hours, about 60 hours to 72 hours, about 72 hours to 84 hours, about 84 hours to 96 hours, about 96 hours to 108 hours, or about 108 hours to 120 hours. According to a specific embodiment, the composition is administered to the larvae by feeding for 48-96 hours or longer. Multiple feedings are regular or irregular intervals are also contemplated.

In one embodiment, nanoparticles, such as a Chitosan nanoparticle, may be used to deliver dsRNA. In this embodiment, a group of 15-20 3rd-instar mosquito larvae are transferred into a container (e.g. 500 ml glass beaker) containing 50-1000 ml, e.g. 100 ml, of deionized water. One sixth of the gel slices that are prepared from dsRNA (e.g. 32 pg of dsRNA) are added into each beaker. Approximately an equal amount of the gel slices are used to feed the larvae once a day for a total of 2-5 days, e.g. four days (see Insect Mol Biol. 2010 19(5):683-93).

Oral delivery of dsRNA: First instar larvae (less than 24 hrs old) are treated in groups of 10-100, e.g. 50, in a final volume of 25-100 pi of dsRNA, e.g. 75 pi of dsRNA, at various concentrations (ranging from 0.01 to 5 pg/pl, e.g. 0.02 to 0.5 pg/pl-dsRNAs) in tubes e.g. 2 mL microfuge tube (see J Insect Sci. 2013; 13:69). Diet containing dsRNA: larvae are fed a single concentration of 1-2000 ng dsRNA/mL, e.g. 1000 ng dsRNA/mL, diet in a diet overlay bioassay for a period of 1-10 days, e.g. 5 days (see PLoS One. 2012; 7(10): e47534.). Diet containing dsRNA: Newly emerged larvae are starved for 1-12 hours, e.g. 2 hours, and are then fed with a single drop of 0.5-10 pi, e.g. 1 pi, containing 1-20 pg, e.g. 4 pg, dsRNA (1-20 pg of dsRNA/larva, e.g. 4 pg of dsRNA/larva) (see Appl Environ Microbiol. 2013 August; 79(15):4543-50). Feeding the larva can be affected using any method known in the art. Thus, for example, the larva may be fed with agarose cubes, chitosan nanoparticles, oral delivery or diet containing dsRNA. According to one embodiment, feeding the larva with the composition is affected until the larva reaches pupa stage. Thus, according to a specific embodiment, the composition may be applied to standing water. The mosquito larva may be soaked in the water for several hours (1, 2, 3, 4, 5, 6 hours or more) to several days (1, 2, 3, 4 days or more) with or without the use of transfection reagents or dsRNA carriers.

Alternatively, the mosquito larva may be sprayed with an effective amount of the composition (e.g. via an aqueous solution). If needed, the composition may be dissolved, suspended and/or diluted in a suitable solution (as described in detail above) before use. Additionally, the nucleic acid compositions of the invention may be employed in the method of the invention singly or in combination with other compounds, including, but not limited to, inert carriers that may be natural, synthetic, organic or inorganic, humectants, feeding stimulants, attractants, encapsulating agents (for example Algae, bacteria and yeast, nanoparticles), dsRNA binding proteins, binders, emulsifiers, dyes, sugars, sugar alcohols, starches, modified starches, dispersants, or combinations thereof may also be utilized in conjunction with the composition of some embodiments of the invention.

Compositions of the invention can be used for the biocontrol of pathogen-carrying mosquitoes. Such an application comprises administering to larvae of the mosquitoes an effective amount of the composition which renders an adult stage of the mosquitoes lethally susceptible to a pathogen, thereby controlling (e.g. exterminating) the mosquitoes.

Compositions of the invention can be used for the biocontrol of pathogen-carrying mosquitoes. Such an application comprises administering to larvae of the mosquitoes, or the mosquito at any other stage in its lifecycle, an effective amount of the composition which suppresses the pathogen carried by the mosquito rendering the pathogen non-transferrable, for example to a human host. Thus, regardless of the method of application, the amount of the active component(s) are applied at an effective amount for an adult stage of the mosquito to be lethally susceptible to a pathogen, or suppress expression of a pathogen will vary depending on factors such as, for example, the specific mosquito to be controlled, the type of pathogen (bacteria, virus, protozoa, etc.), the water source to be treated, the environmental conditions, and the method, rate, and quantity of application of the composition. The concentration of the composition that is used for environmental, systemic, or foliar application will vary widely depending upon the nature of the particular formulation, means of application, environmental conditions, and degree of biocidal activity.

Exemplary concentrations of dsRNA in the composition (e.g. for soaking) include, but are not limited to, about 1 pg-10 pg of dsRNA/pl, about 1 pg-1 pg of dsRNA/pl, about 1 pg-0.1 pg of dsRNA/pl, about 1 pg-0.01 pg of dsRNA/pl, about 1 pg-0.001 pg of dsRNA/pl, about 0.001 pg-10 pg of dsRNA/pl, about 0.001 pg-5 pg of dsRNA/pl, about 0.001 pg-1 pg of dsRNA/pl, about 0.001 pg-0.1 pg of dsRNA/pl, about 0.001 pg-0.01 pg of dsRNA/pl, about 0.01 pg-10 pg of dsRNA/pl, about 0.01 pg-5 pg of dsRNA/pl, about 0.01 pg-1 pg of dsRNA/pl, about 0.01 pg-0.1 pg of dsRNA/pl, about 0.1 pg-10 pg of dsRNA/pl, about 0.1 pg-5 pg of dsRNA/pl, about 0.5 pg-5 pg of dsRNA/pl, about 0.5 pg-10 pg of dsRNA/pl, about 1 pg-5 pg of dsRNA/pl, or about 1 pg-10 pg of dsRNA/pl or more.

When formulated as a feed, the dsRNA may be effected at a dose of 1 pg/larvae-1000 pg/larvae, 1 pg/larvae-500 pg/larvae, 1 pg/larvae-100 pg/larvae, 1 pg/larvae-10 pg/larvae, 1 pg/larvae-1 pg/larvae, 1 pg/larvae-0.1 pg/larvae, 1 pg/larvae-0.01 pg/larvae, 1 pg/larvae-0.001 pg/larvae, 0.001-1000 pg/larvae, 0.001-500 pg/larvae, 0.001-100 pg/larvae, 0.001-50 pg/larvae, 0.001-10 pg/larvae, 0.001-1 pg/larvae, 0.001-0.1 pg/larvae, 0.001-0.01 pg/larvae, 0.01-1000 pg/larvae, 0.01-500 pg/larvae, 0.01-100 pg/larvae, 0.01-50 pg/larvae, 0.01-10 pg/larvae, 0.01-1 pg/larvae, 0.01-0.1 pg/larvae, 0.1-1000 pg/larvae, 0.1-500 pg/larvae, 0.1-100 pg/larvae, 0.1-50 pg/larvae, 0.1-10 pg/larvae, 0.1-1 pg/larvae, 1-1000 pg/larvae, 1-500 pg/larvae, 1-100 pg/larvae, 1-50 pg/larvae, 1-10 pg/larvae, 10-1000 pg/larvae, 10-500 pg/larvae, 10-100 pg/larvae, 10-50 pg/larvae, 50-1000 pg/larvae, 50-500 pg/larvae, 50-400 pg/larvae, 50-300 pg/larvae, 100-500 pg/larvae, 100-300 pg/larvae, 200-500 pg/larvae, 200-300 pg/larvae, or 300-500 pg/larvae or more.

According to some embodiments, the nucleic acid agent is provided in amounts effective to reduce or suppress expression of at least one mosquito pathogen resistance gene product. As used herein "a suppressive amount" or "an effective amount" or a "therapeutically effective amount" refers to an amount of dsRNA which is sufficient to downregulate (reduce expression of) the target gene by at least 20%, 30%, 40%, 50%, or more, say 60%, 70%, 80%, 90% or more even 100%.

Testing the efficacy of gene silencing can be affected using any method known in the art. For example, using quantitative RT-PCR measuring gene knockdown. Thus, for example, ten to twenty larvae from each treatment group can be collected and pooled together. RNA can be extracted therefrom and cDNA syntheses can be performed. The cDNA can then be used to assess the extent of RNAi, by measuring levels of gene expression using qRT-PCR. Reagents of the present invention can be packed in a kit including the nucleic acid agent (e.g. dsRNA), instructions for administration of the nucleic acid agent, construct or composition to mosquito larva.

As used herein, the term "gene" or "polynucleotide" refers to a single nucleotide or a polymer of nucleic acid residues of any length. The polynucleotide may contain deoxyribonucleotides, ribonucleotides, and/or their analogs, and may be double-stranded or single stranded. A polynucleotide can comprise modified nucleic acids (e.g., methylated), nucleic acid analogs or non-naturally occurring nucleic acids and can be interrupted by non-nucleic acid residues. For example, a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition, are nucleic acid polymers that have been modified, whether naturally or by intervention.

Constructs of the invention may be prepared by any method known in the art for the synthesis of DNA and RNA molecules, including techniques for chemically synthesizing oligodeoxyribonucleotides and oligoribonucleotides well known in the art, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

As used herein the terms "approximately" or "about" refer to ±10%. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references, unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, "endosymbiotic" or "endosymbionts" generally refers to a bacteria that is an endosymbiot of a mosquito. It may also include bacteria that persist throughout the life-cycle of a mosquito. An endosymbiotic bacteria includes enteric bacteria identified in FIG. 2, Table 1 entitled Exemplary Paratransgenic Bacterial Strains, *E. Coli* strain JC8031 and other strains identified herein.

TABLE 1

Exemplary Paratransgenic Bacterial Strains.

| STRAIN | CHARACTERISTICS |
|---|---|
| HT115 | E. coli RNase III deficient strain suitable for production of dsRNA. Used in many studies for trans-kingdom delivery of dsRNA. |
| HT27 | E. coli RNase III deficient strain suitable for production of dsRNA. It also has two auxotrophies (histidine and isoleucine). Autotrophy has been shown to enhance nanotube formation with other bacteria[1]. These nanotubes facilitate transfer of biomaterial (proteins, nucleic acids). May be used in certain embodiments as an enhanced delivery bacterial strain. |
| JC8031 | E. coli with enhanced hyper-vesiculation activity. |
| Pantoea Ae16 | Mosquito enteric bacteria identified by present inventors. May be further genetically engineered to create RNase III deficiency. |
| Serratia AeS1 | Mosquito enteric bacteria identified by the present inventors that persist through all mosquito developmental stages. May be further genetically engineered to create RNase III deficiency. |
| Serratia MS5 | Mosquito enteric bacteria identified by present inventors that persist through all mosquito developmental stages. May be further genetically engineered to create RNase III deficiency. |
| Pseudomonas putida Ae076 | Endosymbiotic bacteria in mosquito |
| Pseudomonas putida Ae142 | Endosymbiotic bacteria in mosquito |
| Pseudomonas putida Ae171 | Endosymbiotic bacteria in mosquito |
| All strains identified in FIG. 2 | Endosymbiotic bacteria in mosquito |
| All strains identified in Table 7 | Endemic in mosquito |

TABLE 2

Helper Genes.

| HELPER GENE(S) | CHARACTERISTICS |
|---|---|
| VrrA | Small non-coding RNA that upon binding to OmpA mRNA increases bacterial hyper-vesiculation activity. Identified as (SEQ ID NO. 7) |
| SID1 | dsRNA-specific transporter that facilitates systemic RNAi. |
| SID2 | Membrane protein that is required for uptake of ingested dsRNA, |
| Ago2 | Member of Argonaute family that is specific to provide defense against RNA viruses. |
| YmdB | Bacterial regulatory protein that suppresses RNase III cleavage. Currently in use to suppress RNase III in mosquito enteric bacteria. |
| dsRNA-binding proteins | Staufen and RDE-4 proteins can bind dsRNA. Co-expression of these proteins and dsRNA in bacteria can enhance the lifetime of the produced dsRNA and facilitate their transport in mosquito cells. |
| HlyA | Use of Hemolysin A transport signal to enhance secretion of dsRNA-binding proteins. |
| Sec-secretory signal peptides and Tat-secretory signal peptides | Use of Sec and Tat signaling peptides to enhance secretion of dsRNA-binding proteins. |
| Cell-penetrating peptides (CPPs) | Use of CPPs such as Tat and Antennapedia or similar peptides to enhance uptake of dsRNA-binding proteins in mosquito cells. May be combined with secretory peptides. |

TABLE 3

Zika Virus target genes.

| Gene ID | CHARACTERISTICS |
|---|---|
| C | Capsid |
| prM | Precursor membrane |
| E | E protein composes the majority of the virion surface and is involved with aspects of replication such as host cell binding and membrane fusion. |
| NS1 | Non-structural protein |
| NS2A | Non-structural protein. Possibly involved in translation, RNA packaging, cyclization, genome stabilization, and recognition. |
| NS2B | Non-structural protein. Possibly involved in translation, RNA packaging, cyclization, genome stabilization, and recognition. |
| NS3 | Non-structural protein. |
| C | Non-structural protein. |
| NS4A | Non-structural protein. Possibly involved in translation, RNA packaging, cyclization, genome stabilization, and recognition. |
| NS4B | Non-structural protein. Possibly involved in translation, RNA packaging, cyclization, genome stabilization, and recognition. |
| NS | Non-structural protein. |

As an exemplary model, the Zika genome comprises: 5'-C-prM-E-NS1-NS2A-NS2B-NS3-NS4A-NS4B-NS5-3' and codes for a polyprotein that is subsequently cleaved into capsid (C), precursor membrane (prM), envelope (E), and non-structural proteins (NS).

TABLE 15

Sequence Identification of dsRNA from ZIKV genome regions 1-5.

SEQ. ID. No. 1 (DsRNA1)
CCCCCTAGCGAAGTACTCACAGCTGTTGGCCTGATATGCGCATTGGCTG
GAGGGTTCGCCAAGGCAGATATAGAGATGGCTGGGCCCATGGCCGCGGT
CGGTCTGCTAATTGTCAGTTACGTGGTCTCAGGAAAGAGTGTGGACATG
TACATTGAAAGAGCAGGTGACATCACATGGGAAAAAGATGCGGAAGTCA
CTGGAAACAGTCCCCGGCTCGATGTGGCGCTAGATGAGAGTGGTGATTT
CTCCCTGGTGGAGGATGACGGTCCCCCCATGAGAGAGATCATACTCAAG
GTGGTCCTGATGACCATCTGTGGCATGAACCCAATAGCCATACCCTTTG
CAGCTGGAGCGTGGTACGTATACGTGAAGACTGGAAAAAGGAGTGGTGC
TCTATGGGATGTGCCTGCTCCCAAGGAAGTAAAAAAGGGGGAGACCACA
GATGGAGTGTACAGAGTAATGACTCGTAGACTGCTAGGTTCAACACAAG
TTGGAGTGGGAGTTATGCAAGAGGGGGTCTTTCACACTATGTCCTCTGA
ACTAGGTATGAC

SEQ. ID. No. 2 (DsRNA2)
GCGGTGAAGGGAGACTTGATCCATACTGGGGAGATGTCAAGCAGGATCT
GGTGTCATACTGTGGTCCATGGAAGCTAGATGCCGCCTGGGATGGGCAC
AGCGAGGTGCAGCTCTTGGCCGTGCCCCCCGGAGAGAGAGCGAGGAACA
TCCAGACTCTGCCCGGAATATTTAAGACAAAGGATGGGGACATTGGAGC
GGTTGCGCTGGATTACCCAGCAGGAACTTCAGGATCTCCAATCCTAGAC
AAGTGTGGGAGAGTGATAGGACTTTATGGCAATGGGGTCGTGATCAAAA
ACGGGAGTTATGTTAGTGCCATCACCCAAGGGAGGAGGGAGGAAGAGAC
TCCTGTTGAGTGCTTCGAGCCCTCGATGCTGAAGAAGAAGCAGCTAACT

SEQ. ID. No. 3 (DsRNA3)
CTGCTGAAATGGAGGAGGCCCTTAGAGGGCTTCCAGTGCGTTATATGAC
AACAGCAGTCAATGTCACCCACTCTGGAACAGAAATCGTCGACTTAATG
TGCCATGCCACCTTCACTTCACGTCTACTACAGCCAATCAGAGTCCCCA
ACTATAATCTGTATATTATGGATGAGGCCCACTTCACAGATCCCTCAAG
TATAGCAGCAAGAGGATACATTTCAACAAGGGTTGAGATGGGCGAGGCG
GCTGCCATCTTCATGACCGCCACGCCACCAGGAACCCGTGACGCATTTC
CGGACTCCAACTCACCAATTATGGACACCGAAGTGGAAGTCCCAGAGAG
AGCCTGGAGCTCAGGCTTTGATTGGGTGACGGATCATTCTGGAAAAACA
GTTTGGTTTGTTCCAAGCGTGAGGAACGGCAATGAGATCGCAGCTTGTC
TGACAAAGGCTGGAAAACGGGTCATACAGCTCAGCAGAAAGACTTTTGA
GACAGAGTTCCAGAAAACAAAACATCAAGAGTGGGACTTTGTCGTGACA
ACTGACATTTC

SEQ. ID. No. 4 (DsRNA4)
AGAGATGGGCGCCAACTTTAAAGCTGACCGTGTCATAGATTCCAGGAGA
TGCCTAAAGCCGGTCATACTTGATGGCGAGAGAGTCATTCTGGCTGGAC
CCATGCCTGTCACACATGCCAGCGCTGCCCAGAGGAGGGGGCGCATAGG
CAGGAATCCCAACAAACCTGGAGATGAGTATCTGTATGGAGGTGGGTGC
GCAGAGACTGACGAAGACCATGCACACTGGCTTGAAGCAAGAATGCTCC
TTGACAATATTTACCTCCAAGATGGCCTCATAGCCTCGCTCTATCGACC
TGAGGCCGACAAAGTAGCAGCCATTGAGGGAGAGTTCAAGCTTAGGACG
GAGCAAAGGAAGACCTTTGTGGAACTCATGAAAAGAGGAGATCTTCCTG
TTTGGCTGGCCTATCAGGTTGCATCTGCCGGAATAACCTACACAGATAG
AAGATGGTGCTT

SEQ. ID. No. 5 (DsRNA5)
CGACCAACAACACCATAATGGAAGACAGTGTGCCGGCAGAGGTGTGGAC
CAGACACGGAGAGAAAAGAGTGCTCAAACCGAGGTGGATGGACGCCAGA
GTTTGTTCAGATCATGCGGCCCTGAAGTCATTCAAGGAGTTTGCCGCTG
GGAAAAGAGGAGCGGCTTTTGGAGTGATGGAAGCCCTGGGAACACTGCC
AGGACACATGACAGAGAGATTCCAGGAAGCCATTGACAACCTCGCTGTG
CTCATGCGGGCAGAGACTGGAAGCAGGCCTTACAAAGCCGCGGCGGCCC
AATTGCCGGAGACCCTAGAGACCATAATGCTTTTGGGGTTGCTGGGAAC
AGTCTCGCTGGGAATCTTCTTCGTCTTGATGAGGAACAAGGGCATAGGG
AAGATGGGCTTTGGAATGGTGACTCTTGGGGCCAGCGCATGGCTCATGT
GGCTCTCGGAAATTGAGCCAGCCAGAATTGCATGTGTCCTCATTGTTGT
GTTCCTATTGCTGGTGGTGCTCATACCTGAGCCAGAAAAGCAAAGATC

SEQ. ID. No. 7 (sRNA) (*Vibrio cholera*)
GTGATTGACAGAGCTTTGAGAGTTTTACTGGCCGTCAAATTTGGTTCTC
GACCCGCTGTCACCAATTACGCTGCTTTTTCCTTTTTATTAACTCCTAT
ACTTGTGTACGCCCAAAGCCAGATTGTTTTGGGCGTTTTTTATCTGGT
TT

Sequence Identification of dsRNA from ZIKV genome regions 1-5.

GTCTTAGACTTGCATCCTGGAGCTGGGAAAACCAGGAGAGTTCTTCCTG
AAATAGTCCGTGAAGCCATAAAAACAAGACTCCGTACTGTGATCTTAGC
TCCAACCAGGGTTGTCG

TABLE 15 Complete Zika Virus Genome Sequence Showing 5 Amplicons in Genes NS2B, NS3, and NS4A that were Used for Transcription of dsRNA KU501215.1 Zika virus strain PRVABC59, complete RNA genome sequence (SEQ ID No. 6). The beginning of each gene is marked in purple. Since genes are contiguous, the beginning of one gene marks the end of the previous gene. Amplicons 1-5, which serve as templates for dsRNA transcription, are marked in five colors and begin with the forward primer and end with the reverse primer.

Amplicon 1 generally referred to as SEQ ID No. 1

Amplicon 2 generally referred to as SEQ ID No. 2

Amplicon 3 generally referred to as SEQ ID No. 3

-continued

Amplicon 4 generally referred to as SEQ ID No. 4

Amplicon 5 generally referred to as SEQ ID No. 5

```
5'UTR
GTTGTTGATCTGTGTGAATCAGACTGCGACAGTTCGAGTTTGAAGCGAAAGCTAGCAACAGTATCAACAG

C capsid
                                                M  K  N  P  K  K  K  S  G  G  F  R
GTTTTATTTTGGATTTGGAAACGAGAGTTTCTGGTCATGAAAAACCCAAAAAAGAAATCCGGAGGATTCC I  V  N  M  L  K  R  G  V  A  R  V  S  P  F  G  G  L  K  R  L  P  A
GGATTGTCAATATGCTAAAACGCGGAGTAGCCCGTGTGAGCCCCTTTGGGGGCTTGAAGAGGCTGCCAGC G  L  L  L  G  H  G  P  I  R  M  V  L  A  I  L  A  F  L  R  F  T  A
CGGACTTCTGCTGGGTCATGGGCCCATCAGGATGGTCTTGGCGATTCTAGCCTTTTTGAGATTCACGGCA I  K  P  S  L  G  L  I  N R W  G  S  V  G  K  K  E  A  M  E  T  I  K
ATCAAGCCATCACTGGGTCTCATCAATAGATGGGGTTCAGTGGGGAAAAAAGAGGCTATGGAAACAATAA K  F  K  K  D  L  A  A  M  L  R  I  I  N  A  R  K  E  K  K  R  R  G
AGAAGTTCAAGAAAGATCTGGCTGCCATGCTGAGAATAATCAATGCTAGGAAGGAGAAGAAGAGACGAGG preM
 A  D  T  S  V  G  I  V  G  L  L  L  T  T  A  M  A  A  E  V  T  R  R
CGCAGATACTAGTGTCGGAATTGTTGGCCTCCTGCTGACCACAGCTATGGCAGCGGAGGTCACTAGACGT G  S  A  Y  Y  M  Y  L  D  R  N  D  A  G  E  A  I  S  F  P  T  T  L  G
GGGAGTGCATACTATATGTACTTGGACAGAAACGATGCTGGGGAGGCCATATCTTTTCCAACCACATTGG M  N  K  C  Y  I  Q  I  M  D  L  G  H  M  C  D  A  T  M  S  Y  E  C
GGATGAATAAGTGTTATATACAGATCATGGATCTTGGACACATGTGTGATGCCACCATGAGCTATGAATG P  M  L  D  E  G  V  E  P  D  D  V  D  C  W  C  N  T  T  S  T  W  V
CCCTATGCTGGATGAGGGGGTGGAACCAGATGACGTCGATTGTTGGTGCAACACGACGTCAACTTGGGTT glycoprotein  M
V  Y  G  T  C  H  H  K  K  G  E  A  R  R  S  R  R  A  V  T  L  P  S  H
GTGTACGGAACCTGCCATCACAAAAAAGGTGAAGCACGGAGATCTAGAAGAGCTGTGACGCTCCCCTCCC S  T  R  K  L  Q  T  R  S  Q  T  W  L  E  S  R  E  Y  T  K  H  L  I
ATTCCACCAGGAAGCTGCAAACGCGGTCGCAAACCTGGTTGGAATCAAGAGAATACACAAAGCACTTGAT R  V  E  N  W  I  F  R  N  P  G  F  A  L  A  A  A  A  I  A  W  L  L
TAGAGTCGAAAATTGGATATTCAGGAACCCTGGCTTCGCGTTAGCAGCAGCTGCCATCGCTTGGCTTTTG Envelope glycoprotein E
G  S  S  T  S  Q  K  V  I  Y  L  V  M  I  L  L  I  A  P  A  Y  S  I  R
GGAAGCTCAACGAGCCAAAAAGTCATATACTTGGTCATGATACTGCTGATTGCCCCGGCATACAGCATCA C  I  G  V  S  N  R  D  F  V  E  G  M  S  G  G  T  W  V  D  V  V  L
GGTGCATAGGAGTCAGCAATAGGGACTTTGTGGAAGGTATGTCAGGTGGGACTTGGGTTGATGTTGTCTT E  H  G  G  C  V  T  V  M  A  Q  D  K  P  T  V  D  I  E  L  V  T  T
GGAACATGGAGGTTGTGTCACCGTAATGGCACAGGACAAACCGACTGTCGACATAGAGCTGGTTACAACA T  V  S  N  M  A  E  V  R  S  Y  C  Y  E  A  S  I  S  D  M  A  S  D  S
ACAGTCAGCAACATGGCGGAGGTAAGATCCTACTGCTATGAGGCATCAATATCAGACATGGCTTCTGACA R  C  P  T  Q  G  E  A  Y  L  D  K  Q  S  D  T  Q  Y  V  C  K  R  T
GCCGCTGCCCAACACAAGGTGAAGCCTACCTTGACAAGCAATCAGACACTCAATATGTCTGCAAAAGAAC L  V  D  R  G  W  G  N  G  C  G  L  F  G  K  G  S  L  V  T  C  A  K
GTTAGTGGACAGAGGCTGGGGAAATGGATGTGGACTTTTTGGCAAAGGGAGCCTGGTGACATGCGCTAAG F  A  C  S  K  K  M  T  G  K  S  I  Q  P  E  N  L  E  Y  R  I  M  L  S
TTTGCATGCTCCAAGAAAATGACCGGGAAGAGCATCCAGCCAGAGAATCTGGAGTACCGGATAATGCTGT V  H  G  S  Q  H  S  G  M  I  V  N  D  T  G  H  E  T  D  E  N  R  A
CAGTTCATGGCTCCCAGCACAGTGGGATGATCGTTAATGACACAGGACATGAAACTGATGAGAATAGAGC K  V  E  I  T  P  N  S  P  R  A  E  A  T  L  G  G  F  G  S  L  G  L
GAAAGTTGAGATAACGCCCAATTCACCGAGAGCCGAAGCCACCCTGGGGGGTTTTGGAAGCCTAGGACTT D  C  E  P  R  T  G  L  D  F  S  D  L  Y  Y  L  T  M  N  N  K  H  W  L
GATTGTGAACCGAGGACAGGCCTTGACTTTTCAGATTTGTATTACTTGACTATGAATAACAAGCACTGGT V  H  K  E  W  F  H  D  I  P  L  P  W  H  A  G  A  D  T  G  T  P  H
TGGTTCACAAGGAGTGGTTCCACGACATTCCATTACCTTGGCACGCTGGGGCAGACACCGGAACTCCACA
```

```
       W  N  N  K  E  A  L  V  E  F  K  D  A  H  A  K  R  Q  T  V  V  V  L
     CTGGAACAACAAAGAAGCACTGGTAGAGTTCAAGGACGCACATGCCAAAAGGCAAACTGTCGTGGTTCTA

G  S  Q  E  G  A  V  H  T  A  L  A  G  A  L  E  A  E  M  D  G  A  K  G
     GGGAGTCAAGAAGGAGCAGTTCACACGGCCCTTGCTGGAGCTCTGGAGGCTGAGATGGATGGTGCAAAGG

R  L  S  S  G  H  L  K  C  R  L  K  M  D  K  L  R  L  K  G  V  S  Y
     GAAGGCTGTCCTCTGGCCACTTGAAATGTCGCCTGAAAATGGATAAACTTAGATTGAAGGGCGTGTCATA

S  L  C  T  A  A  F  T  F  T  K  I  P  A  E  T  L  H  G  T  V  T  V
     CTCCTTGTGTACTGCAGCGTTCACATTCACCAAGATCCCGGCTGAAACACTGCACGGGACAGTCACAGTG

E  V  Q  Y  A  G  T  D  G  P  C  K  V  P  A  Q  M  A  V  D  M  Q  T  L
     GAGGTACAGTACGCAGGGACAGATGGACCTTGCAAGGTTCCAGCTCAGATGGCGGTGGACATGCAAACTC

T  P  V  G  R  L  I  T  A  N  P  V  I  T  E  S  T  E  N  S  K  M  M
     TGACCCCAGTTGGGAGGTTGATAACCGCTAACCCCGTAATCACTGAAAGCACTGAGAACTCTAAGATGAT

L  E  L  D  P  P  F  G  D  S  Y  I  V  I  G  V  G  E  K  K  I  T  H
     GCTGGAACTTGATCCACCATTTGGGGACTCTTACATTGTCATAGGAGTCGGGGAGAAGAAGATCACCCAC

H  W  H  R  S  G  S  T  I  G  K  A  F  E  A  T  V  R  G  A  K  R  M  A
     CACTGGCACAGGAGTGGCAGCACCATTGGAAAAGCATTTGAAGCCACTGTGAGAGGTGCCAAGAGAATGG

V  L  G  D  T  A  W  D  F  G  S  V  G  G  A  L  N  S  L  G  K  G  I
     CAGTCTTGGGAGACACAGCCTGGGACTTTGGATCAGTTGGAGGCGCTCTCAACTCATTGGGCAAGGGCAT

H  Q  I  F  G  A  A  F  K  S  L  F  G  G  M  S  W  F  S  Q  I  L  I
     CCATCAAATTTTTGGAGCAGCTTTCAAATCATTGTTTGGAGGAATGTCCTGGTTCTCACAAATTCTCATT

G  T  L  L  M  W  L  G  L  N  T  K  N  G  S  I  S  L  M  C  L  A  L  G
     GGAACGTTGCTGATGTGGTTGGGTCTGAACACAAAGAATGGATCTATTTCCCTTATGTGCTTGGCCTTAG
                                          NS1
        G  V  L  I  F  L  S  T  A  V  S  A  D  V  G  C  S  V  D  F  S  K  K
     GGGGAGTGTTGATCTTCTTATCCACAGCCGTCTCTGCTGATGTGGGGTGCTCGGTGGACTTCTCAAAGAA

E  T  R  C  G  T  G  V  F  V  Y  N  D  V  E  A  W  R  D  R  Y  K  Y
     GGAGACGAGATGCGGTACAGGGGTGTTCGTCTATAACGACGTTGAAGCCTGGAGGGACAGGTACAAGTAC

H  P  D  S  P  R  R  L  A  A  A  V  K  Q  A  W  E  D  G  I  C  G  I  S
     CATCCTGACTCCCCCCGTAGATTGGCAGCAGCAGTCAAGCAAGCCTGGGAAGATGGTATCTGCGGGATCT

S  V  S  R  M  E  N  I  M  W  R  S  V  E  G  E  L  N  A  I  L  E  E
     CCTCTGTTTCAAGAATGGAAAACATCATGTGGAGATCAGTAGAAGGGGAGCTCAACGCAATCCTGGAAGA

N  G  V  Q  L  T  V  V  V  G  S  V  K  N  P  M  W  R  G  P  Q  R  L
     GAATGGAGTTCAACTGACGGTCGTTGTGGGATCTGTAAAAAACCCCATGTGGAGAGGTCCACAGAGATTG

P  V  P  V  N  E  L  P  H  G  W  K  A  W  G  K  S  Y  F  V  R  A  A  K
     CCCGTGCCTGTGAACGAGCTGCCCCACGGCTGGAAGGCTTGGGGGAAATCGTATTTCGTCAGAGCAGCAA

T  N  N  S  F  V  V  D  G  D  T  L  K  E  C  P  L  K  H  R  A  W  N
     AGACAAATAACAGCTTTGTCGTGGATGGTGACACACTGAAGGAATGCCCACTCAAACATAGAGCATGGAA

S  F  L  V  E  D  H  G  F  G  V  F  H  T  S  V  W  L  K  V  R  E  D
     CAGCTTTCTTGTGGAGGATCATGGGTTCGGGGTATTTCACACTAGTGTCTGGCTCAAGGTTAGAGAAGAT

Y  S  L  E  C  D  P  A  V  I  G  T  A  V  K  G  K  E  A  V  H  S  D  L
     TATTCATTAGAGTGTGATCCAGCCGTTATTGGAACAGCTGTTAAGGGAAAGGAGGCTGTACACAGTGATC

G  Y  W  I  E  S  E  K  N  D  T  W  R  L  K  R  A  H  L  I  E  M  K
     TAGGCTACTGGATTGAGAGTGAGAAGAATGACACATGGAGGCTGAAGAGGGCCCATCTGATCGAGATGAA

T  C  E  W  P  K  S  H  T  L  W  T  D  G  I  E  E  S  D  L  I  I  P
     AACATGTGAATGGCCAAAGTCCCACACATTGTGGACAGATGGAATAGAAGAGAGTGATCTGATCATACCC

K  S  L  A  G  P  L  S  H  H  N  T  R  E  G  Y  R  T  Q  M  K  G  P  W
     AAGTCTTTAGCTGGGCCACTCAGCCATCACAATACCAGAGAGGGCTACAGGACCCAAATGAAAGGGCCAT

H  S  E  E  L  E  I  R  F  E  E  C  P  G  T  K  V  H  V  E  E  T  C
     GGCACAGTGAAGAGCTTGAAATTCGGTTTGAGGAATGCCCAGGCACTAAGGTCCACGTGGAGGAAACATG

G  T  R  G  P  S  L  R  S  T  T  A  S  G  R  V  I  E  E  W  C  C  R
     TGGAACAAGAGGACCATCTCTGAGATCAACCACTGCAAGCGGAAGGGTGATCGAGGAATGGTGCTGCAGG
```

```
  E  C  T  M  P  P  L  S  F  R  A  K  D  G  C  W  Y  G  M  E  I  R  P  R
GAGTGCACAATGCCCCACTGTCGTTCCGGGCTAAAGATGGCTGTTGGTATGGAATGGAGATAAGGCCCA

K  E  P  E  S  N  L  V  R  S  M  V  T  A  G  S  T  D  H  M  D  H  F
GGAAAGAACCAGAAAGCAACTTAGTAAGGTCAATGGTGACTGCAGGATCAACTGATCACATGGACCACTT

NS2A
  S  L  G  V  L  V  I  L  L  M  V  Q  E  G  L  K  K  R  M  T  T  K  I
CTCCCTTGGAGTGCTTGTGATCCTGCTCATGGTGCAGGAAGGGCTGAAGAAGAGAATGACCACAAAGATC

I  I  S  T  S  M  A  V  L  V  A  M  I  L  G  G  F  S  M  S  D  L  A  K
ATCATAAGCACATCAATGGCAGTGCTGGTAGCTATGATCCTGGGAGGATTTTCAATGAGTGACCTGGCTA

L  A  I  L  M  G  A  T  F  A  E  M  N  T  G  G  D  V  A  H  L  A  L
AGCTTGCAATTTTGATGGGTGCCACCTTCGCGGAAATGAACACTGGAGGAGATGTAGCTCATCTGGCGCT

I  A  A  F  K  V  R  P  A  L  L  V  S  F  I  F  R  A  N  W  T  P  R
GATAGCGGCATTCAAAGTCAGACCAGCGTTGCTGGTATCTTTCATCTTCAGAGCTAATTGGACACCCCGT

E  S  M  L  L  A  L  A  S  C  L  L  Q  T  A  I  S  A  L  E  G  D  L  M
GAAAGCATGCTGCTGGCCTTGGCCTCGTGTCTTTTGCAAACTGCGATCTCCGCCTTGGAAGGCGACCTGA

V  L  I  N  G  F  A  L  A  W  L  A  I  R  A  M  V  V  P  R  T  D  N
TGGTTCTCATCAATGGTTTTGCTTTGGCCTGGTTGGCAATACGAGCGATGGTTGTTCCACGCACTGATAA

I  T  L  A  I  L  A  A  L  T  P  L  A  R  G  T  L  L  V  A  W  R  A
CATCACCTTGGCAATCCTGGCTGCTCTGACACCACTGGCCCGGGGCACACTGCTTGTGGCGTGGAGAGCA

G  L  A  T  C  G  G  F  M  L  L  S  L  K  G  K  G  S  V  K  K  N  L  P
GGCCTTGCTACTTGCGGGGGGTTTATGCTCCTCTCTCTGAAGGGAAAAGGCAGTGTGAAGAAGAACTTAC

F  V  M  A  L  G  L  T  A  V  R  L  V  D  P  I  N  V  V  G  L  L  L
CATTTGTCATGGCCCTGGGACTAACCGCTGTGAGGCTGGTCGACCCCATCAACGTGGTGGGACTGCTGTT

NS2B
    L  T  R  S  G  K  R  S  W  P  P  S  E  V  L  T  A  V  G  L  I  C  A
GCTCACAAGGAGTGGGAAGCGGAGCTGGCCCCCTAGCGAAGTACTCACAGCTGTTGGCCTGATATGCGCA

┌───────────┐
                            │ Amplicon 1│
                            └───────────┘

Amp1f 7F-T7-CCCCCTAGCGAAGTACT>

L  A  G  G  F  A  K  A  D  I  E  M  A  G  P  M  A  A  V  G  L  L  I  V
TTGGCTGGAGGGTTCGCCAAGGCAGATATAGAGATGGCTGGGCCCATGGCCGCGGTCGGTCTGCTAATTG

S  Y  V  V  S  G  K  S  V  D  M  Y  I  E  R  A  G  D  I  T  W  E  K
TCAGTTACGTGGTCTCAGGAAAGAGTGTGGACATGTACATTGAAAGAGCAGGTGACATCACATGGGAAAA

D  A  E  V  T  G  N  S  P  R  L  D  V  A  L  D  E  S  G  D  F  S  L
AGATGCGGAAGTCACTGGAAACAGTCCCCGGCTCGATGTGGCGCTAGATGAGAGTGGTGATTTCTCCCTG

V  E  D  D  G  P  P  M  R  E  I  I  L  K  V  V  L  M  T  I  C  G  M  N
GTGGAGGATGACGGTCCCCCCATGAGAGAGATCATACTCAAGGTGGTCCTGATGACCATCTGTGGCATGA

P  I  A  I  P  F  A  A  G  A  W  Y  V  V  Y  V  K  T  G  K  R  S  G  A
ACCCAATAGCCATACCCTTTGCAGCTGGAGCGTGGTACGTATACGTGAAGACTGGAAAAAGGAGTGGTGC

NS3
  L  W  D  V  P  A  P  K  E  V  K  K  G  E  T  T  D  G  V  Y  R  V  M
TCTATGGGATGTGCCTGCTCCCAAGGAAGTAAAAAAGGGGGAGACCACAGATGGAGTGTACAGAGTAATG

T  R  R  L  L  G  S  T  Q  V  G  V  G  V  M  Q  E  G  V  F  H  T  M  W
ACTCGTAGACTGCTAGGTTCAACACAAGTTGGAGTGGGAGTTATGCAAGAGGGGGTCTTTCACACTATGT

┌───────────┐
                            │ Amplicon 2│
                            └───────────┘

Amp2f 569 F-T7 GCGGTGAAGGGAGACT>

<CCTCTGAACTAGGTATGAC 596RT7Amp1r
     H  V  T  K  G  S  A  L  R  S  G  E  G  R  L  D  P  Y  W  G  D  V  K
GGCACGTCACAAAAGGATCCGCGCTGAGAAGCGGTGAAGGGAGACTTGATCCATACTGGGGAGATGTCAA

Q  D  L  V  S  Y  C  G  P  W  K  L  D  A  A  W  D  G  H  S  E  V  Q
GCAGGATCTGGTGTCATACTGTGGTCCATGGAAGCTAGATGCCGCCTGGGATGGGCACAGCGAGGTGCAG
```

```
L  L  A  V  P  P  G  E  R  A  R  N  I  Q  T  L  P  G  I  F  K  T  K  D
CTCTTGGCCGTGCCCCCCGGAGAGAGAGCGAGGAACATCCAGACTCTGCCCGGAATATTTAAGACAAAGG

G  D  I  G  A  V  A  L  D  Y  P  A  G  T  S  G  S  P  I  L  D  K  C
ATGGGGACATTGGAGCGGTTGCGCTGGATTACCCAGCAGGAACTTCAGGATCTCCAATCCTAGACAAGTG

G  R  V  I  G  L  Y  G  N  G  V  V  I  K  N  G  S  Y  V  S  A  I  T
TGGGAGAGTGATAGGACTTTATGGCAATGGGGTCGTGATCAAAAACGGGAGTTATGTTAGTGCCATCACC

Q  G  R  R  E  E  E  T  P  V  E  C  F  E  P  S  M  L  K  K  K  Q  L  T
CAAGGGAGGAGGGAGGAAGAGACTCCTGTTGAGTGCTTCGAGCCCTCGATGCTGAAGAAGAAGCAGCTAA

V  L  D  L  H  P  G  A  G  K  T  R  R  V  L  P  E  I  V  R  E  A  I
CTGTCTTAGACTTGCATCCTGGAGCTGGGAAAACCAGGAGAGTTCTTCCTGAAATAGTCCGTGAAGCCAT

K  T  R  L  R  T  V  I  L  A  P  T  R  V  V  A  A  E  M  E  E  A  L
```

[Amplicon 3]

```
                 Amp3f1,076 F-T7CTGCTGAAATGGAGGAGG>
AAAAACAAGACTCCGTACTGTGATCTTAGCTCCAACCAGGGTTGTCGCTGCTGAAATGGAGGAGGCCCTT

R  G  L  P  V  R  Y  M  T  T  A  V  N  V  T  H  S  G  T  E  I  V  D  L
AGAGGGCTTCCAGTGCGTTATATGACAACAGCAGTCAATGTCACCCACTCTGGAACAGAAATCGTCGACT

<AGGTCACGCAATATACTGTT 1,126 R-T7 Amp2r
  M  C  H  A  T  F  T  S  R  L  L  Q  P  I  R  V  P  N  Y  N  L  Y  I
TAATGTGCCATGCCACCTTCACTTCACGTCTACTACAGCCAATCAGAGTCCCCAACTATAATCTGTATAT

M  D  E  A  H  F  T  D  P  S  S  I  A  A  R  G  Y  I  S  T  R  V  E
TATGGATGAGGCCCACTTCACAGATCCCTCAAGTATAGCAGCAAGAGGATACATTTCAACAAGGGTTGAG

M  G  E  A  A  A  I  F  M  T  A  T  P  P  G  T  R  D  A  F  P  D  S  N
ATGGGCGAGGCGGCTGCCATCTTCATGACCGCCACGCCACCAGGAACCCGTGACGCATTTCCGGACTCCA

S  P  I  M  D  T  E  V  E  V  P  E  R  A  W  S  S  G  F  D  W  V  T
ACTCACCAATTATGGACACCGAAGTGGAAGTCCCAGAGAGAGCCTGGAGCTCAGGCTTTGATTGGGTGAC

D  H  S  G  K  T  V  W  F  V  P  S  V  R  N  G  N  E  I  A  A  C  L
GGATCATTCTGGAAAAACAGTTTGGTTTGTTCCAAGCGTGAGGAACGGCAATGAGATCGCAGCTTGTCTG

T  K  A  G  K  R  V  I  Q  L  S  R  K  T  F  E  T  E  F  Q  K  T  K  H
ACAAAGGCTGGAAAACGGGTCATACAGCTCAGCAGAAAGACTTTTGAGACAGAGTTCCAGAAAACAAAAC
```

[Amplicon 4]

```
Amp4f 1,589 F-T7
ATCAAGAGTGGGACTTTGTC>
   Q  E  W  D  F  V  V  T  T  D  I  S  E  M  G  A  N  F  K  A  D  R  V
ATCAAGAGTGGGACTTTGTCGTGACAACTGACATTTCAGAGATGGGCGCCAACTTTAAAGCTGACCGTGT

<CAGCACTGTTGACTGTAAAG 1,625 R-T7 Amp3r
  I  D  S  R  R  C  L  K  P  V  I  L  D  G  E  R  V  I  L  A  G  P  M
CATAGATTCCAGGAGATGCCTAAAGCCGGTCATACTTGATGGCGAGAGAGTCATTCTGGCTGGACCCATG

P  V  T  H  A  S  A  A  Q  R  R  G  R  I  G  R  N  P  N  K  P  G  D  E
CCTGTCACACATGCCAGCGCTGCCCAGAGGAGGGGGCGCATAGGCAGGAATCCCAACAAACCTGGAGATG

Y  L  Y  G  G  G  C  A  E  T  D  E  D  H  A  H  W  L  E  A  R  M  L
AGTATCTGTATGGAGGTGGGTGCGCAGAGACTGACGAAGACCATGCACACTGGCTTGAAGCAAGAATGCT

L  D  N  I  Y  L  Q  D  G  L  I  A  S  L  Y  R  P  E  A  D  K  V  A
CCTTGACAATATTTACCTCCAAGATGGCCTCATAGCCTCGCTCTATCGACCTGAGGCCGACAAAGTAGCA

A  I  E  G  E  F  K  L  R  T  E  Q  R  K  T  F  V  E  L  M  K  R  G  D
GCCATTGAGGGAGAGTTCAAGCTTAGGACGGAGCAAAGGAAGACCTTTGTGGAACTCATGAAAAGAGGAG
```

```
                L P V W L A Y Q V A S A G I T Y T D R R W C F
                ATCTTCCTGTTTGGCTGGCCTATCAGGTTGCATCTGCCGGAATAACCTACACAGATAGAAGATGGTGCTT

D G T T N N T I M E D S V P A E V W T R H G E

Amplicon 5

Amp5f2,087 F-T7
        CGACCAACAACACCATAATG>
        TGATGGCACGACCAACAACACCATAATGGAAGACAGTGTGCCGGCAGAGGTGTGGACCAGACACGGAGAG

<CCTCTC
        K R V L K P R W M D A R V C S D H A A L K S F K
        AAAAGAGTGCTCAAACCGAGGTGGATGGACGCCAGAGTTTGTTCAGATCATGCGGCCCTGAAGTCATTCA

TTTTCTC 2,162 R-T7 Amp4r            NS4A
        E F A A G K R G A A F G V M E A L G T L P G H
        AGGAGTTTGCCGCTGGGAAAAGAGGAGCGGCTTTTGGAGTGATGGAAGCCCTGGGAACACTGCCAGGACA

M T E R F Q E A I D N L A V L M R A E T G S R
        CATGACAGAGAGATTCCAGGAAGCCATTGACAACCTCGCTGTGCTCATGCGGGCAGAGACTGGAAGCAGG

P Y K A A A A Q L P E T L E T I M L L G L L G T
        CCTTACAAAGCCGCGGCGGCCCAATTGCCGGAGACCCTAGAGACCATAATGCTTTTGGGGTTGCTGGGAA

V S L G I F F V L M R N K G I G K M G F G M V
        CAGTCTCGCTGGGAATCTTCTTCGTCTTGATGAGGAACAAGGGCATAGGGAAGATGGGCTTTGGAATGGT

T L G A S A W L M W L S E I E P A R I A C V L
        GACTCTTGGGGCCAGCGCATGGCTCATGTGGCTCTCGGAAATTGAGCCAGCCAGAATTGCATGTGTCCTC

I V V F L L L V V L I P E P E K Q R S P Q D N Q
        ATTGTTGTGTTCCTATTGCTGGTGGTGCTCATACCTGAGCCAGAAAAGCAAAGATCTCCCCAGGACAACC

<2,624 R-T7 Amp5r
                                                NS4B
        M A I I I M V A V G L L G L I T A N E L G W L
        AAATGGCAATCATCATCATGGTAGCAGTAGGTCTTCTGGGCTTGATTACCGCCAATGAACTCGGATGGTT

E R T K S D L S H L M G R R E E G A T I G F S
        GGAGAGAACAAAGAGTGACCTAAGCCATCTAATGGGAAGGAGAGAGGAGGGGCAACCATAGGATTCTCA

M D I D L R P A S A W A I Y A A L T T F I T P A
        ATGGACATTGACCTGCGGCCAGCCTCAGCTTGGGCCATCTATGCTGCCTTGACAACTTTCATTACCCCAG

V Q H A V T T S Y N N Y S L M A M A T Q A G V
        CCGTCCAACATGCAGTGACCACCTCATACAACAACTACTCCTTAATGGCGATGGCCACGCAAGCTGGAGT

L F G M G K G M P F Y A W D F G V P L L M I G
        GTTGTTTGGCATGGGCAAAGGGATGCCATTCTACGCATGGGACTTTGGAGTCCCGCTGCTAATGATAGGT

C Y S Q L T P L T L I V A I I L L V A H Y M Y L
        TGCTACTCACAATTAACACCCCTGACCCTAATAGTGGCCATCATTTTGCTCGTGGCGCACTACATGTACT

I P G L Q A A A A R A A Q K R T A A G I M K N
        TGATCCCAGGGCTGCAGGCAGCAGCTGCGCGTGCTGCCCAGAAGAGAACGGCAGCTGGCATCATGAAGAA

P V V D G I V V T D I D T M T I D P Q V E K K
        CCCTGTTGTGGATGGAATAGTGGTGACTGACATTGACACAATGACAATTGACCCCCAAGTGGAGAAAAAG

M G Q V L L I A V A V S S A I L S R T A W G W G
        ATGGGACAGGTGCTACTCATAGCAGTAGCCGTCTCCAGCGCCATACTGTCGCGGACCGCCTGGGGGTGGG

E A G A L I T A A T S T L W E G S P N K Y W N
        GGGAGGCTGGGGCTCTGATCACAGCCGCAACTTCCACTTTGTGGGAAGGCTCTCCGAACAAGTACTGGAA

S S T A T S L C N I F R G S Y L A G A S L I Y
        CTCCTCTACAGCCACTTCACTGTGTAACATTTTTAGGGGAAGTTACTTGGCTGGAGCTTCTCTAATCTAC

T V T R N A G L V K R R G G G T G E T L G E K W
        ACAGTAACAAGAAACGCTGGCTTGGTCAAGAGACGTGGGGGTGGAACAGGAGAGACCCTGGGAGAGAAAT

K A R L N Q M S A L E F Y S Y K K S G I T E V
        GGAAGGCCCGCTTGAACCAGATGTCGGCCCTGGAGTTCTACTCCTACAAAAAGTCAGGCATCACCGAGGT

C R E E A R R A L K D G V A T G G H A V S R G
        GTGCAGAGAAGAGGCCCGCCGCGCCCTCAAGGACGGTGTGGCAACGGGAGGCCATGCTGTGTCCCGAGGA

S A K L R W L V E R G Y L Q P Y G K V I D L G C
        AGTGCAAAGCTGAGATGGTTGGTGGAGCGGGGATACCTGCAGCCCTATGGAAAGGTCATTGATCTTGGAT
```

-continued

```
   G  R  G  G  W  S  Y  Y  V  A  T  I  R  K  V  Q  E  V  K  G  Y  T  K
GTGGCAGAGGGGGCTGGAGTTACTACGTCGCCACCATCCGCAAAGTTCAAGAAGTGAAAGGATACACAAA

G  G  P  G  H  E  E  P  V  L  V  Q  S  Y  G  W  N  I  V  R  L  K  S
AGGAGGCCCTGGTCATGAAGAACCCGTGTTGGTGCAAAGCTATGGGTGGAACATAGTCCGTCTTAAGAGT

G  V  D  V  F  H  M  A  A  E  P  C  D  T  L  L  C  D  I  G  E  S  S  S
GGGGTGGACGTCTTTCATATGGCGGCTGAGCCGTGTGACACGTTGCTGTGTGACATAGGTGAGTCATCAT

S  P  E  V  E  E  A  R  T  L  R  V  L  S  M  V  G  D  W  L  E  K  R
CTAGTCCTGAAGTGGAAGAAGCACGGACGCTCAGAGTCCTCTCCATGGTGGGGATTGGCTTGAAAAAAG

P  G  A  F  C  I  K  V  L  C  P  Y  T  S  T  M  M  E  T  L  E  R  L
ACCAGGAGCCTTTTGTATAAAAGTGTTGTGCCCATACACCAGCACTATGATGGAAACCCTGGAGCGACTG

Q  R  R  Y  G  G  G  L  V  R  V  P  L  S  R  N  S  T  H  E  M  Y  W  V
CAGCGTAGGTATGGGGGAGGACTGGTCAGAGTGCCACTCTCCCGCAACTCTACACATGAGATGTACTGGG

S  G  A  K  S  N  T  I  K  S  V  S  T  T  S  Q  L  L  L  G  R  M  D
TCTCTGGAGCGAAAAGCAACACCATAAAAAGTGTGTCCACCACGAGCCAGCTCCTCTTGGGGCGCATGGA

N55
   G  P  R  R  P  V  K  Y  E  E  D  V  N  L  G  S  G  T  R  A  V  V  S
CGGGCCTAGGAGGCCAGTGAAATATGAGGAGGATGTGAATCTCGGCTCTGGCACGCGGGCTGTGGTAAGC

C  A  E  A  P  N  M  K  I  I  G  N  R  I  E  R  I  R  S  E  H  A  E  T
TGCGCTGAAGCTCCCAACATGAAGATCATTGGTAACCGCATTGAAAGGATCCGCAGTGAGCACGCGGAAA

W  F  F  D  E  N  H  P  Y  R  T  W  A  Y  H  G  S  Y  E  A  P  T  Q
CGTGGTTCTTTGACGAGAACCACCCATATAGGACATGGGCTTACCATGGAAGCTATGAGGCCCCCACACA

G  S  A  S  S  L  I  N  G  V  V  R  L  L  S  K  P  W  D  V  V  T  G
AGGGTCAGCGTCCTCTCTAATAAACGGGGTTGTCAGGCTCCTGTCAAAACCCTGGGATGGTGACTGGA

V  T  G  I  A  M  T  D  T  T  P  Y  G  Q  Q  R  V  F  K  E  K  V  D  T
GTCACAGGAATAGCCATGACCGACACCACACCGTATGGTCAGCAAAGAGTTTTCAAGGAAAAAGTGGACA

R  V  P  D  P  Q  E  G  T  R  Q  V  M  S  M  V  S  S  W  L  W  K  E
CTAGGGTGCCAGACCCCCAAGAAGGCACTCGTCAGGTTATGAGCATGGTCTCTTCCTGGTTGTGAAAGA

L  G  K  H  K  R  P  R  V  C  T  K  E  E  F  I  N  K  V  R  S  N  A
GCTAGGCAAACACAAACGGCCACGAGTCTGCACCAAAGAAGAGTTCATCAACAAGGTTCGTAGCAATGCA

A  L  G  A  I  F  E  E  E  K  E  W  K  T  A  V  E  A  V  N  D  P  R  F
GCATTAGGGGCAATATTTGAAGAGGAAAAAGAGTGGAAGACTGCAGTGGAAGCTGTGAACGATCCAAGGT

W  A  L  V  D  K  E  R  E  H  H  L  R  G  E  C  Q  S  C  V  Y  N  M
TCTGGGCTCTAGTGGACAAGGAAAGAGAGCACCCACCTGAGAGGAGAGTGCCAGAGCTGTGTGTACAACAT

M  G  K  R  E  K  K  Q  G  E  F  G  K  A  K  G  S  R  A  I  W  Y  M
GATGGGAAAAAGAGAAAAGAAACAAGGGGAATTTGGAAAGGCCAAGGGCAGCCGCGCCATCTGGTATATG

W  L  G  A  R  F  L  E  F  E  A  L  G  F  L  N  E  D  H  W  M  G  R  E
TGGCTAGGGGCTAGATTTCTAGAGTTCGAAGCCCTTGGATTCTTGAACGAGGATCACTGGATGGGGAGAG

N  S  G  G  G  V  E  G  L  G  L  Q  R  L  G  Y  V  L  E  E  M  S  R
AGAACTCAGGAGGTGGTGTTGAAGGGCTGGGATTACAAAGACTCGGATATGTCCTAGAAGAGATGAGTCG

I  P  G  G  R  M  Y  A  D  D  T  A  G  W  D  T  R  I  S  R  F  D  L
TATACCAGGAGGAAGGATGTATGCAGATGACACTGCTGGCTGGGACACCCGCATTAGCAGGTTTGATCTG

E  N  E  A  L  I  T  N  Q  M  E  K  G  H  R  A  L  A  L  A  I  I  K  Y
GAGAATGAAGCTCTAATCACCAACCAAATGGAGAAAGGGCACAGGGCCTTGGCATTGGCCATAATCAAGT

T  Y  Q  N  K  V  V  K  V  L  R  P  A  E  K  G  K  T  V  M  D  I  I
ACACATACCAAAACAAAGTGGTAAAGGTCCTTAGACCAGCTGAAAAAGGGAAAACAGTTATGGACATTAT

S  R  Q  D  Q  R  G  S  G  Q  V  V  T  Y  A  L  N  T  F  T  N  L  V
TTCGAGACAAGACCAAAGGGGAGCGGACAAGTTGTCACTTACGCTCTTAACACATTTACCAACCTAGTG

V  Q  L  I  R  N  M  E  A  E  E  V  L  E  M  Q  D  L  W  L  L  R  R  S
GTGCAACTCATTCGGAATATGGAGGCTGAGGAAGTTCTAGAGATGCAAGACTTGTGGCTGCTGCGGAGGT

E  K  V  T  N  W  L  Q  S  N  G  W  D  R  L  K  R  M  A  V  S  G  D
CAGAGAAAGTGACCAACTGGTTGCAGAGCAACGGATGGGATAGGCTCAAACGAATGGCAGTCAGTGGAGA
```

```
                              -continued
  D   C   V   V   K   P   I   D   D   R   F   A   H   A   L   R   F   L   N   D   M   G   K
TGATTGCGTTGTGAAGCCAATTGATGATAGGTTTGCACATGCCCTCAGGTTCTTGAATGATATGGGAAAA V   R   K   D   T   Q   E   W   K   P   S   T   G   W   D   N   W   E   E   V   P   F   C   S
GTTAGGAAGGACACACAAGAGTGGAAACCCTCAACTGGATGGGCAACTGGGAAGAAGTTCCGTTTTGCT H   H   F   N   K   L   H   L   K   D   G   R   S   I   V   V   P   C   R   H   Q   D   E
CCCACCACTTCAACAAGCTCCATCTCAAGGACGGGAGGTCCATTGTGGTTCCCTGCCGCCACCAAGATGA L   I   G   R   A   R   V   S   P   G   A   G   W   S   I   R   E   T   A   C   L   A   K
ACTGATTGGCCGGGCCCGCGTCTCTCCAGGGGCGGGATGGAGCATCCGGGAGACTGCTTGCCTAGCAAAA S   Y   A   Q   M   W   Q   L   L   Y   F   H   R   R   D   L   R   L   M   A   N   A   I   C
TCATATGCGCAAATGTGGCAGCTCCTTTATTTCCACAGAAGGGACCTCCGACTGATGGCCAATGCCATTT S   S   V   P   V   D   W   V   P   T   G   R   T   T   W   S   I   H   G   K   G   E   W
GTTCATCTGTGCCAGTTGACTGGGTTCCAACTGGGAGAACTACCTGGTCAATCCATGGAAAGGGAGAATG M   T   T   E   D   M   L   V   V   W   N   R   V   W   I   E   E   N   D   H   M   E   D
GATGACCACTGAAGACATGCTTGTGGTGTGGAACAGAGTGTGGATTGAGGAGAACGACCACATGGAAGAC K   T   P   V   T   K   W   T   D   I   P   Y   L   G   K   R   E   D   L   W   C   G   S   L
AAGACCCCAGTTACGAAATGGACAGACATTCCCTATTTGGGAAAAAGGGAAGACTTGTGGTGTGGATCTC I   G   H   R   P   R   T   T   W   A   E   N   I   K   N   T   V   N   M   V   R   R   I
TCATAGGGCACAGACCGCGCACCACCTGGGCTGAGAACATTAAAAACACAGTCAACATGGTGCGCAGGAT I   G   D   E   E   K   Y   M   D   Y   L   S   T   Q   V   R   Y   L   G   E   E   G   S
CATAGGTGATGAAGAAAAGTACATGGACTACCTATCCACCCAAGTTCGCTACTTGGGTGAAGAAGGGTCT T   P   G   V   L   3'UTR
ACACCTGGAGTGCTGTAAGCACCAATCTTAATGTTGTCAGGCCTGCTAGTCAGCCACAGCTTGGGGAAAG

CTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAG

GCGCAGGATGGGAAAAGAAGGTGGCGACCTTCCCCACCCTTCAATCTGGGGCCTGAACTGGAGATCAGCT

GTGGATCTCCAGAAGAGGGACTAGTGGTTAGAGGA
```

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Demonstration of dsRNA Production in Mosquitoes Infected with Bacteria (*E. Coli* Strain H115) Expressing dsRNA-Dengue As demonstrated in FIG. 1, the present inventors demonstrate that *E. coli* used to infect mosquitoes may produce dsRNA in the gut. More specifically, in this embodiment, the present inventors demonstrated that mosquitos infected with a genetically modified strain of *E. coli* that actively expressed a dsRNA-dengue. LUC or DENV bacterial DNA were used as positive control. Total RNA was DNase treated and converted into a cDNA library using a DENV or LUC reverse primer.

Example 2: Mosquitoes Harboring *E. coli* H115 Expressing dsRNA-Dengue and Infected with Dengue Virus in a Blood Meal have Significant Reductions in Dengue Viral Loads in Head The present inventors tested the effect of carriage of *E. coli* transformed by pTac plasmids producing dsRNA complementary to DENV-2 (strain JAM 1409) on infection of *Aedes aegypti* (Rockefeller strain) by DENV-2 (strain NGC). In this plasmid, the dsRNA is expressed constitutively by design. At Day 5 post infection, there was no significant difference in terms of DENV-2 infection rate, mean body and head titers, and dissemination from infected bodies among the four treatment groups, which included:

(i) Control mosquitoes fed bacteria-free sugar
(ii) Control mosquitoes fed sugar spiked with *E. coli* carrying a pTac plasmid with a GFP insert (GFP control)
(iii) Control mosquitoes fed sugar spiked with *E. coli* carrying a pTac plasmid that produced dsRNA against luciferase, an irrelevant target (LUC control)
(iv) Mosquitoes fed sugar spiked with *E. coli* carrying a pTac plasmid that produced dsRNA complementary to DENV-2 JAM-1409

As demonstrated in Tables 4-6 below, the present inventors demonstrated that neither body titer nor head titer differed significantly among treatments at Day 5. After 10 days post blood meal, the body titer of infected mosquitoes was similar in all groups, but head titer in dsDENV-2-treated mosquitoes was significantly (r=0.05) reduced by 21% compared to dsLuc or sugar control. This result demonstrates bacterial delivery of dsRNA to target inactivation of Dengue virus.

TABLE 4 bacterial delivery of dsRNA to target inactivation of Dengue virus.

| Day | Treatment | N | % Infected | Mean Body* Titer ($\log_{10}$pfu/body) ± 1SE | % Disseminated | Mean Head* Titer ($\log_{10}$pfu/body) ± 1SE | % Infected Bodies that Disseminated |
|---|---|---|---|---|---|---|---|
| 5 | Sugar Control | 22 | 59.1 | 3.26 ± 0.24 | 13.6 | 3.07 ± 0.91 | 23 |
| 5 | GFP plasmid | 7 | 71.4 | 3.68 ± 0.39 | 33.3 | 3.37 ± 1.11 | 50 |
| 5 | LUC plasmid | 24 | 79.2 | 3.07 ± 0.20 | 16.7 | 1.83 ± 0.79 | 21 |
| 5 | DENV-2 plasmid | 7 | 57.1 | 3.94 ± 0.44 | 42.9 | 2.87 ± 0.81 | 75 |
| 10 | Sugar Control | 17 | 70.6 | 4.39 ± 0.17 | 64.7 | 3.35 ± 0.27 | 92 |
| 10 | GFP plasmid | 5 | 60.0 | 4.71 ± 0.33 | 60.0 | 4.64 ± 0.53 | 100 |
| 10 | LUC plasmid | 9 | 77.8 | 4.13 ± 0.22 | 55.6 | 3.40 ± 0.40 | 71 |
| 10 | DENV-2 plasmid | 9 | 88.9 | 4.40 ± 0.21 | 88.9 | 2.68 ± 0.32 | 100 |

TABLE 5

Mosquito heads viral titer at day 10.

| Sugar control | DENV dsRNA | Luc-dsRNA |
|---|---|---|
| 1 | 1.812913357 | 2.505149978 |
| 2.423245874 | 2.423245874 | 3.352182518 |
| 2.596597096 | 2.498310554 | 3.40654018 |
| 2.667452953 | 2.62838893 | 3.414973348 |
| 3.33243846 | 2.648360011 | 4.311753861 |
| 3.389166084 | 3.06069784 | |
| 3.568201724 | 3.096910013 | |
| 3.633468456 | 3.255272505 | |
| 4.484299839 | | |
| 4.505149978 | | |
| 5.190331698 | | |

Bolded results indicate virus titer higher than max titer in DENV-treated group. It is significant that in both Luc and Sugar control groups, the majority of samples have viral titer higher than maximal viral titer in dsDENV-treated group.

Example 3: Identification of New Mosquito Enteric Bacteria that Persist Through all Life Stages The present inventors isolated a strain of *Serratia fonticola*, AeS1, from wild caught *Aedes* mosquitoes. The present inventors further screened the gut bacteria in newly emerged *Aedes aegypti* Rock strain in the lab, and isolated a new strain of *S. fonticola*, MS5. The genome sequences of the strains MS5 and AeS1 are almost identical, suggesting that *Serratia fonticola* is naturally associated with *Aedes* mosquitoes persistently. In addition, taxa in genus *Serratia* have been found associated with *Aedes aegypti* in various populations in different geographic locations. The strains AeS1 and MS5 both are able to pass transstadially, where bacterial strain remains with the vector from one life stage to the next, in this case from larvae to adults and proliferate well in the blood fed gut.

The present inventors performed genome annotation demonstrating that the genomes of MS5 and S1 are almost identical. S1 was isolated from wild caught *Aedes albopictus* mosquitoes from Florida, and MS5 was isolated from a laboratory strain of *Ae. aegypti* strain. This indication demonstrates that this *Serratia* strain is persistently associated with *Aedes* mosquitoes. In addition, both S1 and MS5 are able to pass from larvae to adults, and enriched by a blood meal in the adult guts. The prevalence in the gut and capability of transstadial passage from larvae to adults identifies this strain as a novel candidate to act as a vehicle of dsRNA for sustainable application in the field, as well as applications in aquatic larval habitats and in sugar stations to deliver dsRNA, and other RNA and/or DNA inhibitory molecules to mosquitoes. Additional candidates may include *Panteoea* sp., Ae16, *Cedecea neteri*, Ag1, and JC8031 among others identified above. These strains were isolated by the present inventors from mosquitos, and are predominantly found in the gut. The present inventors have also demonstrated that all of the above referenced strains proliferate favorably in the gut after a blood meal. Like, AeS1, these strains can pass from the larval stage into the adult stage as well as through vertical transmission.

Example 4: Identification of Endo-Symbiont Microorganisms Including, Discovery, Culturability, and Transformation Potential As noted above, bacterial endosymbionts may be beneficial for proper development and maturation of mosquitoes after eggs hatch into larvae, pupate and emerge as adults. Toward the goal of identifying and genetically modifying bacterial endosymbionts, *Aedes aegypti* mosquito eggs originally obtained from Cd. Hidalgo and propagated in the laboratory were surface sterilized and prepared for cultivation of the bacteria residing within the shell of the egg and possibly the interior of the egg. The present inventors then passaged and mechanically diluted the bacteria using the traditional three way streak method to obtain pure cultures. Isolates from purified colonies were grown overnight and banked in 20% glycerol (v/v) final and stored at −80° C. Isolates were then grown in LB medium and prepared for identification by MALDI biotyping using a Bruker Microflex LRF. The present inventors collected 261 bacterial isolates derived from surface sterilized *Aedes aegypti* eggs and 2 bacterial isolates from adult mosquitoes that appear to flourish during feeding on blood were stored and cataloged. A list of the strains and identification as determined by the MALDI biotyping procedure are included (see TABLE 7).

Approximately, 47 of the 261 strains were generally unidentifiable through biotyping; 16S rDNA sequencing was utilized by the present inventors to provide additional information on identity. Additionally, the present inventors used 16s rDNA sequencing to obtain more information on the identity of the putative 23 *Pantoea/Enterobacter* spp. isolates and 10 putative *Pseudomonas putida* and *Pseudomonas mosselli* isolates as these may be potential candidates for environmental release. Since the *Pantoea* spp. are a relatively new reclassification of bacteria formerly classified as *Enterobacter* spp., as such the present inventors employed more sophisticated genotyping methodologies for accurate identification. Six isolates of *Gordonia rubripertincta* and 2 additional bacterial isolates from adult mosquitoes were also selected for 16s rDNA sequencing. A total of 90 isolates were submitted for 16s rDNA sequencing. Contiged full length (approx. 1.3-1.6 kb) 16s rDNA sequences are included (not shown).

Figure 3:
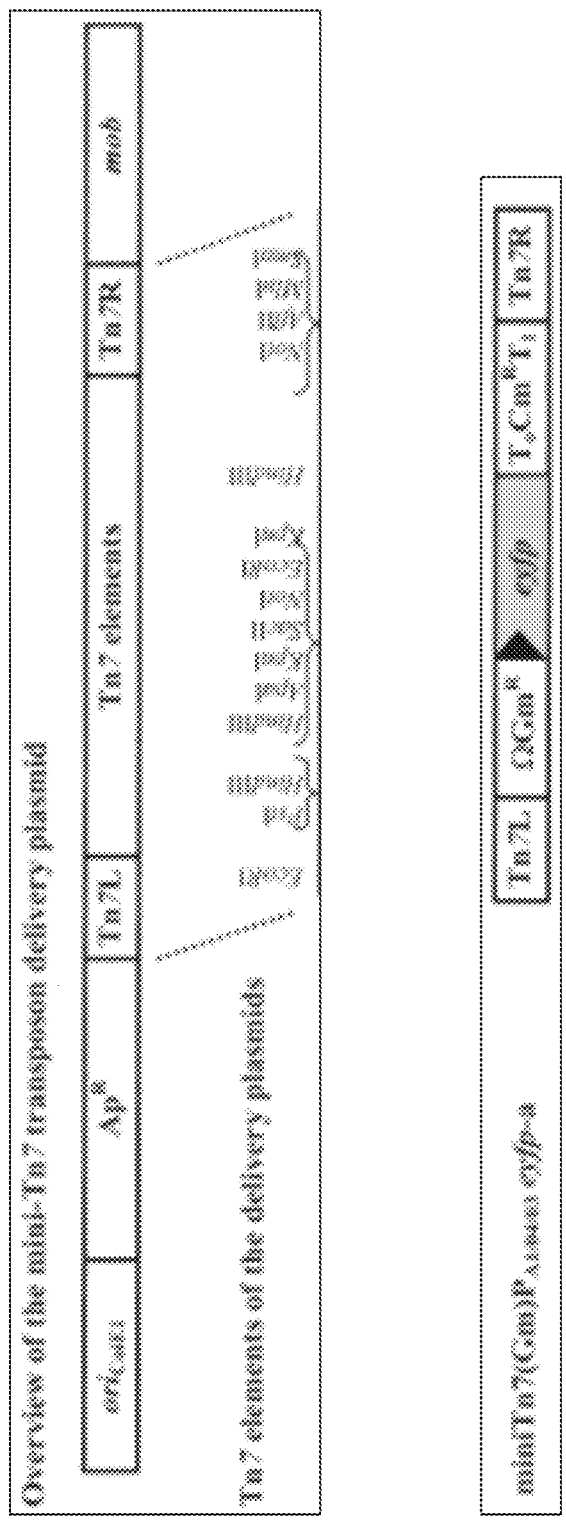
FIG. 3: Schematic description of the eYFP delivery vector and sample images of bacterial endosymbionts expressing eYFP bacteria in one embodiment thereof. The Tn7 delivery plasmid is shown with a gentamicin resistance gene (GmR) provided by aacC1 encoding acetyltransferase-3-1, from plasmid pAComegaGm. The delivery plasmid is based on pUC19 and carries resistance to ampicillin. Ω shows that the resistance gene is flanked by transcription and translation terminators and the fluorescent proteins are from Clontech Laboratories (Palo Alto, Calif.). All constructs contain the ribosomal binding site, RBSII, in front of the fluorescent gene and terminator T0 and T1. Useful known restriction sites are indicated, the figure is not drawn to scale.
Figure 4:
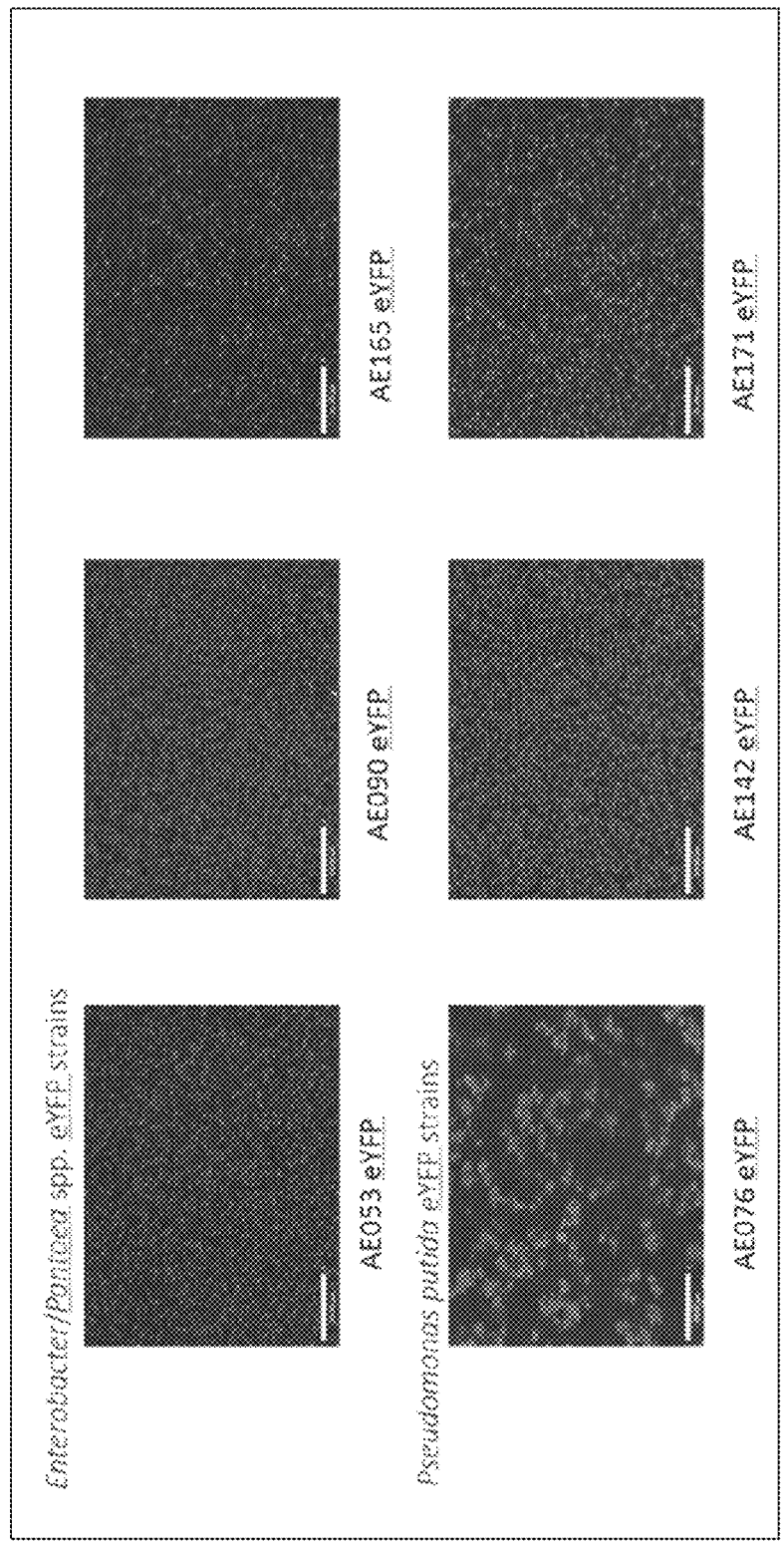
FIG. 4: Representative endosymbiotic strains that are expressing the eYFP bacteria in one embodiment thereof.

The present inventors additionally characterized and validated selected bacterial isolates to be engineered for paratransgenesis. Preliminary choice of these bacterial isolates for recombineering may be based on a lack of evidence for pathogenicity in humans and preliminary identification results (see FIG. 2). 10 isolates of the *Enterobacter/Pantoea* spp. and 12 isolates of the *Pseudomonas* spp. were evaluated to determine additional features, such as, plasmid uptake, plasmid replication, and Tn7 integration, which includes antibiotic susceptibility profiling, mating potential, plasmid replication, plasmid stability, and Tn7 integration of fluorescent markers. The present inventors focused recombineering approaches on the use of miniTn7-eYFP. As would be recognized by those of ordinary skill in the art, this is a widely used Tn7 integration plasmid that delivers a YFP fluorescent marker that is expressed in a variety of Gram-negative bacterial strains (see FIG. 3 for a description of the delivery plasmid). It should be noted that all of the strains listed in FIG. 2 are expressing fluorescence (see FIG. 4), for use in tracking bacterial colonization of the mosquitoes during various phases of development.

Figure 6:
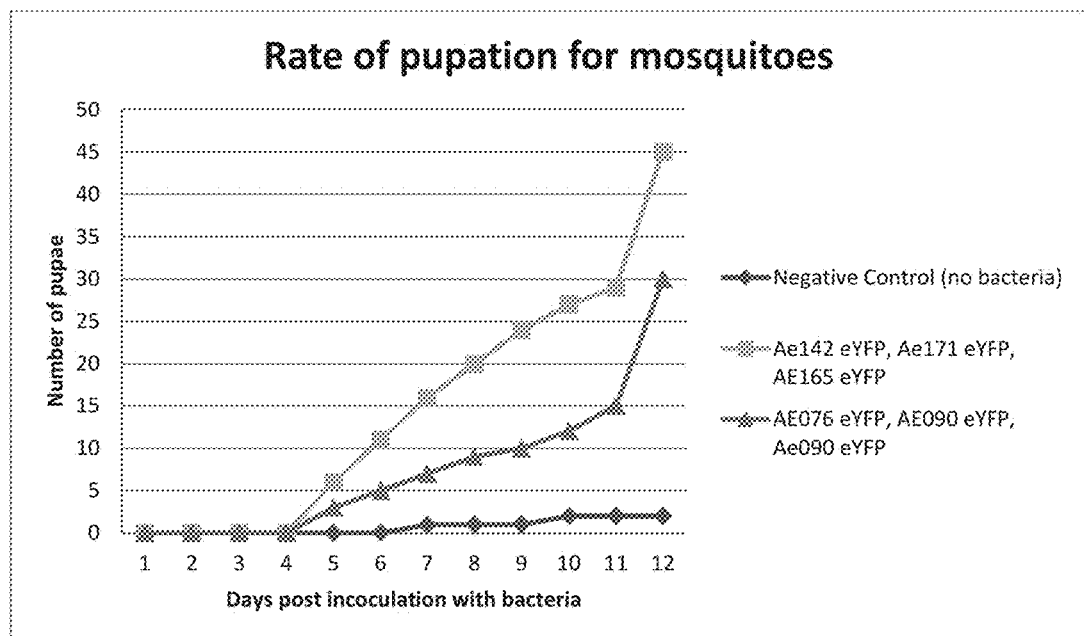
FIG. 6: Representative rate of pupation for mosquitos infected with selected endosymbiotic bacteria in one embodiment thereof. Specifically, bacterial strains engineered to express eYFP were fed to larvae. *Pseudomonas* spp. (Ae076, Ae142, and Ae171) and *Pantoea/Enterobacter* spp. (Ae053, Ae090, and Ae165) were grown to mid-log and diluted to a final concentration of OD 0.3 in 50 mL sterile milliQ water with 500 μL of sterile liver powder added. Larvae were treated with pen/strep for 24 hours after hatching and then washed and transferred to the feeding solutions containing bacterial strains. The negative control larvae were placed in 50 mL of sterile milliQ water with 500 µL of sterile liver powder (no bacteria added). The above graph shows the estimated rate of pupation for the six larvae groups fed eYFP labelled bacteria and the negative control larvae. On day 11, the eYFP larval feeding solution was spiked with 2 mL of overnight culture for each bacterial strain, which resulted in increased pupation.
Figure 7:
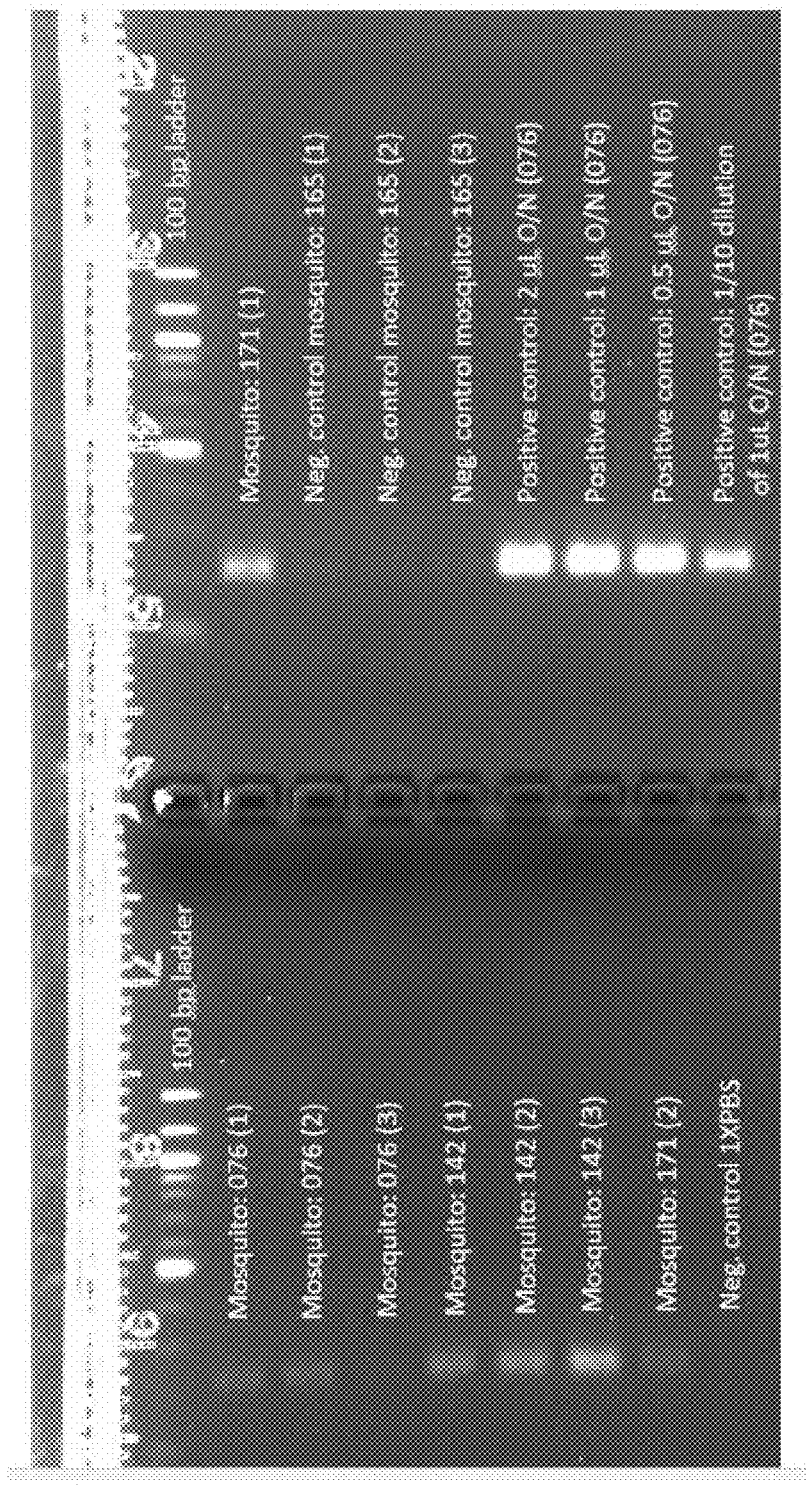
FIG. 7: Demonstrates PCR detection using *P. putida*-specific/Tn7 PCR primers for bacterial endosymbiont colonization of adult mosquitoes. In this embodiment, adult mosquitoes were fed three bacteria endosymbiotic strains of *Pseudomonas putida* (Ae076, Ae142, and Ae171) and negative control mosquitoes were fed an *Enterobacter* strain (Ae165). Mosquitoes were homogenized in 100 µL of sterile phosphate buffered saline (PBS) with a sterile pestle. Four control Ae165 mosquitoes were homogenized and spiked with varying amount of overnight culture for Ae076 for positive controls to determine the potential limits of detection for the PCR reaction. The homogenized mosquitoes were boiled at 99° C. in a heat block for 20 minutes. A negative control of phosphate buffered saline (PBS) was also included.

The present inventors conducted initial feeding experiments which indicate that the bacterial endosymbionts foster the growth and development of the mosquito, which can be visually observed as a decrease in the length of time required to develop into pupae and emerge as adults (see FIG. 5-6). PCR targeted to the synthetic portion of the Tn7 vector and the *Pseudomonas putida* chromosome was also used to evaluate the potential of 3 strains to colonize individual mosquitoes. A positive signal was detected in 7 out of 8 mosquitoes surveyed for colonization by the endosymbiotic bacterial strains containing the eYFP integrated into the chromosome, Ae076, Ae142, and Ae171 (see FIG. 7).

Representative growth promotion of mosquitoes by selected endosymbiotic bacteria is demonstrated in one embodiment thereof. Specifically, representative larvae reared with bacterial endosymbionts (FIG. 5, left panel, bacterial isolate Ae165 shown) develop faster than those without bacteria added to the mosquito rearing solution (FIG. 5, right panel, negative control). Representative rate of pupation for mosquitos infected with selected endosymbiotic bacteria in one embodiment thereof. Specifically, bacterial strains engineered to express eYFP were fed to larvae. *Pseudomonas* spp. (Ae076, Ae142, and Ae171) and *Pantoea/Enterobacter* spp. (Ae053, Ae090, and Ae165) were grown to mid-log and diluted to a final concentration of OD 0.3 in 50 mL sterile milliQ water with 500 µL of sterile liver powder added. Larvae were treated with pen/strep for 24 hours after hatching and then wash and transferred to the feeding solutions containing bacterial strains. The negative control larvae were placed in 50 mL of sterile milliQ water with 500 µL of sterile liver powder (no bacteria added). The estimated rate of pupation for the six larvae groups fed eYFP labelled bacteria and the negative control larvae. On day 11, the eYFP larval feeding solution was spiked with 2 mL of overnight culture for each bacterial strain, which resulted in increased pupation.

TABLE 7

List of cataloged endosymbiont strains and Biotyper identification.

| Strain name | Biotyper ID | Media for isolation | Grow In |
| --- | --- | --- | --- |
| AE001 | *Stenotrophomonas maltophilia* | Blood Agar | BHI |
| AE002 | *Stenotrophomonas maltophilia* | Blood Agar | BHI |
| AE003 | *Enterobacter cloacae* | Blood Agar | BHI |
| AE004 | *Achromobacter insolitus* | Blood Agar | BHI |
| AE005 | *Stenotrophomonas maltophilia* | Blood Agar | BHI |
| AE006 | *Stenotrophomonas maltophilia* | Blood Agar | BHI |
| AE007 | *Staphylococcus warneri* | Blood Agar | BHI |
| AE008 | *Enterobacter cloacae* | LB Agar | LB |
| AE009 | *Achromobacter insolitus* | LB Agar | LB |
| AE010 | *Stenotrophomonas maltophilia* | LB Agar | LB |
| AE011 | *Stenotrophomonas maltophilia* | LB Agar | LB |
| AE012 | *Micrococcus luteus* | LB Agar | LB |
| AE013 | *Stenotrophomonas maltophilia* | LB Agar | LB |
| AE014 | no ID | LB Agar | LB |
| AE015 | no ID | LB Agar | LB |
| AE016 | *Rhizobium radiobacter* | Blood Agar | BHI |
| AE017 | no ID | LB Agar | LB |
| AE018 | *Rhizobium radiobacter* | LB Agar | LB |
| AE019 | no ID | LB Agar | LB |
| AE020 | no ID | LB Agar | LB |
| AE021 | no ID | LB Agar | LB |
| AE022 | *Rhizobium radiobacter* | LB Agar | LB |
| AE023 | *Stenotrophomonas maltophilia* | LB Agar | LB |
| AE024 | *Micrococcus luteus* | LB Agar | LB |
| AE025 | *Stenotrophomonas maltophilia* | LB Agar | LB |
| AE026 | *Stenotrophomonas maltophilia* | Blood Agar | BHI |
| AE027 | *Stenotrophomonas maltophilia* | Blood Agar | BHI |

TABLE 7-continued

List of cataloged endosymbiont strains and Biotyper identification.

| Strain name | Biotyper ID | Media for isolation | Grow In |
|---|---|---|---|
| AE028 | no ID | Blood Agar | BHI |
| AE029 | Stenotrophomonas maltophilia | Blood Agar | BHI |
| AE030 | Stenotrophomonas maltophilia | Blood Agar | BHI |
| AE031 | Stenotrophomonas maltophilia | Blood Agar | BHI |
| AE032 | Stenotrophomonas maltophilia | Blood Agar | BHI |
| AE033 | Nocardioides simplex | LB Agar | LB |
| AE034 | Nocardioides simplex | LB Agar | LB |
| AE035 | Nocardioides simplex | LB Agar | LB |
| AE036 | Neisseria macacae | LB Agar | LB |
| AE037 | Neisseria macacae | LB Agar | LB |
| AE038 | Nocardioides simplex | Blood Agar | BHI |
| AE039 | no ID | TSA Agar | 100% TSB |
| AE040 | Stenotrophomonas maltophilia | Blood Agar | BHI |
| AE041 | Stenotrophomonas maltophilia | Blood Agar | BHI |
| AE042 | Stenotrophomonas maltophilia | Blood Agar | BHI |
| AE043 | Achromobacter insolitus | Blood Agar | BHI |
| AE044 | Nocardioides simplex | LB Agar | LB |
| AE045 | Nocardioides simplex | LB Agar | LB |
| AE046 | No ID | LB Agar | LB |
| AE047 | Rhizobium radiobacter | LB Agar | LB |
| AE048 | Nocardioides simplex | LB Agar | LB |
| AE049 | Nocardioides simplex | LB Agar | LB |
| AE050 | Neisseria flavescens | LB Agar | LB |
| AE051 | Nocardioides simplex | LB Agar | LB |
| AE052 | Bacillus cereus | MHB-PBS | MHB |
| AE053 | Enterobacter kobei | MHB-PBS | MHB |
| AE054 | Enterobacter kobei | MHB-PBS | MHB |
| AE055 | Pseudomonas mosselii | MHB-PBS | MHB |
| AE056 | Rhizobium radiobacter | MHB-PBS | MHB |
| AE057 | Microbacterium natoriense | MHB-PBS | MHB |
| AE058 | Enterobacter kobei | MHB-water | MHB |
| AE059 | Stenotrophomonas maltophilia | MHB-water | MHB |
| AE060 | Stenotrophomonas maltophilia | MHB-water | MHB |
| AE061 | Achromobacter insolitus | MHB-water | MHB |
| AE062 | Pseudomonas mosselii | LB-water | LB |
| AE063 | Rhizobium radiobacter | LB-water | LB |
| AE064 | Rhizobium radiobacter | LB-water | LB |
| AE065 | Rhizobium radiobacter | LB-PBS | LB |
| AE066 | Agromyces mediolanus | LB-PBS | LB |
| AE067 | Microbacterium paraoxydans | LB-PBS | LB |
| AE068 | Rhizobium radiobacter | LB-PBS | LB |
| AE069 | No ID | 0.1% TSA | LB |
| AE070 | No ID | 10% TSA | LB |
| AE071 | No ID | LB-PBS | LB |
| AE072 | Stenotrophomonas maltophilia | LB-PBS | LB |
| AE073 | Enterobacter kobei | LB-water | LB |
| AE074 | Pseudomonas mosselii | LB-water | LB |
| AE075 | Serratia marcescens | LB-water | LB |
| AE076 | Pseudomonas putida group | LB-water | LB |
| AE077 | Enterobacter cloacae | BHI-water | BHI |
| AE078 | Pseudomonas mosselii | BHI-water | BHI |
| AE079 | Pseudomonas mosselii | BHI-water | BHI |
| AE080 | Staphylococcus xylosus | BHI-water | BHI |
| AE081 | No ID | BHI-water | BHI |
| AE082 | Rhizobium radiobacter | BHI-water | BHI |
| AE083 | Bacillus flexus | BHI-PBS | BHI |
| AE084 | Stenotrophomonas maltophilia | BHI-PBS | BHI |
| AE085 | Delftia acidovorans | BHI-PBS | BHI |
| AE086 | Staphylococcus kloosii | Blood-water | BHI |
| AE087 | No ID | Blood-water | BHI |
| AE088 | Rhizobium radiobacter | Blood-water | BHI |
| AE089 | Rhizobium radiobacter | CaCO3-water | LB |
| AE090 | Enterobacter cloacae | CaCO3-PBS | LB |
| AE091 | Staphylococcus xylosus | CaCO3-PBS | LB |
| AE092 | Delftia acidovorans | CaCO3-PBS | LB |
| AE093 | Bacillus cereus | MHB-PBS | MHB |
| AE094 | Pseudomonas mosselii | MHB-PBS | MHB |
| AE095 | Enterobacter kobei | MHB-water | MHB |
| AE096 | Pseudomonas mosselii | MHB-water | MHB |
| AE097 | Bacillus cereus | BHI-water | BHI |
| AE098 | Bacillus cereus | BHI-PBS | BHI |
| AE099 | Pseudomonas mosselii | BHI-PBS | BHI |
| AE100 | Pseudomonas mosselii | BHI-PBS | BHI |
| AE101 | Bacillus cereus | BHI-PBS | BHI |
| AE102 | Pseudomonas mosselii | BHI-PBS | BHI |

TABLE 7-continued

List of cataloged endosymbiont strains and Biotyper identification.

| Strain name | Biotyper ID | Media for isolation | Grow In |
|---|---|---|---|
| AE103 | Pseudomonas mosselii | BHI-PBS | BHI |
| AE104 | Pseudomonas mosselii | LB-PBS | LB |
| AE105 | Pseudomonas mosselii | LB-PBS | LB |
| AE106 | Achromobacter piechaudii | LB-PBS | LB |
| AE107 | Stenotrophomonas acidaminiphila | LB-PBS | LB |
| AE108 | Rhizobium radiobacter | Blood-water | BHI |
| AE109 | Agromyces mediolanus | Blood-PBS | BHI |
| AE110 | No ID | Blood-PBS | BHI |
| AE111 | Staphylococcus kloosii | Blood-PBS | BHI |
| AE112 | Acinetobacter junii | Blood-PBS | BHI |
| AE113 | Staphylococcus kloosii | Blood-PBS | BHI |
| AE114 | Agromyces mediolanus | MHB-water (enriched) | MHB |
| AE115 | Rhodococcus equi | MHB-water (enriched) | MHB |
| AE116 | Agromyces mediolanus | MHB-water (enriched) | MHB |
| AE117 | Agromyces mediolanus | MHB-water (enriched) | MHB |
| AE118 | Bacillus flexus | MHB-water (enriched) | MHB |
| AE119 | Bacillus flexus | MHB-water (enriched) | MHB |
| AE120 | Rhodococcus equi | MHB-water (enriched) | MHB |
| AE121 | Rhodococcus equi | MHB-water (enriched) | MHB |
| AE122 | Agromyces mediolanus | MHB-PBS (enriched) | MHB |
| AE123 | Agromyces mediolanus | MHB-PBS (enriched) | MHB |
| AE124 | Microbacterium paraoxydans | MHB-PBS (enriched) | MHB |
| AE125 | Arthrobacter polychromogenes | MHB-PBS (enriched) | MHB |
| AE126 | Agromyces mediolanus | MHB-PBS (enriched) | MHB |
| AE127 | Bacillus cereus | Blood-PBS (enriched) | BHI |
| AE128 | Tsukamurella species | Blood-PBS (enriched) | BHI |
| AE129 | Tsukamurella inchonensis | Blood-PBS (enriched) | BHI |
| AE130 | No ID | MHB-PBS (enriched) | MHB |
| AE131 | Gordonia rubripertincta | MHB-PBS (enriched) | MHB |
| AE132 | Gordonia rubripertincta | MHB-PBS (enriched) | MHB |
| AE133 | Gordonia rubripertincta | MHB-water (enriched) | MHB |
| AE134 | No ID | MHB-water (enriched) | MHB |
| AE135 | Enterobacter kobei | MHB-water | MHB |
| AE136 | Pseudomonas mosselii | MHB-water | MHB |
| AE137 | Serratia ureilytica | BHI-water | BHI |
| AE138 | Enterobacter kobei | BHI-PBS | BHI |
| AE139 | Enterobacter kobei | BHI-PBS | BHI |
| AE140 | Pseudomonas mosselii | LB-water | LB |
| AE141 | Serratia marcescens | LB-water | LB |
| AE142 | Pseudomonas putida group | LB-water | LB |
| AE143 | Enterobacter kobei | LB-PBS | LB |
| AE144 | Enterobacter kobei | LB-PBS | LB |
| AE145 | no ID | LB-PBS | LB |
| AE146 | Bacillus cereus | LB-PBS | LB |
| AE147 | Bacillus cereus | LB-PBS | LB |
| AE148 | Enterobacter kobei | LB-PBS | LB |
| AE149 | Pseudomonas mosselii | Blood-water | BHI |
| AE150 | Pseudomonas mosselii | Blood-water | BHI |
| AE151 | Pseudomonas otitidis | Blood-water | BHI |
| AE152 | Pseudomonas otitidis | Blood-water | BHI |
| AE153 | Pseudomonas mosselii | Blood-PBS | BHI |
| AE154 | Pseudomonas mosselii | Blood-PBS | BHI |
| AE155 | Pseudomonas mosselii | Blood-PBS | BHI |
| AE156 | Pseudomonas mosselii | Blood-PBS | BHI |
| AE157 | Enterobacter kobei | Blood-PBS | BHI |
| AE158 | Stenotrophomonas maltophilia | Blood-PBS | BHI |
| AE159 | Stenotrophomonas maltophilia | Blood-PBS | BHI |
| AE160 | Flavobacterium lindanitolerans | Blood-PBS | BHI |
| AE161 | Agromyces mediolanus | Blood-PBS | BHI |
| AE162 | no ID | Blood-PBS | BHI |
| AE163 | Pseudomonas otitidis | Blood-PBS | BHI |
| AE164 | Enterobacter kobei | LB-PBS | LB |
| AE165 | Enterobacter kobei | CaCO3-water | LB |
| AE166 | Pseudomonas mosselii | CaCO3-water | LB |
| AE167 | Enterobacter kobei | CaCO3-water | LB |
| AE168 | Pseudomonas mosselii | CaCO3-water | LB |
| AE169 | Pseudomonas mosselii | CaCO3-water | LB |
| AE170 | Pseudomonas mosselii | CaCO3-water | LB |
| AE171 | Pseudomonas putida group | CaCO3-water | LB |
| AE172 | Enterobacter kobei | CaCO3-PBS | LB |
| AE173 | Enterobacter asburiae | CaCO3-PBS | LB |
| AE174 | Pseudomonas mosselii | CaCO3-PBS | LB |
| AE175 | Pseudomonas mosselii | CaCO3-PBS | LB |
| AE176 | Pseudomonas mosselii | CaCO3-PBS | LB |

TABLE 7-continued

List of cataloged endosymbiont strains and Biotyper identification.

| Strain name | Biotyper ID | Media for isolation | Grow In |
|---|---|---|---|
| AE177 | *Pseudomonas mosselii* | CaCO3-PBS | LB |
| AE178 | *Enterobacter kobei* | CaCO3-PBS | LB |
| AE179 | *Pseudomonas otitidis* | CaCO3-PBS | LB |
| AE180 | *Pseudomonas putida* group | CaCO3-PBS | LB |
| AE181 | *Bacillus cereus* | CaCO3-PBS (enriched) | LB |
| AE182 | *Bacillus cereus* | CaCO3-PBS (enriched) | LB |
| AE183 | *Paenibacillus glucanolyticus* | LB-water (enriched) | LB |
| AE184 | *Gordonia rubripertincta* | LB-water (enriched) | LB |
| AE185 | *Arthrobacter polychromogenes* | LB-PBS (enriched) | LB |
| AE186 | no ID | LB-PBS enriched) | LB |
| AE187 | *Gordonia rubripertincta* | LB-PBS (enriched) | LB |
| AE188 | no ID | MHB-water (enriched) | MHB |
| AE189 | *Agromyces mediolanus* | MHB-PBS (enriched) | MHB |
| AE190 | *Leucobacter chironomi* | MHB-PBS (enriched) | MHB |
| AE191 | no ID | BHI-water (enriched) | BHI |
| AE192 | *Bacillus flexus* | BHI-PBS (enriched) | BHI |
| AE193 | no ID | BHI-PBS (enriched) | BHI |
| AE194 | *Rhodococcus equi* | BHI-PBS (enriched) | BHI |
| AE195 | no ID | Blood-water (enriched) | BHI |
| AE196 | no ID | Blood-water (enriched) | BHI |
| AE197 | no ID | LB-PBS (enriched) | LB |
| AE198 | no ID | LB-PBS (enriched) | LB |
| AE199 | no ID | BHI-PBS (enriched) | BHI |
| AE200 | *Enterobacter kobei* | LB-water | LB |
| AE201 | *Stenotrophomonas maltophilia* | LB-water | LB |
| AE202 | *Stenotrophomonas acidaminiphila* | Blood-PBS | TSB |
| AE203 | *Stenotrophomonas acidaminiphila* | Blood-PBS | TSB |
| AE204 | *Rhizobium radiobacter* | CaCO3-water | LB |
| AE205 | no ID | CaCO3-PBS | LB |
| AE206 | *Bacillus cereus* | CaCO3-PBS | LB |
| AE207 | *Bacillus cereus* | BHI-PBS (enriched) | BHI |
| AE208 | *Bacillus cereus* | BHI-PBS (enriched) | BHI |
| AE209 | *Bacillus cereus* | BHI-water (enriched) | BHI |
| AE210 | *Bacillus cereus* | LB-PBS (enriched) | LB |
| AE211 | *Bacillus cereus* | Blood-PBS (enriched) | BHI |
| AE212 | *Cellulosimicrobium cellulans* | CaCO3-water (enriched) | LB |
| AE213 | *Brevibacterium celere* | CaCO3-water (enriched) | LB |
| AE214 | *Rhodococcus equi* | CaCO3-water (enriched) | LB |
| AE215 | *Agromyces mediolanus* | CaCO3-water (enriched) | LB |
| AE216 | *Agromyces mediolanus* | CaCO3-PBS (enriched) | LB |
| AE217 | no ID | 1% TSA | TSB |
| AE218 | no ID | 1% TSA | TSB |
| AE219 | no ID | 10% TSA | TSB |
| AE220 | no ID | MHB-PBS (enriched) | MHB |
| AE221 | no ID | MHB-PBS (enriched) | MHB |
| AE222 | no ID | BHI-PBS (enriched) | BHI |
| AE223 | *Arthrobacter polychromogenes* | LB-PBS (enriched) | LB |
| AE224 | *Pseudomonas otitidis* | CaCO3-water | LB |
| AE225 | *Bacillus cereus* | CaCO3-PBS | LB |
| AE226 | *Agromyces mediolanus* | BHI-PBS (enriched) | BHI |
| AE227 | *Agromyces mediolanus* | BHI-PBS (enriched) | BHI |
| AE228 | no ID | BHI-PBS (enriched) | BHI |
| AE229 | *Rhodococcus equi* | BHI-PBS (enriched) | BHI |
| AE230 | *Agromyces mediolanus* | BHI-water (enriched) | BHI |
| AE231 | *Agromyces mediolanus* | BHI-water (enriched) | BHI |
| AE232 | *Rhodococcus equi* | BHI-water (enriched) | BHI |
| AE233 | no ID | BHI-water (enriched) | BHI |
| AE234 | *Agromyces mediolanus* | BHI-water (enriched) | BHI |
| AE235 | *Agromyces mediolanus* | LB-water (enriched) | LB |
| AE236 | *Agromyces mediolanus* | LB-water (enriched) | LB |
| AE237 | *Agromyces mediolanus* | LB-PBS (enriched) | LB |
| AE238 | *Agromyces mediolanus* | LB-PBS (enriched) | LB |
| AE239 | *Arthrobacter polychromogenes* | LB-PBS (enriched) | LB |
| AE240 | *Agromyces mediolanus* | Blood-PBS (enriched) | BHI |
| AE241 | no ID | Blood-water (enriched) | BHI |
| AE242 | no ID | CaCO3-water (enriched) | LB |
| AE243 | *Arthrobacter polychromogenes* | CaCO3-PBS (enriched) | LB |
| AE244 | no ID | MHB-PBS (enriched) | MHB |
| AE245 | *Tsukamurella* species | Blood-PBS | BHI |
| AE246 | no ID | Blood-PBS | BHI |
| AE247 | *Tsukamurella* species | BHI-water (enriched) | BHI |
| AE248 | no ID | BHI-water (enriched) | BHI |
| AE249 | *Agromyces mediolanus* | Blood-water (enriched) | BHI |

TABLE 7-continued

List of cataloged endosymbiont strains and Biotyper identification.

| Strain name | Biotyper ID | Media for isolation | Grow In |
|---|---|---|---|
| AE250 | *Agromyces mediolanus* | CaCO3-PBS (enriched) | LB |
| AE251 | *Sphingomonas aerolata* | CaCO3-water (enriched) | LB |
| AE252 | no ID | MHB-PBS (enriched) | MHB |
| AE253 | no ID | MHB-water (enriched) | MHB |
| AE254 | no ID | CaCO3-PBS | LB |
| AE255 | *Paenibacillus glucanolyticus* | LB-water (enriched) | LB |
| AE256 | *Paenibacillus glucanolyticus* | LB-water (enriched) | LB |
| AE257 | *Paenibacillus glucanolyticus* | LB-water (enriched) | LB |
| AE258 | *Tsukamurella* species | Blood-PBS (enriched) | BHI |
| AE259 | *Gordonia rubripertincta* | Blood-water (enriched) | BHI |
| AE260 | no ID | CaCO3-PBS (enriched) | LB |
| AE261 | no ID | MHB-PBS (enriched) | MHB |
| AE262 | no ID | MOS-C3 clone #1 (Susi's) | LB |
| AE263 | no ID | MOS-C3 clone #2 (Susi's) | LB |

Example 5: Methods of Bacterial Isolation, Enrichment, Biotyping Methods

Bacterial Isolation from Mosquito Eggs May Include the Following Methods and Procedures:

1. Add mosquito eggs (Cd Hidalgo eggs) to coffee filter inside of 250 mL filter sterilizer;
2. Surface sterilize eggs by soaking them in 1% Tween 80 and 2% bleach solution for 3 mins then turn on vacuum to remove solution;
3. Rinse three times with sterile distilled water and let sit for 30 seconds each time before turning on vacuum;
4. Dry in hood in large petri dish;
5. Transfer dry eggs to sterile 1.5 mL microcentrifuge tube;
6. Homogenize eggs with a sterile tissue grinder in 1 mL of phosphate buffered saline (PBS) in 1.5 mL microcentrifuge tube. PBS pH 7.4 used for first set of eggs being plated on different concentrations of tryptic soy agar (TSA) plates (0.1% TSA, 1% TSA and 10% TSA), lysogeny broth (LB), and TSA+5% sheep blood agar.PBS pH 5 used for second set of eggs being plated on Glycerol growth media (GLY) plates;
7. Sonicate homogenized samples in PBS for 45 seconds;
8. Do dilution series in triplicate for homogenates by adding 200 µL of homogenate to first row of 96 well plate and then moving 20 µL into 180 µL of PBS for subsequent rows (dilutions will be neat through 10^-7);
9. Plate 100 µL of all dilutions and incubate at 28° C.;
10. Colonies will be counted and classified after 24, 48, and 72 hours of incubation;
11. Isolates of two representatives of each colony morphology will be purified to bank and store.

Bacterial Isolation with Enrichment from Mosquito Eggs May Include the Following Methods and Procedures:

1. Steps 1-11 above;
2. Add 1 mL of enrichment media to the remaining eggs and incubate at 28 C overnight. (Enrichment media is 1.5% peptone, 0.8% yeast extract, 1% D-glucose, 0.5% ethanol, 0.3% acetic acid, and 0.01% cyclohexamide in sterile milliQ water with pH adjusted to 3.5 with HCl.);
3. Next day, do dilution series in reps of 5 for enriched eggs by adding 150 µL of homogenate to first row of 96 well plate and then moving 20 µL into 180 µL of PBS (ph-5) for subsequent rows (dilutions will be neat through 10^-7);
4. Plate 10^-1 thru 10^-4 brain heart infusion agar (BHI), mueller hinton II agar (MHB), lysogeny broth agar (LB), tryptic soy agar+0.5% sheep blood, and calcium carbonate agar (CaCO3) plates and incubate at 28° C.; and
5. Isolates of two representatives of each colony morphology will be purified to bank and store.

Bacterial Biotyping May Include the Following Methods and Procedures:

1. Grow up bacteria the day before you'd like to work on the MALDI, for best results (2 days for bacteria grown at 30 C);
2. Using a sterile pipette tip, pick up one-three colonies of bacteria depending on size (be careful not to pick up any agar media) and smear it onto your desired target (for extra-large colonies only grab ½ colony). Complete the same for all samples. Complete each sample in duplicate or triplicate;
3. Apply 1 µl of 70% Formic Acid (FA) onto all spots (except BTS spots) and mix into bacteria a little. Let dry completely. (Do not use the outer border of the biotype plate);
4. Apply 1 µl of Standard (BTS) to 2-3 spots near your targets randomly dispersed through plate;
5. Apply 1 µl of α matrix HCCA (generated from refrigerated HCCA portion and 250 µl of 50% ACN, 2.5% TFA and vortexed until completely dissolved) onto all your targets, including the BTS target. Let dry completely before putting plate in Biotyper;
6. Make sure the MALDI is not in use and press "Out/In". Insert the biotyper plate into the open slot and gently close the door;
7. Open "Flex Control" program on the computer. Verify the selected method is "MBT_FC.par". Select your BTS spot and hit "Calibrate;"
8. When your BTS spot is acceptable, open the "Maldi Biotyper RTC" program.
9. Select "File", then "New Classification", then "Next" and find your project ID or make a new one. (Date_Initials_Project Number);
10. Next, select the spots on the biotyper plate that you have your samples on. Click "Add Analytes," and then choose "Bruker Taxonomy," then "Finish;"
11. It will take about 2 minutes per sample;
12. Press "Out/In" when finished, take the plate and press "Out/In" again;
13. When cleaning the Biotyper plate, use the harsh protocol; and
14. Calibrate MALDI.

Example 6: Feeding *Aedes aegypti* Adults *E. coli* Expressing DENV prM-Derived dsRNA Lowers Vector Competence for DENV-2

The present inventors demonstrated oral introduction of dsRNA-transformed bacteria, in this embodiment *E. coli*, to adult *Ae. aegypti* resulted in the inhibition of vector competence. In this embodiment specifically, the present inventors, determined that newly emerged adult *Ae. aegypti* may feed on a saline solution (BFS=150 mM NaCl, 10 mM NaHCO$_3$, 1 mM ATP) containing antibiotics and transformed *E. coli*. In this embodiment, the solution may contain 3% sucrose to help the mosquitoes to survive >48 hr. Green Fluorescent Protein (GFP) and Red Fluorescent Protein (RFP) expressing bacteria can be seen in both the midgut and the crop of dissected mosquitoes fed on solutions containing only saline-sugar. As a result, the present inventors demonstrated that *Ae. aegypti* may ingest a blood meal containing transformed *E. coli*; however, GFP expression is maintained in the midgut for only 24 hr post-feeding, and is not visualized 4 days after feeding, awaiting an additional DENV-containing blood meal.

In this embodiment, the present inventors raised Rear Poza Rica mosquitoes to adults. At 1 day post-eclosion (the act of emerging from the pupal case or hatching from the egg), the inventors feed all mosquitoes BFS w/ 3% sucrose, Carbenicillin 100 g/ml and Pen/Strep 100 U/ml and 100 g/ml, respectively, for 24 hr, then divided the mosquito populations into 6 groups of 100 female mosquitoes and feed for additional 48 hr as follows:

CONTROL 1: feeding solution only
CONTROL 2: feeding solution+HT115_GFPuv
CONTROL 3: feeding solution+HT115-GFPuv_Ptac_dsRNA-Luc
CONTROL 4: feeding solution+HT115-pGFPuv-T7-dsRNALuc
TREATMENT 1: feeding solution+HT115-pGFP_T7-dsRNADENV2 (DENV2 dsRNA under control of T7 promoter).
TREATMENT 2: feeding solution+HT115-pGFPuv-Ptac_dsRNADENV2 (DENV2 dsRNA under control of Ptac promoter).

After 48 hr continuous feeding, the present inventors provided all mosquitoes a DENV-2 infectious blood meal. Alternative embodiments may include the inclusion of respective *E. coli* strains in infectious blood-meals and continuation of provision of respective *E. coli*-feeding solutions daily for duration of experiment. The inventors proceeded to incubate randomly numbered TREATMENT and CONTROL mosquito groups for two weeks to allow DENV replication. Next, the inventors harvested and homogenized ¼ of surviving individual whole adult mosquitoes from each of the six groups to measure infectious DENV-2 in plaque assays at 36 hours, 72 hours, 7 days, and 14 days. (Complete plaque assay results shown in Tables 8-9 below).

TABLE 8

Summary of plaque assay results (no. inf./total, % pos.)

| Group | 36 h | 72 h | 7 day | 14 day | Totals |
|---|---|---|---|---|---|
| 1 | 0/3 | 2/4 (50%) | 4/4 (100%) | 2/4 (50%) | 8/15 (53%) |
| 2 | 0/3 | 9/9 (100%) | 8/8 (100%) | 7/9 (78%) | 24/29 (83%) |
| 3 | 0/5 | 6/7 (86%) | 4/6 (67%) | 4/7 (57%) | 14/25 (56%) |
| 4 | 0/4 | 4/11 (36%) | 5/9 (56%) | 5/12 (42%) | 14/36 (39%) |
| 5 | 0/3 | 0/5 (0%) | 1/3 (33%) | 0/4 (0%) | 1/15 (7%) |
| 6 | 0/3 | 3/11 (36%) | 9/9 (82%) | 9/10 (90%) | 22/33 (67%) |

TABLE 9

Infectious virus titer results for individual DENV-infected mosquitoes

| Group-sample no. | Avg. titer per mosquito (PFU) | | | |
|---|---|---|---|---|
| | 36 hr | 72 hr | 7 days | 14 days |
| 1-1 | <6.6 | <6.6 | >6.6 × 10$^2$ | >6.6 |
| 1-2 | <6.6 | >6.6 × 10$^2$ | >6.6 × 10$^1$ | <6.6 |
| 1-3 | <6.6 | <6.6 | >6.6 | >6.6 × 10$^1$ |
| 1-4 | nd | >6.6 | >6.6 × 10$^1$ | <6.6 |
| 2-1 | <6.6 | >6.6 × 10$^1$ | >6.6 × 10$^2$ | >5 × 10$^1$ |
| 2-2 | <6.6 | >6.6 × 10$^1$ | >6.6 × 10$^1$ | >6.6 × 10$^2$ |
| 2-3 | <6.6 | >6.6 | >6.6 | >6.6 × 10$^1$ |
| 2-4 | nd | >6.6 × 10$^1$ | >6.6 | >6.6 × 10$^2$ |
| 2-5 | nd | >6.6 × 10$^2$ | >6.6 × 10$^1$ | >6.6 × 10$^2$ |
| 2-6 | nd | >6.6 | >6.6 × 10$^1$ | <6.6 |
| 2-7 | nd | >6.6 | >6.6 | <6.6 |
| 2-8 | nd | >6.6 | >6.6 × 10$^2$ | >6.6 × 10$^1$ |
| 2-9 | nd | >6.6 × 10$^1$ | nd | >6.6 × 10$^2$ |
| 3-1 | <6.6 | >6.6 | >6.6 × 10$^1$ | >6.6 |
| 3-2 | <6.6 | >6.6 | >6.6 × 10$^2$ | <6.6 |
| 3-3 | <6.6 | >6.6 × 10$^1$ | >6.6 × 10$^1$ | <6.6 |
| 3-4 | <6.6 | >6.6 | >6.6 × 10$^2$ | >6.6 |
| 3-5 | <6.6 | >6.6 | <6.6 | <6.6 |
| 3-6 | nd | >6.6 | <6.6 | >3.3 × 10$^3$ |
| 3-7 | nd | <6.6 | nd | >6.6 × 10$^1$ |
| 4-1 | <6.6 | <6.6 | >6.6 × 10$^2$ | >5.3 × 10$^2$ |
| 4-2 | <6.6 | <6.6 | <6.6 | <6.6 |
| 4-3 | <6.6 | >6.6 × 10$^1$ | >6.6 | <6.6 |
| 4-4 | <6.6 | <6.6 | <6.6 | <6.6 |
| 4-5 | nd | >6.6 | >6.6 | <6.6 |
| 4-6 | nd | <6.6 | >6.6 × 10$^1$ | <6.6 |
| 4-7 | nd | >6.6 | <6.6 | >6.6 × 10$^2$ |
| 4-8 | nd | <6.6 | <6.6 | >6.6 × 10$^2$ |
| 4-9 | nd | >6.6 | >6.6 | <6.6 |
| 4-10 | nd | <6.6 | nd | >6.6 × 10$^1$ |
| 4-11 | nd | <6.6 | nd | >6.6 × 10$^1$ |
| 4-12 | nd | nd | nd | <6.6 |
| 5-1 | <6.6 | <6.6 | >6.6 × 10$^1$ | <6.6 |
| 5-2 | <6.6 | <6.6 | <6.6 | <6.6 |
| 5-3 | <6.6 | <6.6 | <6.6 | <6.6 |
| 5-4 | nd | <6.6 | nd | <6.6 |
| 5-5 | nd | <6.6 | nd | nd |
| 6-1 | <6.6 | <6.6 | >6.6 × 10$^2$ | <6.6 |
| 6-2 | <6.6 | <6.6 | >6.6 | >6.6 |
| 6-3 | <6.6 | >6.6 × 10$^1$ | >6.6 × 10$^1$ | >6.6 × 10$^1$ |
| 6-4 | nd | <6.6 | >6.6 | >6.6 × 10$^1$ |
| 6-5 | nd | <6.6 | >6.6 | >6.6 × 10$^1$ |
| 6-6 | nd | <6.6 | >6.6 × 10$^1$ | >6.6 × 10$^2$ |
| 6-7 | nd | >6.6 × 101 | >6.6 × 10$^1$ | >6.6 |
| 6-8 | nd | >6.6 | >6.6 × 10$^1$ | >6.6 × 10$^2$ |
| 6-9 | nd | <6.6 | >6.6 × 10$^1$ | >6.6 |
| 6-10 | nd | <6.6 | nd | >6.6 |
| 6-11 | nd | >6.6 × 10$^1$ | nd | nd |

The inventors took individual whole adult *Ae. aegypti* from each of 6 randomly-numbered groups in Trial 1, which had/had not been fed DENV dsRNA-expressing transformed *E. coli*, and assayed for infectious virus content. Each mosquito was homogenized in 1 ml cell culture growth medium and filtered. Ten-fold dilutions were prepared from $10^0$ to $10^{-5}$ and 0.15 ml of each dilution was plated on Vero cell monolayers in triplicate for plaque assays. Survivors/group varied from 15 to 36; group numbers were randomly assigned. Detection of infectious virus in 16 mosquito homogenates immediately post blood meal: (11/16 Positive and 5/16 Negative).

Example 7a: Identification of ZIKV RNA-Derived dsRNA for RNAi Targeting

The present inventors, in one embodiment, demonstrate the identification of dsRNA for RNAi targets on Zika virus genome by genome sequence alignments. To identify specific dsRNA effector molecule(s) for inhibition of infection and transmission by multiple strains of Zika virus (ZIKV) in Ae. aegypti when expressed by transformed bacterial endosymbionts, the present inventors first aligned full-length nucleotide sequences of 21 ZIKV genomes. Average diversity among the coding regions was found to be 13.9%. Sequence diversity is lower than average for the 2680 nt region spanning genes NS2B-NS3-NS4A (see Table 10).

Figure 9A:
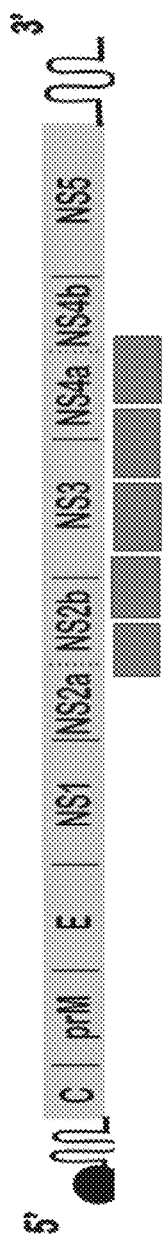
FIG. 9A-B: a.) Genome organization of the ~11 kb genome of ZIKV. Red lines indicate target regions for si-RNA-mediated silencing. Sequences (520-580 nt in length) derived from the 6 different target regions may be arranged in sense and antisense orientations separated by the small intron of the *Ae. aegypti* Sialokinin 1 gene, which generates principal vasodilatory peptide, to form IR constructs, which act as sequence homology-dependent RNAi triggers. b.) Zika virus genome organization. Zika has a single-stranded, positive-sense RNA genome of approximately 10.8 kilobases. C=capsid; prM=prec with each element alone, and also with any and all various permutations and combinations of all elements in this or any subsequent application.
Figure 9B:
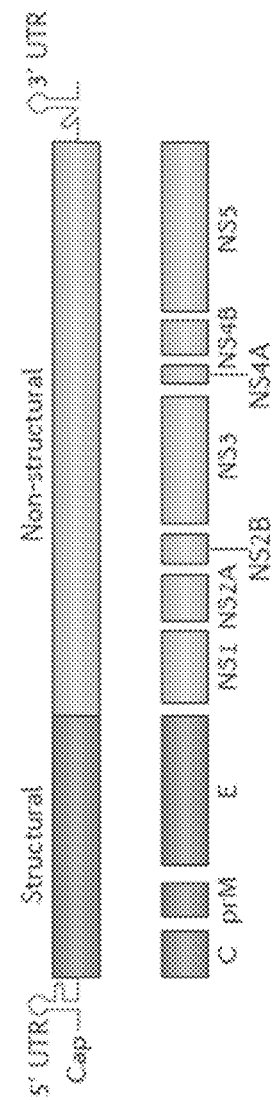

Nucleotide sequence alignments of the full-length genomes of 21 ZIKV (Zika virus) isolates from Africa, Asia, and the Americas show that the average diversity among the coding regions is 13.9%. Sequence diversity is lower than average for C, NS2B-NS3-NS4A (Table 10). Capsid (C) is not an ideal RNAi target because it is a relatively short coding region and is located adjacent to the highly structured 5' untranslated region (UTR). The present inventors have instead identified and tested dsRNA sequences from the 2680 nt region spanning NS2B-NS3-NS4A with relatively low sequence diversity as an optimal viral inhibition target (see FIG. 9A-B).

TABLE 10

ZIKV genome sequence diversity based on 21 genome coding sequences from African and Asian lineages.
C = capsid, prM/M = pre-membrane/membrane,
E = envelope, NS1-5 = nonstructural proteins 1-5

| Gene | nt start | nt end | nt size | nt diversity % | aa size |
|---|---|---|---|---|---|
| C | 107 | 472 | 365 | 9.6 | 122 |
| prM/M | 473 | 976 | 503 | 14.7 | 168 |
| M | 752 | 976 | 224 | 16.5 | 75 |
| E | 977 | 2476 | 1499 | 14.7 | 500 |
| NS1 | 2477 | 3532 | 1055 | 13.3 | 352 |
| NS2A | 3533 | 4210 | 677 | 15.8 | 226 |
| NS2B | 4211 | 4660 | 449 | 11.6 | 150 |
| NS3 | 4601 | 6451 | 1850 | 12.5 | 617 |
| NS4A | 6452 | 6832 | 380 | 12.9 | 127 |
| NS4B | 6902 | 7654 | 752 | 14.2 | 251 |
| NS5 | 7655 | 10363 | 2708 | 16.9 | 903 |

Figure 10:
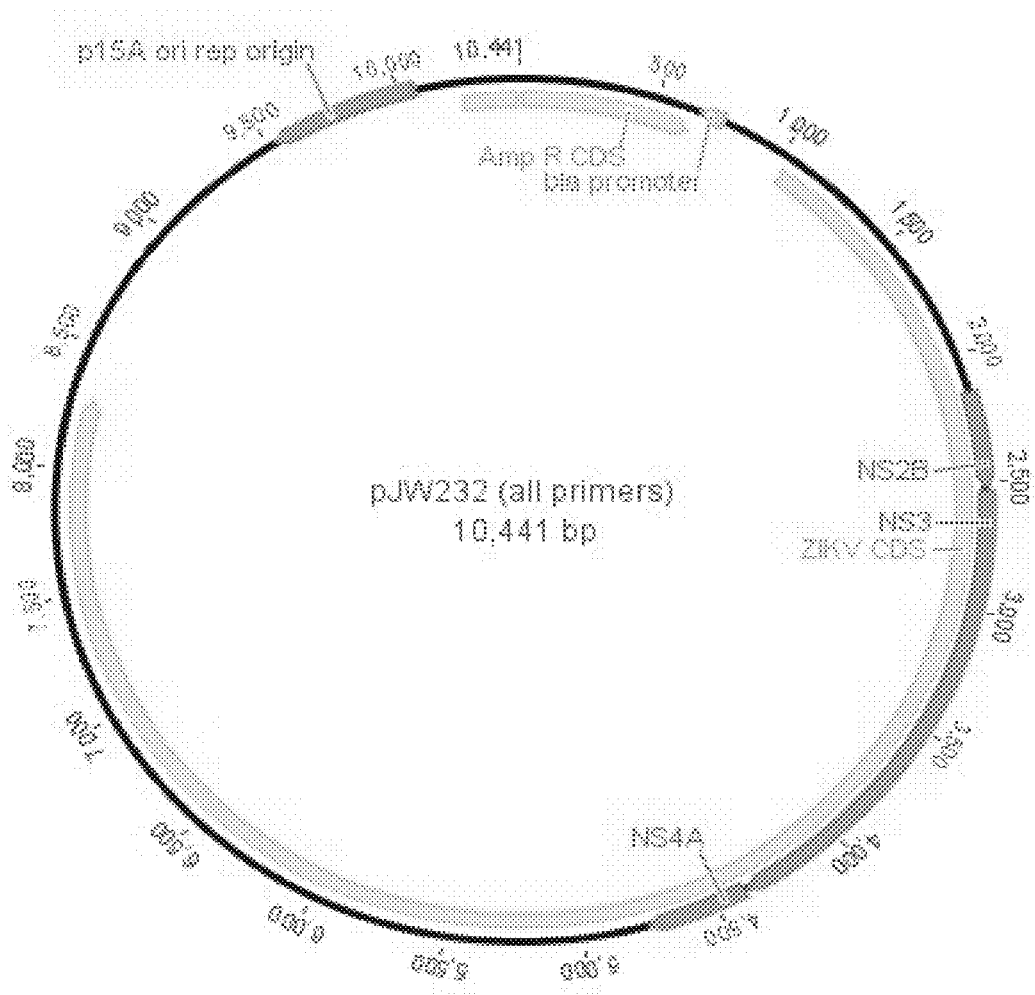
Figure 11:
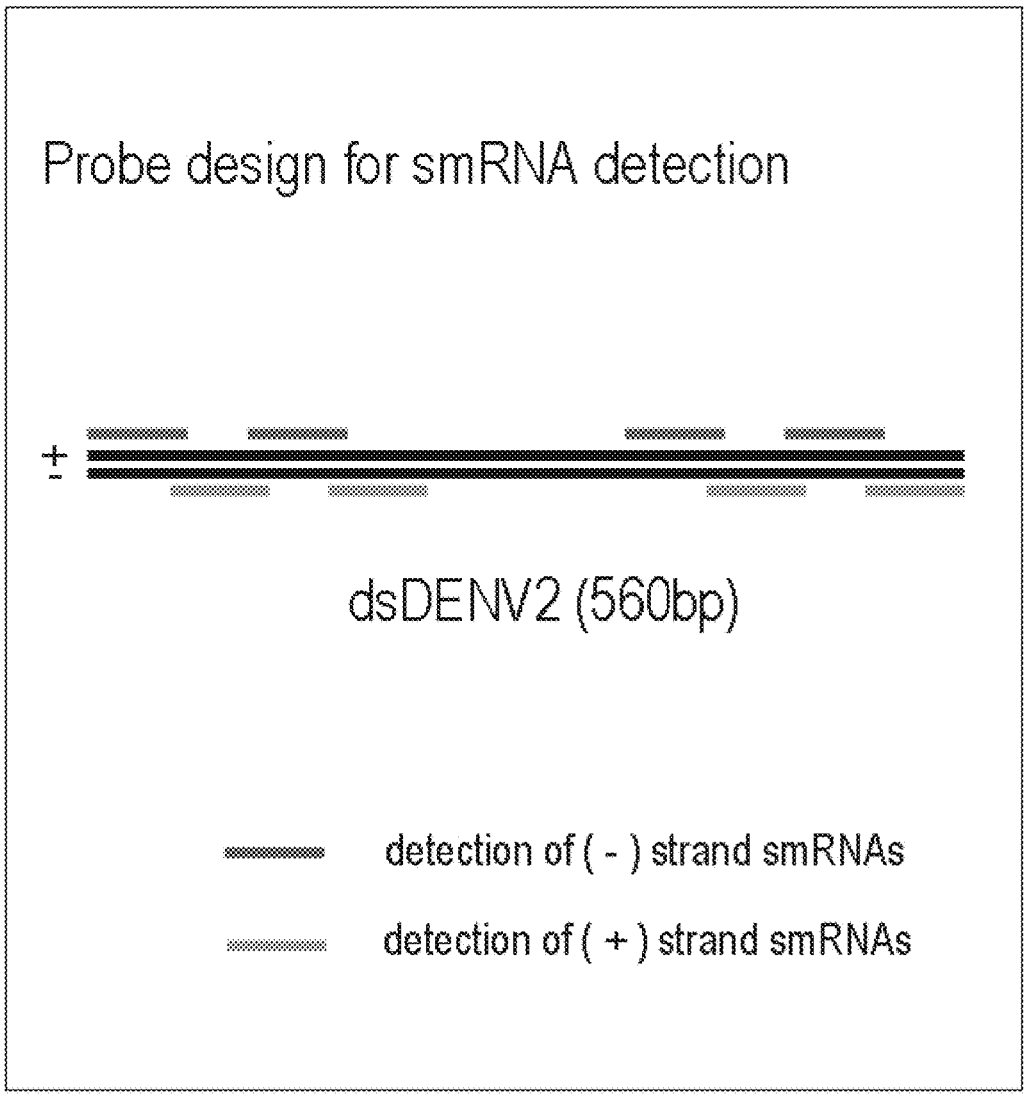
Figure 12:
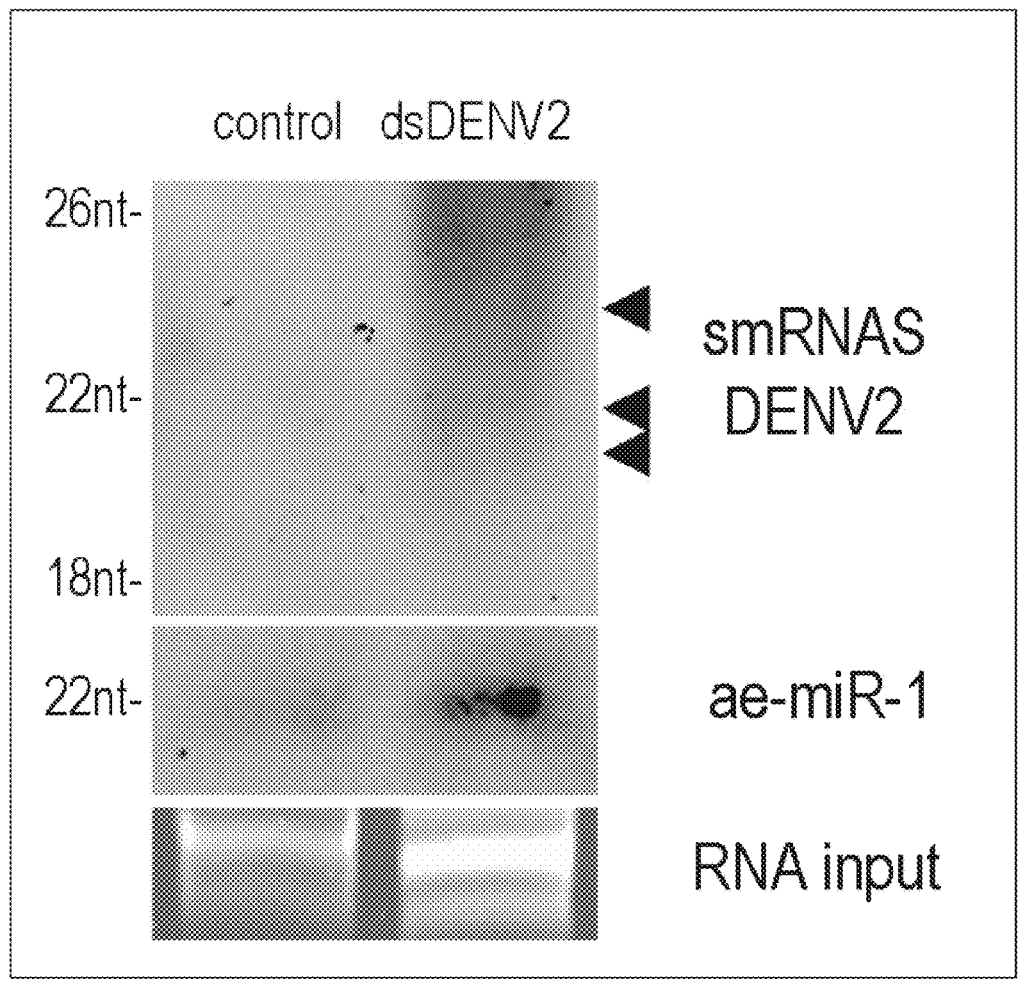

Based on this sequence identity, the inventors tested anti-viral activity in mosquitoes (Ae. aegypti Poza Rica) of 5 dsRNAs (>530 bp each) derived from the NS2B-NS4A. (FIG. 9A-B) Specifically, in this embodiment, the present inventors tested anti-viral activity in mosquitoes (Ae. aegypti Poza Rica) of 5 dsRNAs (>530 bp each) derived from the NS2B-NS3-NS4A region (Table 10, and FIG. 10). As a note: the prM/M sequence of DENV2 targeted by dsRNA expressed in Carb109M mosquitoes has a higher sequence diversity among DENV2 genotypes (>13%) than dsRNAs derived from ZIKV NS2B-NS3-NS4A region.

The present inventors generated cDNA templates for in vitro transcription of dsRNA which were amplified from the conserved NS2B-NS4A genes of the ZIKV PRVABC59 infectious cDNA clone. Specific primers incorporating bacteriophage T7 promoter sequences at each 5' end were designed to amplify 5 DNA fragments of 530-580 bp by PCR. The dsRNA was generated by in vitro transcription of this DNA with T7 RNA polymerase. Successfully-produced dsRNA was analyzed for efficacy in suppression of virus infection. The present inventors demonstrated that, at 5 days post-emergence, 40 Ae. aegypti females were injected intrathoracically with 250 ng of each dsRNA. Two days later, injected females were given blood-meals containing ZIKV at $5 \times 10^6$ PFU/ml. Virus titers in whole-bodies of mosquitoes were determined by plaque assays in Vero cells at 7 and 14 days post-infectious blood-meal (pbm). Non-injected or dsRNA β-Gal (non-target control)-injected mosquitoes were used as controls. (see Table 11 below).

TABLE 11

Virus titer and proportion of ZIKV infected mosquitoes 7 and 14 days post blood-meal.

| Group | Treatment | 7 day avg titer (PFU/mosq) | 7 day inf/tot (%) | 14 day avg titer (PFU/mosq) | 14 day inf/tot (%) |
|---|---|---|---|---|---|
| 1 | no injection | $1.70 \times 10^4$ | 12/24 (50) | $7.6 \times 10^5$ | 4/24 (17) |
| 2 | PBS | $5.70 \times 10^3$ | 12/24 (50) | $1.30 \times 10^5$ | 2/24 (8) |
| 3 | RNA 1 | $4.40 \times 10^3$ | 2/24 (8) | <10 | 0/24 (0) |
| 4 | RNA 2 | <10 | 0/24 (0) | <10 | 0/24 (0) |
| 5 | RNA 3 | <10 | 0/24 (0) | $4.7 \times 10^3$ | 1/24 (4) |
| 6 | RNA 4 | $5.40 \times 10^3$ | 2/24 (8) | <10 | 0/24 (0) |
| 7 | RNA 5 | $4.40 \times 10^2$ | 2/24 (8) | <10 | 0/24 (0) |
| 8 | β-gal RNA | $1.00 \times 10^4$ | 7/24 (29) | $1.2 \times 10^5$ | 8/24 (33) |

Treatment groups: 1) non-injected control, 2) PBS injection, 3-7) dsRNA from ZIKV genome regions 1-5 (see Table 11, and FIG. 8) β-gal dsRNA. Each of the 5 ZIKV dsRNA treatments targeted slightly overlapping ~500-bp regions of the conserved NS2B-NS4A genes of the ZIKV-PRVABC59 infectious cDNA clone. The present inventors demonstrated that all dsRNAs tested were effective in reducing ZIKV titers in infected *Ae. aegypti*, with RNA2 (557 bp) showing greatest effectiveness. All dsRNAs, in alternative embodiments, may be applied to reducing titers in additional ZIKV strains.

Example 7b: Identification of ZIKV RNA-Derived dsRNA for RNAi Targeting of 3 Major ZIKV Strains The present inventors demonstrated that the dsRNAs tested were effective in reducing ZIKV infection rates and infectious virus titers in infected *Ae. aegypti*, with only RNAs 2 showing effectiveness with all three ZIKV genotypes. As generally shown in FIGS. 17-18, the present inventors demonstrated that at 5 days post-emergence, 40 *Ae. aegypti* Poza Rica females were injected intrathoracically with 250 ng of each dsRNA. Two days later, injected females were given blood-meals containing one of three ZIKV genotypes at $10^8$ PFU/ml. These genotypes were: PRVABC59, 41525 (West Africa) and MR677 (East Africa). Virus titers in whole-bodies of mosquitoes were determined by plaque assays in Vero E6 cells at 7 and 14 days post-infectious blood-meal (dpi). Non-injected or dsRNA β-Gal (non-target control)-injected mosquitoes were used as controls.

Generally, African strains of ZIKV, particularly the West African strain 41525, grow more robustly in both human and mosquito cultured cell lines and are more efficiently transmitted by the *Aedes aegypti* Poza Rica strain. Accordingly, as generally shown in FIGS. 17-18, the blood-meal titer of ZIKV 41525 was much higher than would be expected in a natural blood-meal. Nevertheless, we showed that IT injection of certain ZIKV dsRNAs, particularly #1 and #5, resulted in significantly reduced viral titers and proportion of mosquitoes infected for all 3 ZIKV strains.

Example 8: Bacterial Secretion of Plasmid Encoded dsRNA

The present inventors demonstrated that the plasmid encoded dsRNA is secreted from selected transformed bacteria. In this embodiment, *E. coli* strains with and without plasmids encoding various dsRNA constructs were gown in Luria broth media and screened for the secretion of dsRNA. In this embodiment, the following, exemplary bacterial strains were tested for secretion of specific dsRNA into the growth media.

- HT115-harboring a puc19 plasmid encoding the T7 promoter driven expression of dsRNA-GFP
- HT115-harboring a puc19 plasmid encoding the T7 promoter driven expression of dsRNA-Luc (Luc=luciferase; negative control)
- HT115 without plasmid Additional embodiments may utilize a variety of transformed bacterial species, strains and the like. Following grow out, the bacteria were removed from the filtrate using a 0.2 um filter and dsRNA was extracted from filtrate using a 5-min dsRNA extraction kit provided by Biofactories. The dsRNA-GFP was used as the template for cDNA synthesis using GFP-specific PCR primers. The T7-GFP strain and isolated plasmid DNA was used as a PCR positive control. A PCR product of the expected size (419 bp) was detected in the filtrate from HT115-T7-dsGFP but not in either the empty vector strain HT115 or from the HT115-puc19-DL filtrates. (see FIG. 8) These results demonstrate secretion of dsRNA from the bacteria. This secreted dsRNA may, for example, be taken by other cells through endocytic, vesicular trafficking, phagocytosis and/or other processes.

Example 9: Detection of siRNA-DENV2 in Mosquitoes being Fed Bacteria Expressing dsRNA DENV2

The present inventors demonstrate the delivery of dsRNA-Dengue to mosquitoes and its processing to siRNA. Additional embodiments may include dsRNA from a variety of mosquito borne pathogens. In this embodiment, the present inventors fed mosquitos with sugar and HT115 bacteria expressing dsDENV2, or only sugar (control). HT115-dsDENV2 bacteria were also provided to mosquitoes in water cups. Twenty mosquitos from each treatment were sacrificed after 3 days and frozen.

Small RNAs from the whole body of the 20 mosquitoes were isolated using the mirVANA miRNA isolation kit (Ambion-ThermoFisher) following the enrichment procedure for small RNAs. Specifically, 1-2 ug of enriched small RNA samples from both control and HT115-dsDENV2 bacteria fed mosquitos were resolved by polyacrylamide gel electrophoresis and transferred to a positively charged membrane. The membrane was hybridized overnight at 38° C. in PerfectHyb+ buffer (Sigma) with 3'-end DIG-labelled 45 nt DNA oligonucleotide probes homologous to both strands of the dsRNA DENV2 precursor (FIG. 11). Following high stringency washes the membrane was incubated with anti-DIG AP antibody (1:10,000) for 1 hour at room temperature. CDP-star (Roche) was used as chemiluminescent substrate for detection and imaging performed with a Gel Doc MP system (Bio-Rad). As control, a replicate membrane was hybridized with DIG labeled oligo antisense to mosquito miR-1.

The present inventors demonstrated that discrete bands in the 21-24 nt range were observed in the dsDENV2 sample indicating that bacterial transcribed dsRNA DENV2 is transferred to the Mosquito and is a substrate for DICER-mediated cleavage in the host mosquito. No hybridization signal was observed in the control sample (FIG. 12).

Example 10: Detection by RNAseq of DENV2-Specific siRNAs in Mosquitoes Treated with Bacteria Expressing dsRNA Against DENV2

The present inventors demonstrated the presence of siRNAs in mosquitos introduced to bacteria expressing dsRNA targeted to DANV2. The present inventors fed mosquitos with sugar and HT115 bacteria expressing dsRNA against DENV2 (dsDENV2) or sugar only (control). Mosquitoes were fed with blood meal and immediately after they were frozen. Total RNA was extracted from whole bodies of 20 mosquitoes using the mirVANA miRNA isolation kit (Ambion-ThermoFisher) following the manufacturers' instructions. 2 ug of total RNA was shipped in dry ice to NCGR for small RNA sequencing. Total RNA samples were gel-fractionated and small RNAs (<100 nt) were osmotically isolated from gel slices.

Libraries were prepared for the two samples (hereby BmRNA=control, dsRNA=dsDENV2) using the Illumina TruSeq small RNA library prep kit. qPCR was performed in each sample for optimal read distribution. Sequencing was performed on a Illumina HiSeq 2500 on a 1×50 nt. Small RNA adapters were trimmed with Cutadapt 1.14. Trimmed reads were filtered by length (16-32 bps). Reads were aligned to DENV2-Jamaica 1409 strain with Bowtie allowing for 0 mismatches. FIG. 16 generally shows the alignment of reads that correspond to the region of DENV2 that dsRNA targets (red rectangle). As generally shown in the figures, the present inventors demonstrated a significant difference between the control (BmRNA) and the sample dsRNA. This shows that the dsRNA that was produced in bacteria populating the mosquito midgut is able to enter the mosquito gut epithelial cells. Subsequently it was processed by Dicer into siRNA and loaded on the mosquito RISC complex.

Example 11: Suppression of Viral-Expressed Green Fluorescent Protein (GFP) in Mosquitos Infected with E. coli Expressing dsRNA-eGFP The present inventors generated an exemplary Sindbis virus to express the green fluorescent protein, eGFP (MRE16 virus). Sindbis viruses are enveloped particles with an icosahedral capsid. Its genome is a single stranded RNA approximately 11.7 kb long. It has a 5' cap and 3' polyadenylated tail therefore serves directly as messenger RNA (mRNA) in a host cell. The genome encodes four non-structural proteins at the 5' end and the capsid and two envelope proteins at the 3' end.

The present inventors demonstrated that bacterial encoded dsRNA-eGFP could be delivered to adult mosquitoes and silence the MRE16 viral encoded eGFP, mosquitoes preinfected with E. coli expressing the dsRNA-eGFP or not were either injected with MRE16 virus or fed MRE16 virus (titer=8.37 logs) in a blood meal and the resultant eGFP fluorescence, or lack thereof quantified.

Here, E. coli, either not expressing a dsRNA-eGFP construct, or expressing a dsRNA-eGFP construct designed to silence the MRE16 encoded eGFP were fed 5 days prior to injection or feeding a blood meal with MRE16 virus. Then, eGFP fluorescence levels were scored 4 days post infection (dpi) with the virus. Treatment with of bacteria resulted in approximately 5-50 total viruses remaining in mosquitoes after a blood meal with MRE16 virus expressing eGFP versus 100,000 viruses in the controls. This variation (5-50 viruses in mosquitoes preinfected with the bacteria) in viral load may reflect different levels of bacterial infection in each mosquito which ranged from 320-1450 bacteria per mosquito.

Figure 13:
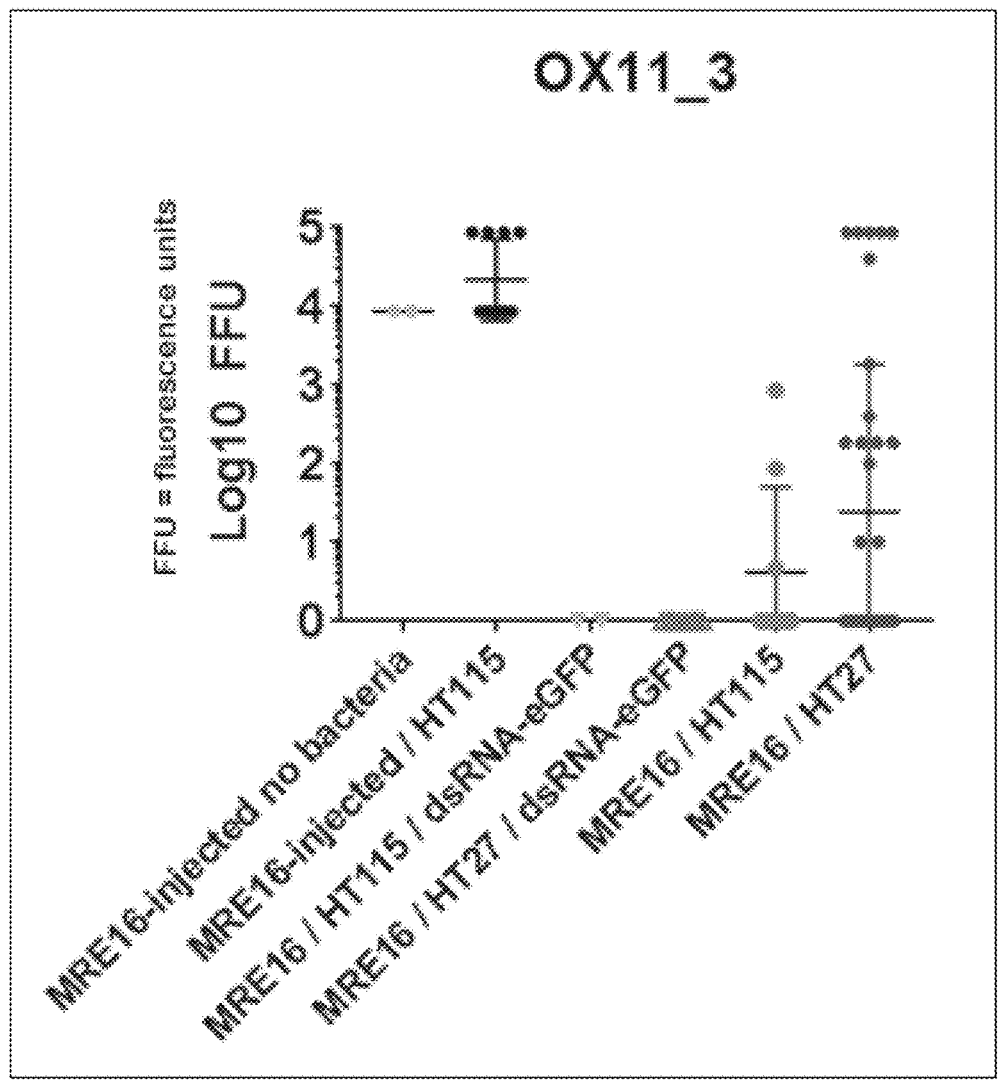

The present inventors demonstrate a five log-fold reduction, or 100,000-fold relative to no bacteria control, in eGFP fluorescence level was observed in adult mosquitoes pre-infected with two different E. coli strains, (see FIG. 13: HT115=RNAse III mutant; HT27=RNase III mutant and amino acid auxotroph mutant) expressing dsRNA-eGFP (see columns 5 and 6 in FIG. 13) and infected with MRE16 viruses in a blood meal relative to mosquitoes injected only with MRE16 viruses (column 1 in FIG. 13), or pre-infected with E. coli not expressing dsRNA-eGFP (column 2 in FIG. 13) and injected with MRE16 virus. Mosquitoes pre-infected with E. coli, again strains HT115 and HT27, expressing dsRNA-eGFP and injected with dsRNA-eGFP (400 ng) were also injected with MRE16 virus to determine maximum possible extent of suppression of eGFP expression (no FFU) and are shown in columns 3 and 4 in FIG. 13. These mosquitoes expressed no eGFP.

Figures 14A, 14B:
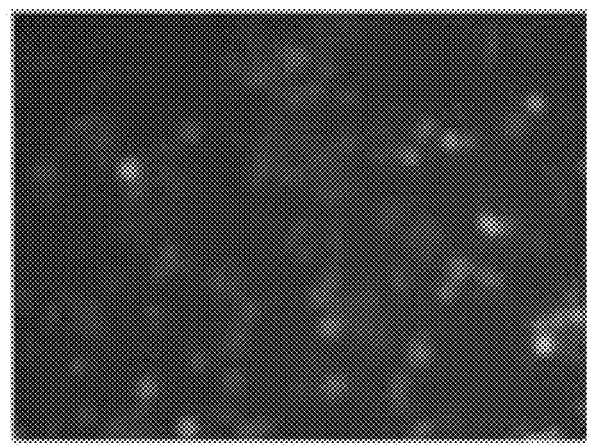
Figure 15:
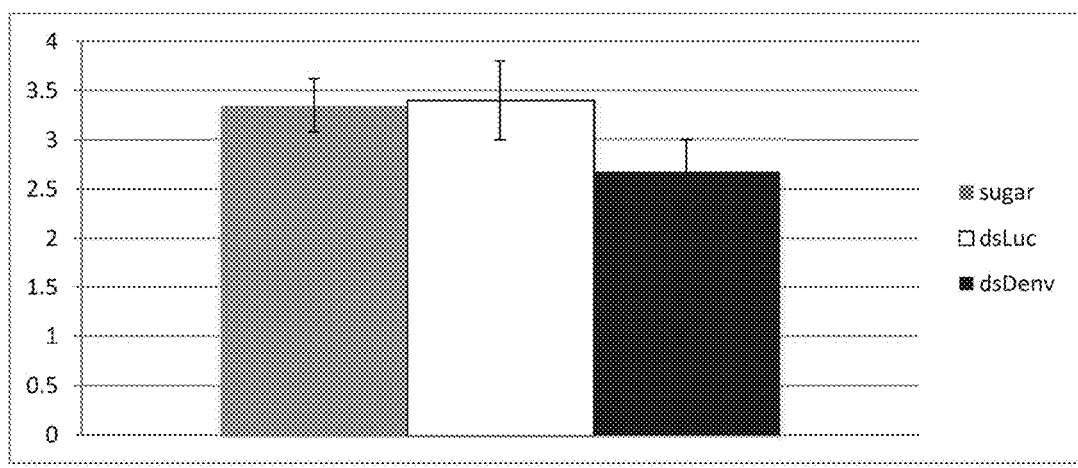
Figure 16:
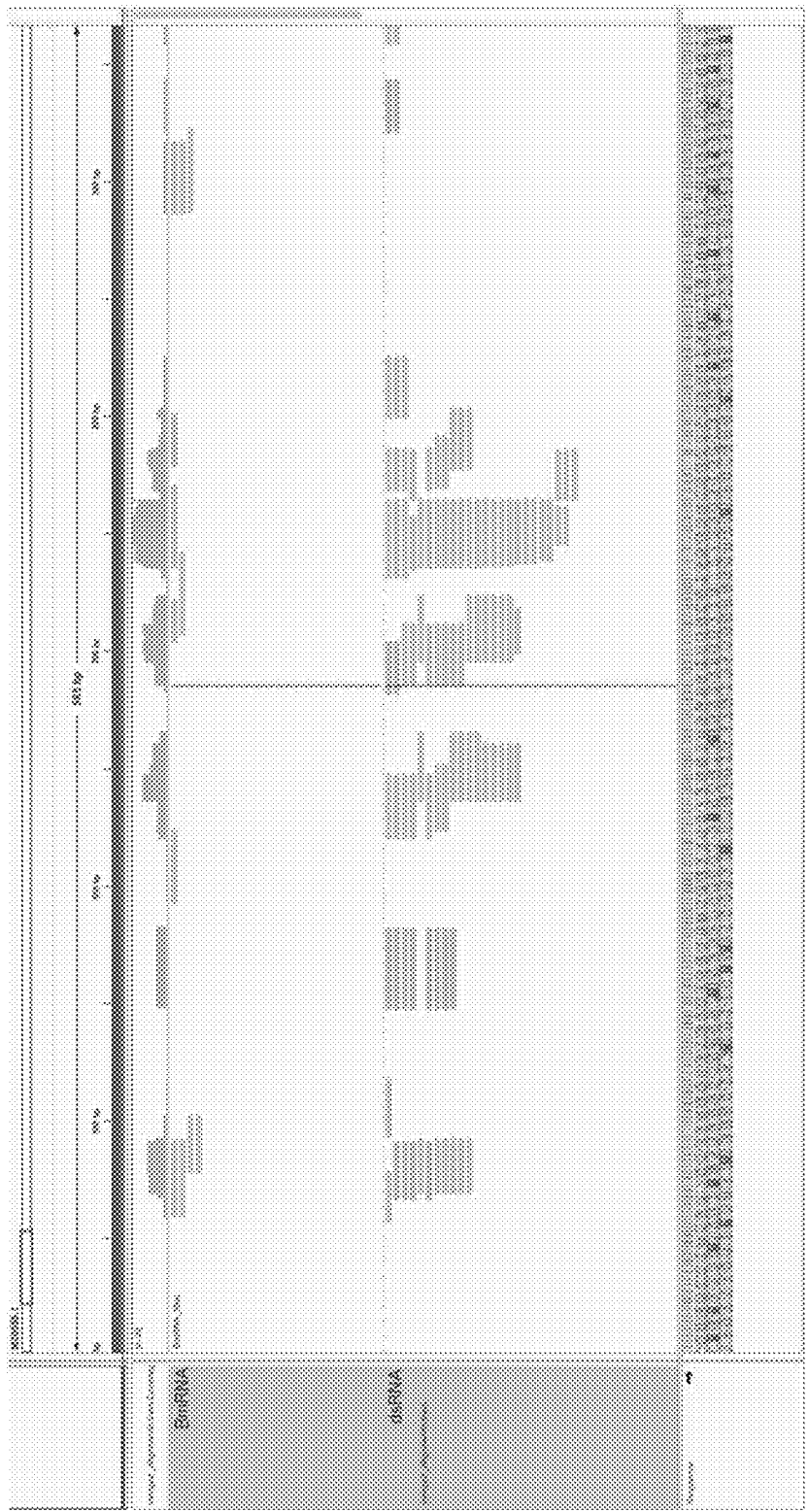
Figure 18:
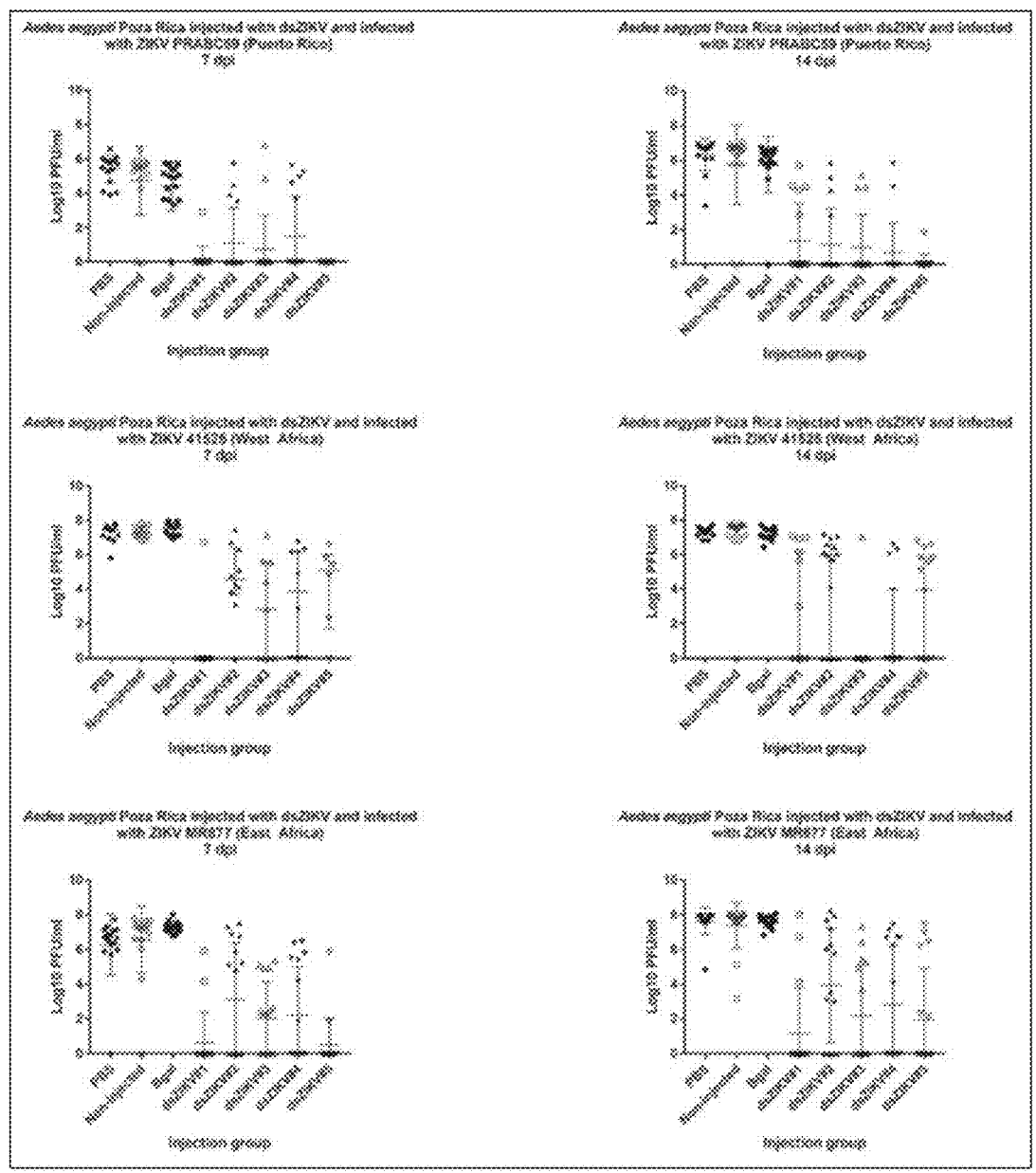
Figure 19A:
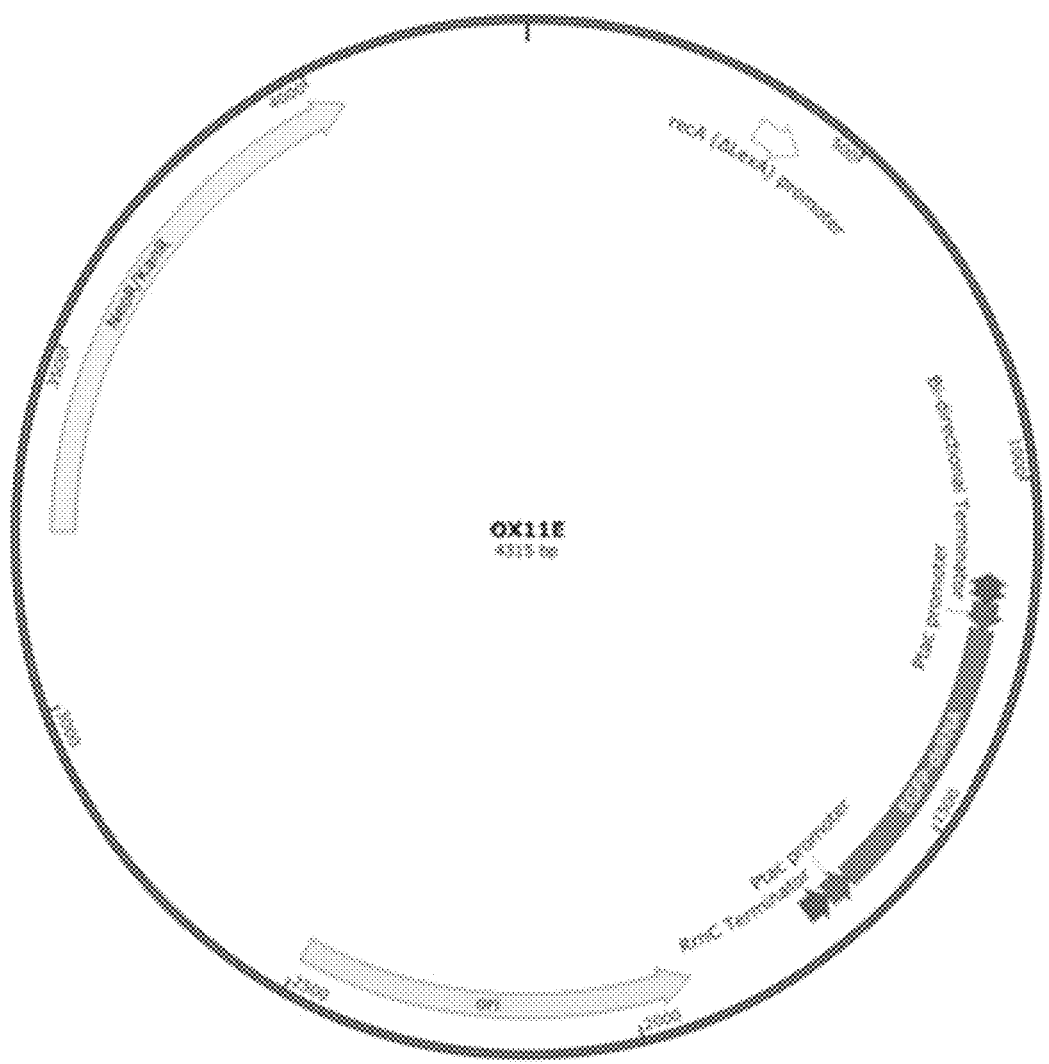
Figure 19B:
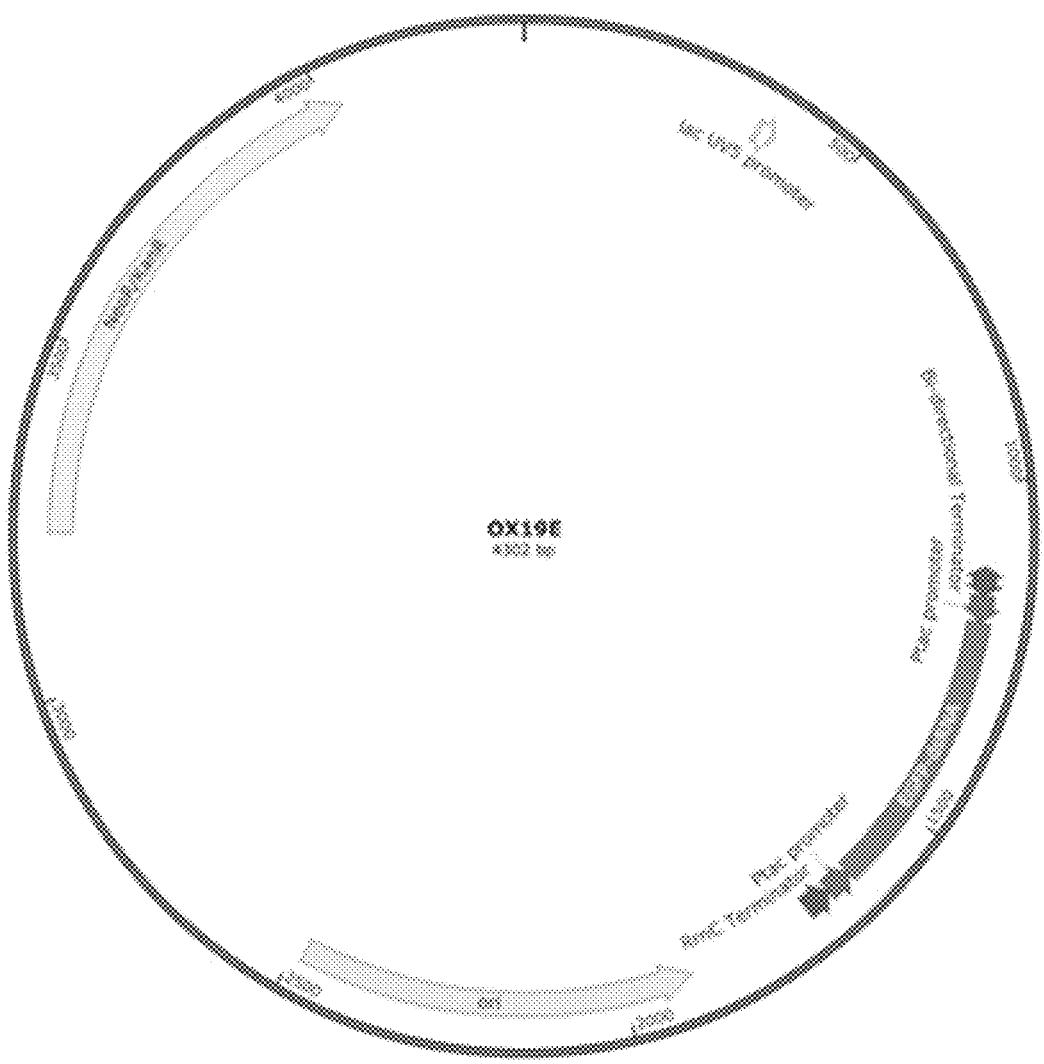
Figure 19C:
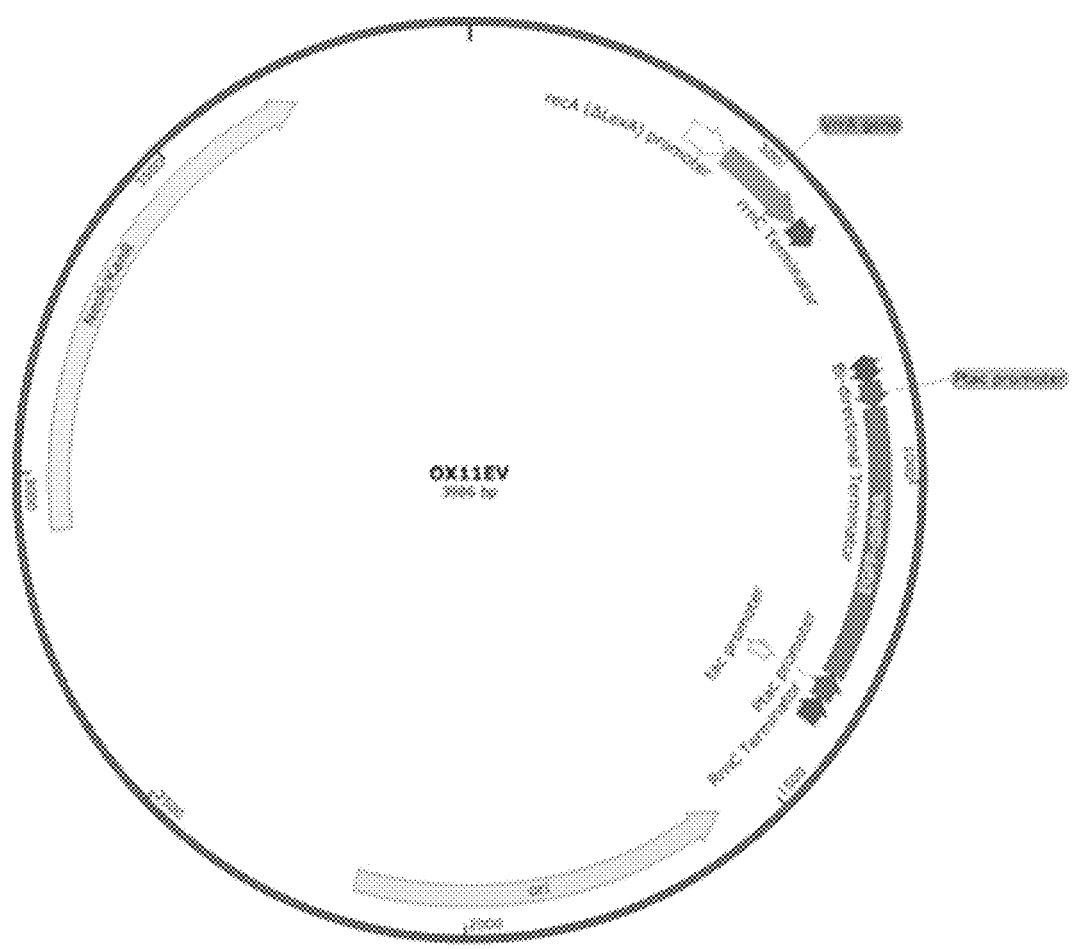
Figure 19D:
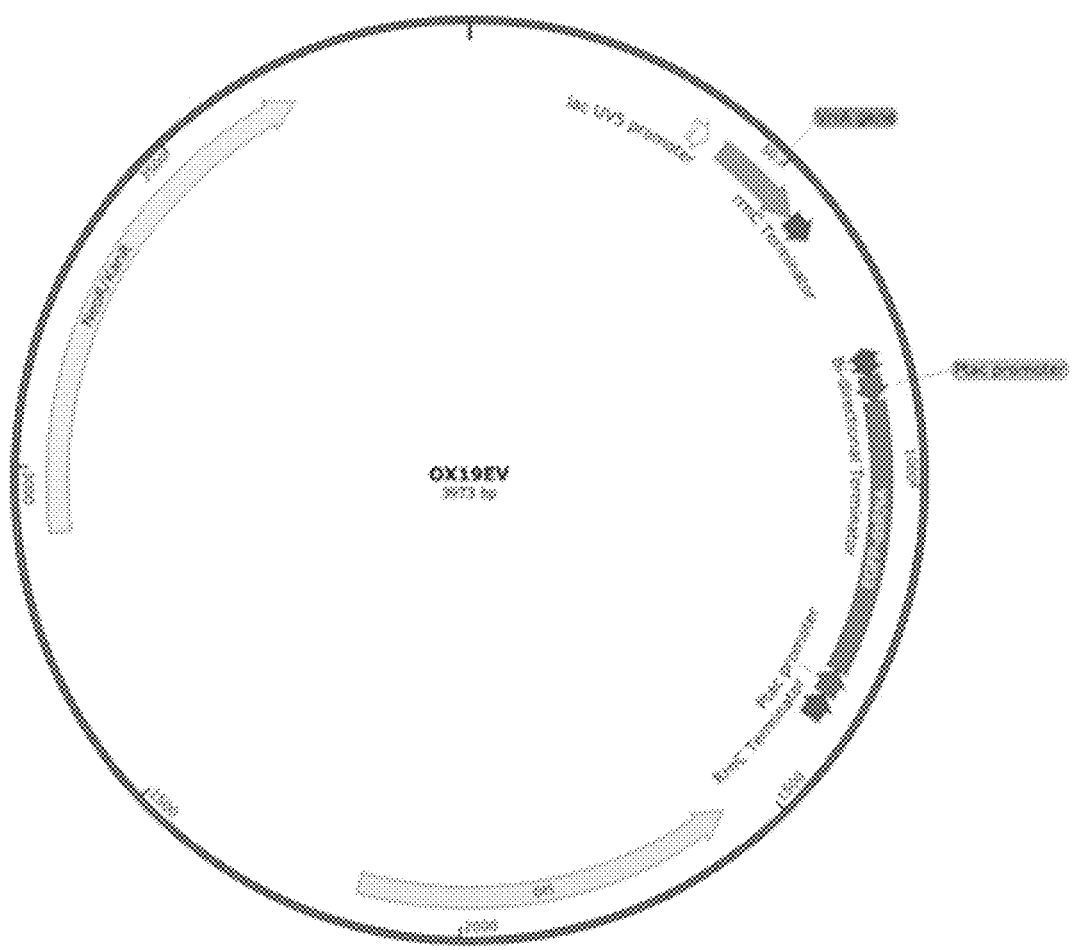

In a separate experiment shown in FIG. 14A-B, it is demonstrated that naked dsRNA-eGFP (400 ng) injected into mosquitoes immediately after a blood meal with MRE16 viruses can suppress eGFP expression unlike injection with a non-targeted dsRNA-Bgal (400 ng). Overall, these results demonstrate delivery of dsRNA-eGFP from E. coli (HT115 or HT27) expressing dsRNA-eGFP to the mosquito resulting in the silencing of the MRE16 encoded eGFP gene. The picture in the FIG. 14A, demonstrates the remaining viruses in mosquitoes treated with our bacteria as small dots. The control (no dsRNA-eGFP expressing bacteria) would be solid green if shown due to quantity of the virus present. In one preferred embodiment, the results demonstrate enteric bacterial delivery of dsRNA to silence a viral encoded gene.

Example 12: Suppression of Viral-Expressed Green Fluorescent Protein (eGFP) in Mosquitoes Infected with E. coli Expressing dsRNA-eGFP The present inventors demonstrated that HT27 show reduced infection rates at 4 dpi in comparison with HT115 and that at 7 dpi helper gene VrrA contributes significantly to the viral suppression. The present inventors evaluated the performance of two E. coli cell lines, HT115 and HT27. Both strains are RNase III deficient, which prevents degradation of expressed dsRNAs. In addition, HT27 is a double nutritional auxotroph (histidine and isoleucine). Bacteria with nutritional auxotrophies are able to form structures called nanotubes. These nanotubes connect bacteria with complimentary auxotrophies thus complimenting each other's nutritional dependencies. It has been shown that through these nanotubes a variety of biomolecules can be exchanged including proteins through interconnecting cells. In addition, the present inventors evaluated the performance of a non-coding small RNA, called VrrA. VrrA was first identified in Vibrio cholera and it was shown to increase secretion of outer membrane vesicles (OMVs) by downregulating OmpA. OMVs have been shown to contain a variety of biomolecules, including RNA and play a role in bacteria-bacteria and bacteria-host interactions.

As before, adult mosquitoes were provided with a bloodmeal containing a 1:2 dilution of 5'dsMRE16-eGFP in a water-jacketed feeding apparatus. A portion of each bloodmeal was reserved for viral titration. Mosquito bloodmeals averaged about 6.6 logs/mL. Engorged mosquitoes were removed and held for 4 and 7 dpi, when they were scored for eGFP fluorescence under an Olympus fluorescence stereoscope with a FITC channel filter.

Virus titrations were performed using the Karber method as above. Baby hamster kidney-15 (BHK) cells at 2×105 cells/ml were seeded into 96 well flat bottom plates at 100 µl per well. Cells were cultured in Modified Eagle's medium (MEM), 7% fetal bovine serum, 100 g/ml penicillin/streptomycin, 0.5 µg/ml amphotericin B and 50 µg/ml gentamicin. Mosquitoes were homogenized in 400 µl of the same medium and homogenized using a Qiashredder (Qiagen) at full speed for 30 seconds. Samples were diluted into ten-fold serial dilutions in medium plus supplements, and 100 ul of each sample, in triplicate, were added to BHK cells. Cytopathic effects and eGFP fluorescence were scored at 3 dpi.

As shown in FIGS. 19A-D, exemplary plasmids were used in the above experiment. OX11 and OX19 vectors are identical except of the promoter at the MCS. dsRNA against eGFP (designated E in the plasmids name is cloned in these two plasmids in each own cassette and regulatory elements (promoters and terminators), therefore OX11E and OX19E can be considered essentially identical, all data figures show combined results for OX11 and OX19 effectors. Therefore, the effectors OX11_E and OX19_E will be referred to as OXE. VrrA (designated V) is cloned downstream of the respective MCS promoters of OX11 and OX19, therefore OX11EV is a different construct than OX19EV. The promoter of OX11 is of medium strength whereas the promoter of OX19 is stronger than the OX11 promoter.

Figure 20:
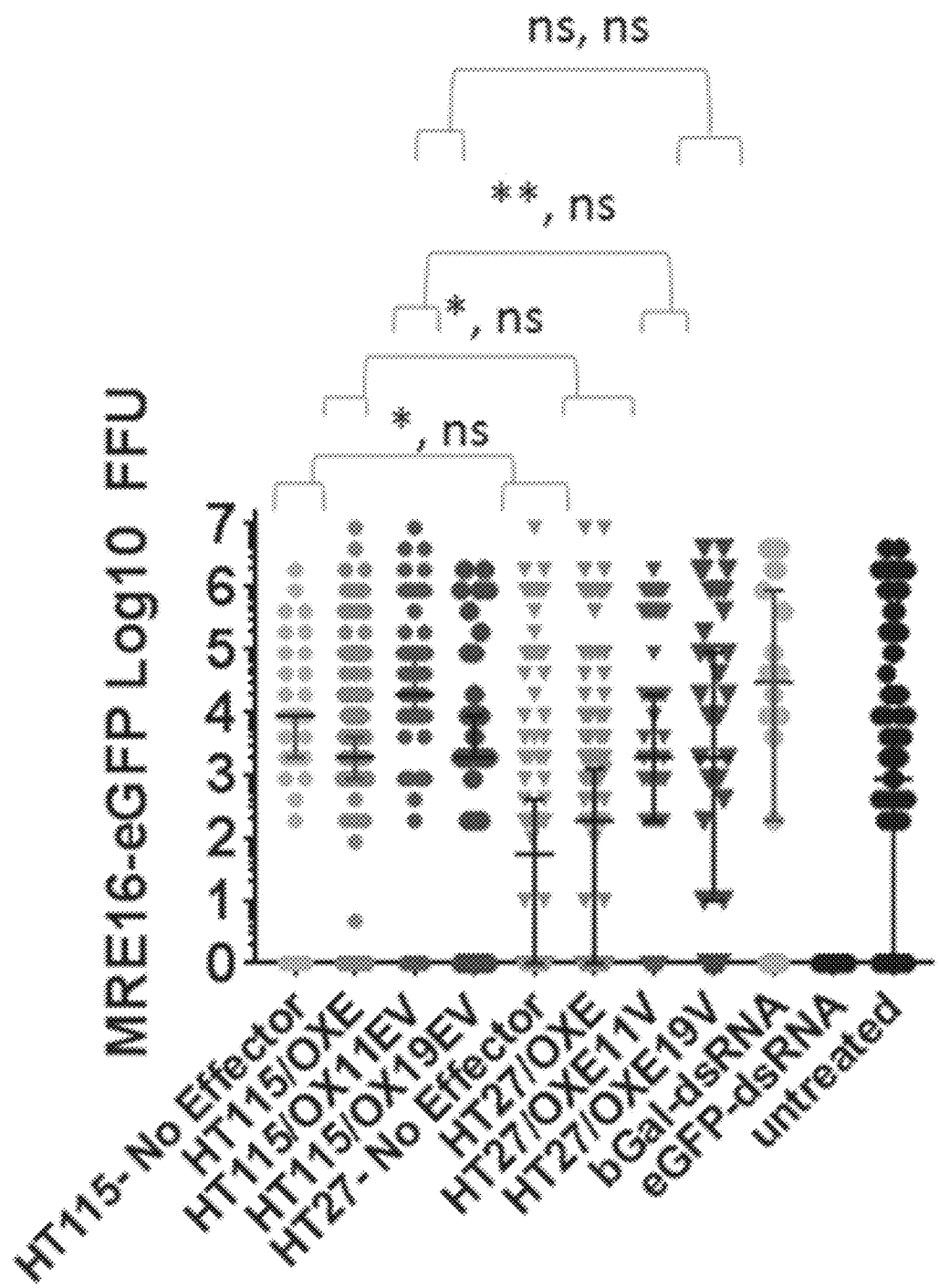

A comparison of the performance of the two strains from FIG. 20 reveals the following: Infection rates are lower in the HT27 strain with nanotubules compared to HT115 'no effector' background (Fisher's Exact test, p=0.016, Table 13). The addition of the 'E" effector bearing dsRNA.eGFP also reduced infection rates in the HT27 vs. HT115 background (Fisher's Exact test, p=0.04, Table 13).

TABLE 13

Titers, Infection Rates, and eGFP scoring of treated mosquitoes

| 4 dpi Strain | Geo Mean Log 10 titer FFU/mosq* | Infection Rates Infection/ Total (%) | GFP/Total (%) | Infection Rates Fisher's Exact test vs. Neg Control | Titers T-test (vs. Neg Control) | Infection Rates HT115 vs HT27 | Titers HT115 vs HT27 |
|---|---|---|---|---|---|---|---|
| HT115 negative | 4.09 | 35/47 (75) | 28/47 (60) | | | | |
| HT115, OX11-19E | 4.04 | 118/179 (65) | 89/179 (50) | ns | ns | | |
| HT115, OX11EV | 4.64 | 56/63 (89) | 52/63 (83) | ns | 0.008 increase | | |
| HT115, OX19EV | 4.05 | 32/42 (79) | 23/42 (55) | ns | ns | | |
| HT27, no effector | 4.47 | 45/86 (52) | 34/86 (40) | | | 0.016 | ns |
| HT27, OX11-19E | 4.11 | 63/118 (54) | 21/52 (40) | ns | ns | 0.0386 | ns |
| HT27, OX11EV | 4.47 | 38/57 (67) | 32/57 (56) | ns | ns | 0.0039 | ns |
| HT27, OX19EV | 4.46 | 26/37 (70) | 11/37 (30) | ns | ns | ns | ns |
| bGal dsRNA-injected | 5.07 | 15/20 (75) | | | | | |
| eGFP dsRNA-injected | na | 0/14 (0) | | | | | |
| untreated | 4.53 | 58/103 (56) | | | | | |

*Geometric mean of positive mosquitoes
FFU, focus-forming units

Figure 21:
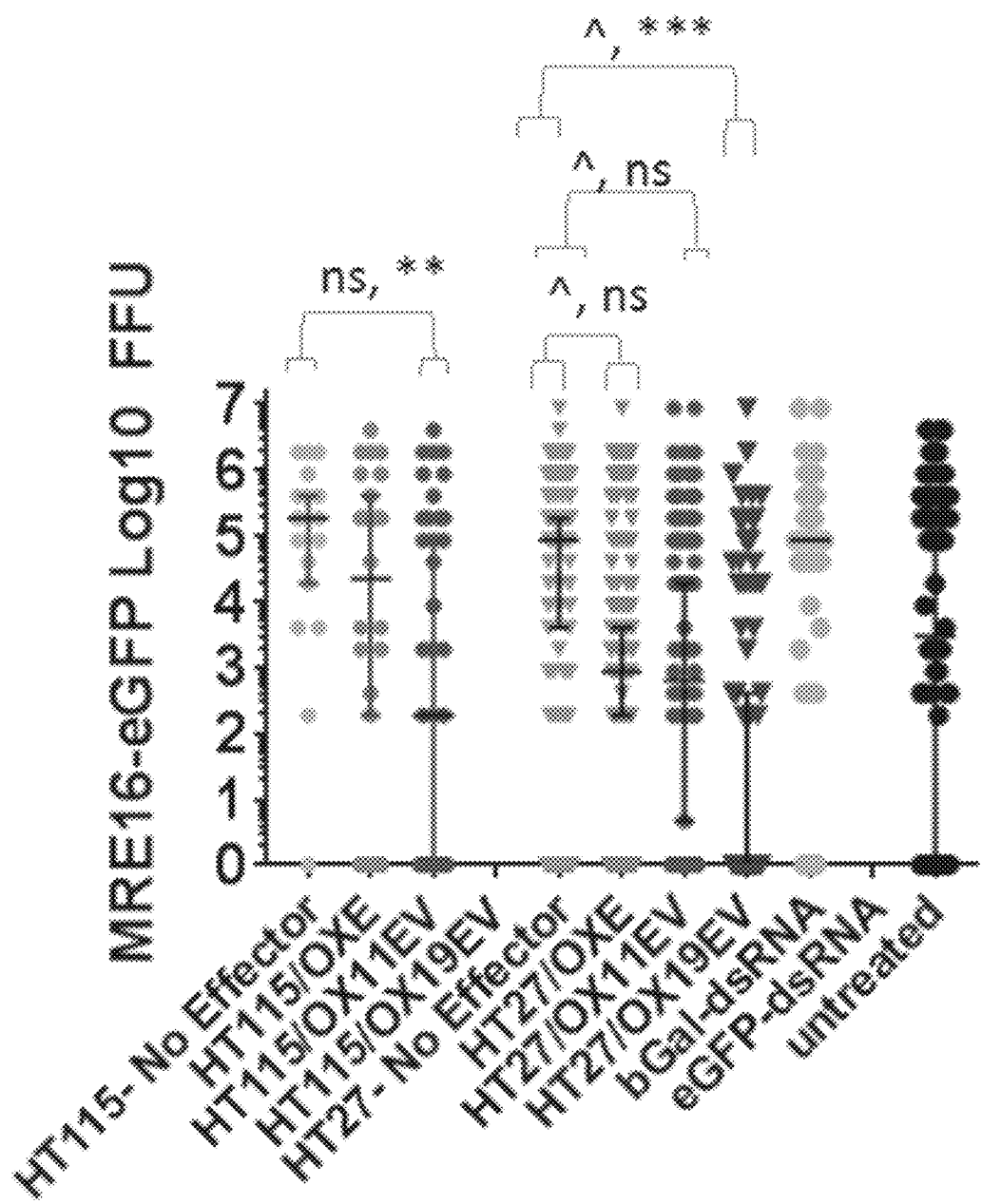

The present inventors continued the experiment and at 7 dpi mosquitoes infected with MRES16-eGFP and treated with bacteria carrying different plasmids were analyzed as above. As shown in FIG. 21, at 7 dpi HT115/OX11EV and HT27/OX19EV showed decreased infection rates compared to empty plasmid controls (Table 14, Fisher's Exact test shown below). HT27/OXE, HT27/OX11EV and HT27/OX19EV showed decreased viral titers compared to HT115 empty plasmid controls (Table 14, T-test of geometric means with Welch's correction). These data provide evidence that dsRNA against eGFP which is produced in Ht115 and HT27 has a statistically significant anti-viral effect. Furthermore, the present inventors demonstrated that VrrA has an enhancing effect of the dsRNA potency, such that it can be used as a helper gene.

TABLE 14

Titers, Infection Rates, and eGFP scoring of treated mosquitoes

| 7 dpi Strain | Geo Mean Log 10 titer FFU/mosq* | Infection Rates Infection/ Total (%) | GFP/Total (%) | Infection Rates Fisher's Exact test vs. Neg Control | Titers T-test (vs. Neg Control) | Infection Rates HT115 vs HT27 | Titers HT115 vs HT27 |
|---|---|---|---|---|---|---|---|
| HT115 negative | 5.02 | 15/16 (94)[++] | nd | | | | |
| HT115, OXE | 4.85 | 12/18 (67)[++] | 4.85 | nd | ns | ns | |
| HT115, OX11EV | 4.82 | 22/40 (55) | nd | 0.0055 | ns | | |
| HT115, OX19EV | no data | no data | no data | no data | no data | | |
| HT27, no effector | 4.99 | 68/94 (72) | 35/65 (52) | | | ns | ns |
| HT27, OXE | 4.45 | 62/99 (63) | 29/99 (29) | ns | 0.022 | ns | ns |
| HT27, OX11EV | 4.41 | 59/96 (61) | 40/96 (43) | ns | 0.015 | ns | ns |
| HT27, OX19EV | 4.50 | 34/78 (44) | 10/21 (48) | 0.0002 | 0.060 | nd | nd |
| bGal dsRNA-injected | 5.1 | 44/53 (83) | nd | | | | |

TABLE 14-continued

Titers, Infection Rates, and eGFP scoring of treated mosquitoes

| 7 dpi Strain | Geo Mean Log 10 titer FFU/mosq* | Infection Rates Infection/ Total (%) | GFP/Total (%) | Infection Rates Fisher's Exact test vs. Neg Control | Titers T-test (vs. Neg Control) | Infection Rates HT115 vs HT27 | Titers HT115 vs HT27 |
|---|---|---|---|---|---|---|---|
| eGFP dsRNA-injected untreated | ** 5.1 | ** 71/120 (59) | | | | | |

*Geometric mean of positive mosquitoes
FFU, focus-forming units
++low sample number; results are provisional
** Infected samples showed viral escape (ie., GFP−, CPE+).

Example 13: Internalization of Bacterial Expressed dsRNA in Mosquito Epithelial Cells The present inventors evaluated the internalization of bacterial expressed dsRNA against eGFP in mosquito epithelial cells. For this purpose, we used confocal fluorescence microscopy and samples from the HT27 strain/MRES16-eGFP mosquitoes at 4 dpi. Midguts were dissected and permealised using standard procedures. For localization of intracellular dsRNA, mouse anti-dsRNA antibody J2 from SCICONs was used and as secondary a goat anti-mouse conjugated with Alexa 555 dye. For the detection of eGFP, rabbit anti-eGFP was used and as a secondary a goat anti-rabbit conjugated with Alexa 647 dye. Nuclei of mosquito cells were stained with DAPI.

Figure 22:
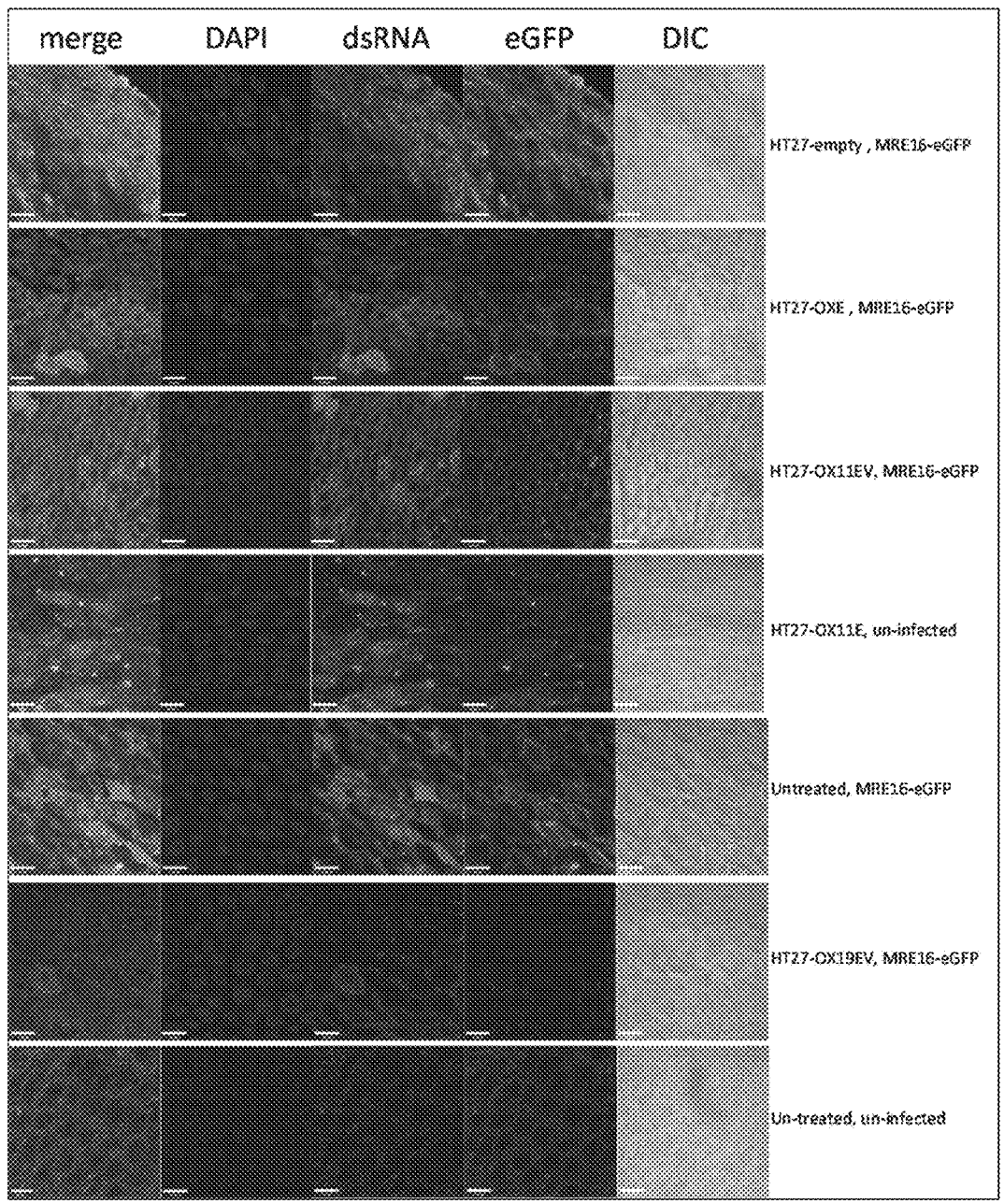
Figure 23:
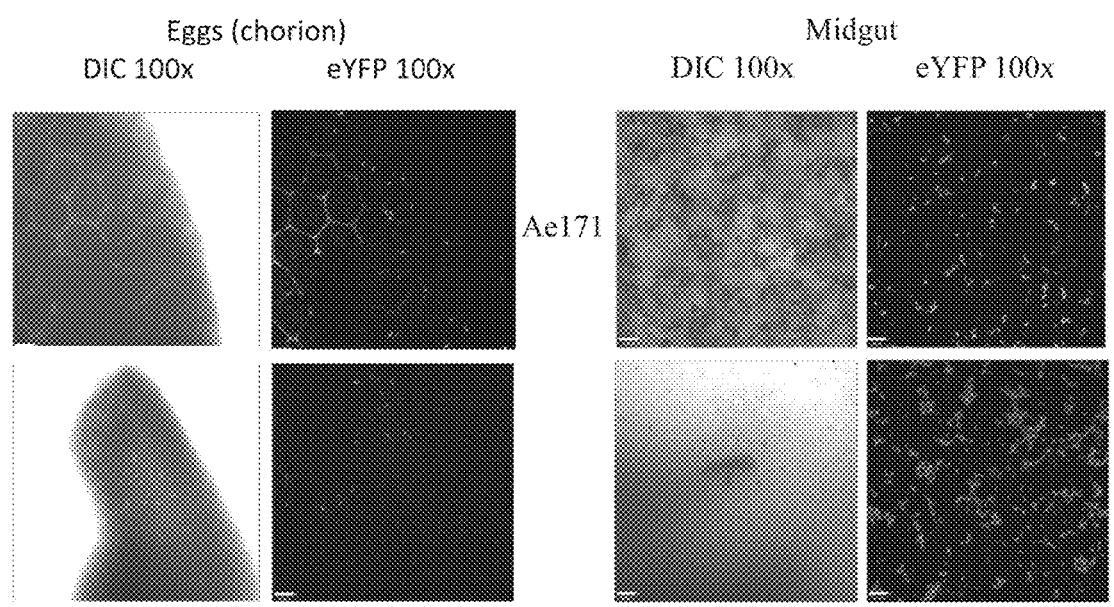

As demonstrated in FIG. 22, in mosquitoes infected with MRES16-eGFP and treated with HT27-OX19EV there is very little signal from the eGFP channel similar to the control (un-treated, un-infected) meaning there are very little MRES16-eGFP viruses, in contrast with mosquitoes infected with MRES16-eGFP but with no bacteria provided (untreated, MRES16-eGFP). In addition, signal from the dsRNA channel in mosquitoes treated with HT27-OX11E (HT27-OX11E, un-infected) is increased in comparison with the dsRNA signal from the control (un-treated, un-infected). As such, this demonstrates that bacterial derived dsRNA is found within mosquito cells.

Example 14: Identification of Endosymbionts that Persist Throughout the Life-Cycle of Mosquitoes The present inventors identified endosymbionts from *Ae. aegypti* mosquitoes and genotyped. In addition, a tagging method was developed that used yellow fluorescent protein (YFP) and the Tn7 transposon in order to monitor the targeted bacterial strains—any general type of which can be used for the purpose of tagging. As shown, some of the genotyped bacteria are truly endosymbionts and can be found in various tissues of the adult mosquito such as the midgut, ovaries, rectum and most importantly in laid eggs. FIG. S7 shows strains (Ae171, Ae142) belonging to the *Pseudomonas* genus that can populate the midgut of adult mosquitoes and also found in the chorion of eggs laid by female mosquitoes. These tagged with YFP strains were fed to larva and their presence was monitored in subsequent stages of the mosquito life cycle.

REFERENCES

The following references are hereby incorporated in their entirety by reference:

[1] Klausen M, Heydorn A, Ragas P, Lambertsen L, Aaes-Jorgensen A, Molin S, Tolker-Nielsen T. Biofilm formation by *Pseudomonas aeruginosa* wild type, flagella and type IV pili mutants. Molecular Microbiology, 2003; 48(6): 1511-24. PubMed PMID: 12791135.

[2] Puglise J M, Estep A S, Becnel J J (2015) Expression profiles and RNAi silencing of inhibitor apoptosis transcripts in *Aedes, Anopheles* and *Culex* mosquitoes (Diptera: Culicidae). *J. Med. Entomol.* 2015, 1-11.

[3] Zhang X, Mysore K, Flannery E, Michel K, Sevenson D W, Zhu K Y, Duman-Scheel M (2015) Chitosan interfering RNA nanoparticle mediated gene silencing in disease vector mosquito larvae. *J. Vis. Exp.* 97: 10.3791/52523.

[4] Rani, A, Sharma A, Rajagopal R, Adak T, and Bhatnagar R K (2009)Bacterial diversity analysis of larvae and adult midgut microflora using culture-dependent and culture-independent methods in lab-reared and field-collected *Anopheles stephensi*-an Asian malarial vector. *BMC Microbiol* 9: 96.

[5] Wang Y, Gilbreath T M, Kukutla P, Yan G, and Xu J. (2011) Dynamic gut microbiome across life history of the malaria mosquito *Anopheles gambiae* in Kenya. *PLoS One* 6(9): e24767

[6] Kumar A, Wang S, Ou R, Samrakandi M, Beerntsen B T and Sayre R T (2013) Development of an RNAi based microalgal larvicide to control mosquitoes. *Malaria World J.* 4 (6):1-7.

[7] Jose A M (2015) Movement of regulatory RNA between animal cells. Genesis 53: 395.

[8] Lindenbach B D, Rice C M. (2003) Molecular biology of flaviviruses. *Adv Virus Res.* 59: 23-61.

[9] Faye O, Caio C M, Iamaino A, Faye O, do Liveira J V, Diallo M, Zanotto P M, Sall A A. (2014) Molecular evolution of Zika virus during its emergence in the 20$^{th}$ century. *PLoS Negl Trop Dis.* http://dx.doi.org/10.1371/journal.pntd.0002636

[10] Crampton J, Beard C, and Louis C (2013) The Molecular Biology of Insect Disease Vectors: A Methods Manual. Chapman and Hall publishers.

[11] Pei D, Jiang J, Yu W, Kukutla P, Uentillie A, Xu J. (2015) The waaL gene mutation compromised the inhabitation of *Enterobacter* sp. Ag1 in the mosquito gut environment. *Parasit Vectors:* 8:437.

[12] Mukherjee, S., K. A. Hanley. 2010. RNA interference modulates dengue virus infection in *Drosophila melanogaster* cells. *BMC Microbiology* 10:127 PMCID: PMC2874549

[13] Hanley, K. A., J. T. Nelson, E. E. Schirtzinger, S. S. Whitehead, and C. T. Hanson. 2008. Superior infectivity for mosquito vectors contributes to competitive displacement among strains of dengue virus. *Biomed Central Ecology* 8:1.

[14] Hanley and C. C. Andrade. 2016. RNA interference: a pathway to arbovirus control. In Arboviruses. N. Vasilakis and D. Gubler (eds). Caister Academic Press. Hethersett, UK.

[15] Scott J G, Michel K, Bartholomay L C, Siegfried B D, Hunter W B, Smagghe G, Zhu K Y, Douglas A E (2013) Towards the elements of successful insect RNAi. J Insect Physiol. 2013 December; 59(12):1212-21. doi: 10.1016/j.jinsphys.2013.08.014. Epub 2013 Sep. 13.

[16] Jose A M (2015) Movement of regulatory RNA between animal cells. Genesis. 2015 July; 53(7):395-416. doi: 10.1002/dvg.22871. Epub 2015 Jul. 16.

[17] Hegde S, Rasgon J L, Hughes G L. The microbiome modulates arbovirus transmission in mosquitoes. Curr Opin Virol. 2015 December; 15:97-102. doi: 10.1016/j.coviro.2015.08.011. Epub 2015 Sep. 11.

[18] Foy B D, Myles K M, Pierro D J, Sanchez-Vargas I, Uhlirova M, Jindra M, et al. Development of a new Sindbis virus transducing system and its characterization in three Culicine mosquitoes and two Lepidopteran species. Insect Mol Biol. 2004; 13(1):89-100. PubMed PMID: 14728670.

[19] Ramakrishnan M A. Determination of 50% endpoint titer using a simple formula. World J Virol. 2016; 5(2): 85-6. doi: 10.5501/wjv.v5.i2.85. PubMed PMID: 27175354; PubMed Central PMCID: PMCPMC4861875.

[20] Ken E Olson and Carol D Blair, Arbovirus-mosquito Interactions: RNAi Pathway, Curr Opin Virol. 2015 December; 15: 119-126.

[21] Franz A W, Sanchez-Vargas I, Adelman Z N, Blair C D, Beaty B J, James A A, Olson K E. Engineering RNA interference-based resistance to dengue virus type 2 in genetically modified *Aedes aegypti*. Proc Natl Acad Sci USA. 2006; 103:4198-4203.

[22] Sánchez-Vargas I, Scott J C, Poole-Smith B K, Franz A W E, Barbosa-Solomieu V, Wilusz J, et al. (2009) Dengue Virus Type 2 Infections of *Aedes aegypti* Are Modulated by the Mosquito's RNA Interference Pathway. PLoS Pathog 5(2).

[23] TIMMONS, et al., Ingestion of bacterially expressed dsRNAs can produce specific and potent genetic interference in *Caenorhabditis elegans*, *Gene*, Jan. 24, 2001, pages 103-112, Volume 263, Issues 1-2.

[24] PANDE, et al., Metabolic cross-feeding via intercellular nanotubes among bacteria, *Nature Communications*, Feb. 23, 2015.

[25] TAKIFF, et al., Genetic analysis of the mrnc operon of *Escherichia coli.*, *Journal of Bacteriology*, May 1989, pages 2581-2590, Volume 171, Number 5.

[26] DEROUICHE, et al., Protein complex within *Escherichia coli* inner membrane. ToIA N-terminal domain interacts with TolQ and TolR proteins, *Journal of Biological Chemistry*, May 1, 1995.

[27] SONG, et al., A new *Vibrio cholera* sRNA modulates colonization and affects release of outer membrane vesicles, *Molecular Biology*, October 2008, pages 100-111, Volume 70, Issue 1.

[28] SHIH, et al., The SID-1 double-stranded RNA transporter is not selective for dsRNA length, *RNA*, Jan. 20, 2009, pages 384-390, RNA Society MCEWAN, et al., Uptake of Extracellular Double-Stranded RNA by SID-2, *Modular Cell*, Sep. 14, 2012, pages 746-754, Volume 47, Issue 5

[30] CAMPBELL, et al., Comparative genomics of small RNA regulatory pathway components in vector mosquitoes, BMC Genomics, Sep. 18, 2008, BioMed Central Ltd., accessed online at https://bmcgenomics.biomedcentral.com/articles/10.1186/1471-2164-9-425.

[31] KIM, et al., YmdB: a stress-responsive ribonuclease-biding regulator of *E. coli* RNase III activity, *Genes & Development*, 2008, pages 3497-3508, Volume 22.

[32] REN, et al., Staufen Negatively Modulates MicroRNA Activity in *Caenorhabditis elegans*, *G3: Genes, Genomes, Genetics*, May 1, 2016, pages 1227-1237, Volume 6, Number 5.

[33] RAMAN, et al., The double-stranded RNA binding protein RDE-4 can act cell autonomously during feeding RNAi in *C. elegans*, *Nucleic Acids Research*, Aug. 21, 2017, pages 8463-8473, Volume 45, Issue 14.

[34] ZHANG, et al., Functional replacement of the hemolysin A transport signal by a different primary sequence, *Cell Biology*, May 1993, pages 4211-4215, Volume 90, Proc. Natl. Acad. Sci. USA.

[35] NATALE, et al., Sec- and Tat-mediated protein secretion acress the bacterial cytoplasmic membrane-Distinct translocases and mechanisms, *Biochimica et Biophysica Acta (BBA)—Biomembranes*, September 2008, pages 1735-1756, Volume 1778, Issue 9.

[36] JONES, et al., Characterisation of cell-penetrating peptide-mediated peptide delivery, *British Journal of Pharmacology*, August 2005, pages 1093-1102, Volume 145, Issue 8.

[37] PROVOST, et al., Ribonuclease activity and RNA binding of recombinant human Dicer, *The EMBO Journal*, Nov. 1, 2002, pages 5587-5953, Volume 21, Issue 21.

[38] HAMMOND, et al., Argonaute2, a Link Between Genetic and Biochemical Analyses of RNAi, *Science*, Aug. 10, 2001, pages 1146-1150, Volume 293, Issue 5532.

[39] SCOTT, et al., Comparison of Dengue Virus Type 2-Specific Small RNAs from RNA Interference-Competent and -Incompetent Mosquito Cells, *PLOS Neglected Tropical Diseases*, Oct. 26, 2010.

[40] HESS, et al., Small RNA profiling of Dengue virus-mosquito interactions implicates the 5 PIWI RNA pathway in anti-viral defense, *BMC Microbiology*, Feb. 28, 2011.

[41] CAMPBELL, et al., *Aedes aegypti* uses RNA interference in defense against Sindbis virus infection, *BMC Microbiology*, Mar. 17, 2008.

[42] BETTENCOURT, et al., Hemolin gene silencing by ds-RNA injected into Cecropia pupae is lethal to next generation embryos, *Insect Molecular Biology*, May 8, 2002, pages 267-271, Volume 11, Issue 3.

[43] AMDAM, et al., Disruption of vitellogenin gene function in adult honeybees by intra-abdominal injection of double-stranded RNA, *BMC Biotechnology*, Jan. 20, 2003.

[44] TOMOYASU, et al., Larval RNAi in Tribolium (Coleoptera) for analyzing adult development, *Development Genes and Evolution*, November 2004, pages 575-578, Volume 214, Issue 11.

[45] SINGH, et al., Oral delivery of double-stranded RNA in larvae of the yellow fever mosquito, *Aedes aegypti*: Implications for pest mosquito control, *Journal of Insect Science*, Jan. 1, 2013, Volume 13, Issue 1.

[46] TURNER, et al., RNA interference in the light brown apple moth, *Epiphyas postvittana* (Walker) induced by double-stranded RNA feeding, *Insect Molecular Biology*, June 2006, pages 383-391, Volume 15, Issue 3.

[47] WANG, et al., Genome Mining Demonstrates the Widespread Occurrence of Gene Clusters Encoding Bacteriocins in Cyanobacteria, *PLOS One*, Jul. 20, 2011.

[48] KATOCH, et al., RNAi for Insect Control: Current Perspective and Future Challenges, *Applied Biochemistry and Biotechnology*, October 2013, pages 847-873, Volume 171, Issue 4.

[49] BONIZZONI, et al., Complex Modulation of the *Aedes aegypti* Transcriptome in Response to Dengue Virus Infection, *PLOS One*, Nov. 27, 2012.

[50] Wilke, Andre Barretto Bruno, and Mauro Toledo Marrelli. "Paratransgenesis: A Promising New Strategy for Mosquito Vector Control." Parasites & Vectors 8 (2015): 342. PMC. Web. 18 Sep. 2017.

[51] Beard C B, Mason P W, Aksoy S, Tesh R B, Richards F F. Transformation of an insect symbiont and expression of a foreign gene in the Chagas disease vector *Rhodnius prolixus*. Am J Trop Med Hyg. 1992; 46:195-200.

[52] Beard C B, O'Neill S L, Tesh R B, Richards F F, Aksoy S. Modification of arthropod vector competence via symbiotic bacteria. Parasitol Today. 1993; 9:179-183.

[53] Chavshin A R, Oshaghi M A, Vatandoost H, Pourmand M R, Raeisi A, Enayati A A, Mardani N, Ghoorchian S. Identification of bacterial microflora in the midgut of the larvae and adult of wild caught *Anopheles stephensi*: a step toward finding suitable paratransgenesis candidates. Acta Trop. 2012; 121:129-34.

[54] Conte J E., Jr A novel approach to preventing insect-borne diseases. N Engl J Med. 1997; 337:785-6.

[55] Beard C B, Cordon-Rosales C, Durvasula R V. Bacterial symbionts of the triatominae and their potential use in control of Chagas disease transmission. Annu Rev Entomol. 2002; 47:123-141.

[56] Favia G, Ricci I, Damiani C, Raddadi N, Crotti E, Marzorati M, Rizzi A, Urso R, Brusetti L, Borin S, Mora D, Scuppa P, Pasqualini L, Clementi E, Genchi M, Corona S, Negri I, Grandi G, Alma A, Kramer L, Esposito F, Bandi C, Sacchi L, Daffonchio D. Bacteria of the genus Asaia stably associate with *Anopheles stephensi*, an Asian malarial mosquito vector. Proc Natl Acad Sci USA. 2007; 104:9047-51.

[57] Yoshida S, Ioka D, Matsuoka H, Endo H, Ishii A. Bacteria expressing single-chain immunotoxin inhibit malaria parasite development in mosquitoes. Mol Biochem Parasitol. 2001; 113:89-96.

[58] Aksoy S, Weiss B, Attardo G. Paratransgenesis applied for control of tsetse transmitted sleeping sickness. Adv Exp Med Biol. 2008; 627:35-48.

[59] Coutinho-Abreu I V, Zhu K Y, Ramalho-Ortigao M. Transgenesis and paratransgenesis to control insect-borne diseases: current status and future challenges. Parasitol Int. 2009; 59:1-8.

[60] Pumpuni C B, Demaio J, Kent M, Davis J R, Beier J C. Bacterial population dynamics in three anopheline species: the impact on *Plasmodium* sporogonic development. Am J Trop Med Hyg. 1996; 54:214-8.

[61] Gonzalez-Ceron L, Santillan F, Rodriguez M H, Mendez D, Hernandez-Avila J E. Bacteria in midguts of field-collected *Anopheles albimanus* block *Plasmodium vivax* sporogonic development. J Med Entomol. 2003; 40:371-4.

[62] Lindh J M, Terenius O, Faye I. 16S rRNA gene-based identification of midgut bacteria from field-caught *Anopheles gambiae* sensu lato and *A. funestus* mosquitoes reveals new species related to known insect symbionts. Appl Environ Microbiol. 2005; 71:7217-23.

[63] Damiani C, Ricci I, Crotti E, Rossi P, Rizzi A, Scuppa P, Esposito F, Bandi C, Daffonchio D, Favia G. Paternal transmission of symbiotic bacteria in malaria vectors. Curr Biol. 2008; 18:1087-8.

[64] Terenius O, de Oliveira C D, Pinheiro W D, Tadei W P, James A A, Marinotti O. 16S rRNA gene sequences from bacteria associated with adult *Anopheles darlingi* (Diptera: Culicidae) mosquitoes. J Med Entomol. 2008; 45:172-5.

[65] Rani A, Sharma A, Rajagopal R, Adak T, Bhatnagar R K. Bacterial diversity analysis of larvae and adult midgut microflora using culture-dependent and culture-independent methods in lab-reared and field-collected *Anopheles stephensi*-an Asian malarial vector. BMC Microbiol. 2009; 19:9-96.

[66] Hillesland H, Read A, Subhadra B, Hurwitz I, McKelvey R, Ghosh K, Das P, Durvasula R. Identification of aerobic gut bacteria from the kala azar vector, *Phlebotomus argentipes*: a platform for potential paratransgenic manipulation of sand flies. Am J Trop Med Hyg. 2008; 79:881-6.

[67] Gaio A O, Gusmao D S, Santos A V, Berbert-Molina M A, Pimenta P F, Lemos F J. Contribution of midgut bacteria to blood digestion and egg production in *Aedes aegypti* (Diptera: culicidae) Parasit Vectors. 2011; 14:4-105.

[68] Sayler G S, Ripp S. Field applications of genetically engineered microorganisms for bioremediation processes. Curr Opin Biotechnol. 2000; 11:286-9.

[69] Briones A M, Shililu J, Githure J, Novak R, Raskin L. Thorsellia anophelisis the dominant bacterium in a Kenyan population of adult *Anopheles gambiae* mosquitoes. ISME J. 2008; 2:74-82.

[70] Wang S, Ghosh A K, Bongio N, Stebbings K A, Lampe D J, Jacobs-Lorena M. Fighting malaria with engineered symbiotic bacteria from vector mosquitoes. Proc Natl Acad Sci USA. 2012; 109:12734-9.

[71] Song, Tianyan et al. "A New *Vibrio Cholerae* sRNA Modulates Colonization and Affects Release of Outer Membrane Vesicles." *Molecular Microbiology* 70.1 (2008): 100-111. PMC. Web. 15 Mar. 2018.

Annika E. Sjöström, Linda Sandblad, Bernt Eric Uhlin & Sun Nyunt Wai. Membrane vesicle-mediated release of bacterial RNA. Nature Scientific Reports volume 5, Article number: 15329 (2015)

SEQUENCE LISTINGS

<130> 90115.00101

<150> 62/395,791
<151> 2016-09-16

<150> PCT/US17/52118
<151> 2017-09-18

<160> 7

<170> Patentin version 3.5

<210> 1
<211> 551
<212> DNA
<213> Zika Virus

<400> SEQ ID NO. 1
```
cccctagcg aagtactcac agctgttggc ctgatatgcg cattggctgg agggttcgcc    60
aaggcagata tagagatggc tgggcccatg gccgcgtcg gtctgctaat tgtcagttac   120
gtggtctcag gaaagagtgt ggacatgtac attgaaagag caggtgacat cacatgggaa   180
aaagatgcgg aagtcactgg aaacagtccc cggctcgatg tggcgctaga tgagagtggt   240
gatttctccc tggtgaggga tgacggtccc ccatgagag agatcatact caaggtggtc   300
ctgatgacca tctgtggcat gaacccaata gccatacct ttgcagctgg agcgtggtac   360
gtatacgtga agactggaaa aaggagtggt gctctatggg atgtgcctgc tcccaaggaa   420
gtaaaaaagg gggagaccac agatggagtg tacagagtaa tgactcgtag actgctaggt   480
tcaacacaag ttggagtggg agttatgcaa gaggggtct ttcacactat gtcctctgaa   540
ctaggtatga c                                                      551
```

<210> 2
<211> 507
<212> DNA
<213> Zika Virus

<400> SEQ ID NO. 2
```
gcggtgaagg gagacttgat ccatactggg gagatgtcaa gcaggatctg gtgtcatact    60
gtggtccatg gaagctagat gccgcctggg atgggcacac cgagcctgtcag ctcttggccg   120
tgccccccgg agagagagcg aggaacatcc agactctgcc cggaatatttt aagacaaagg   180
atggggacat tggagcggtt gcgctggatt acccagcagg aacttcagga tctccaatcc   240
tagacaagtg tgggagagtg ataggacttt atggcaatgg ggtcgtgatc aaaaacggga   300
gttatgttag tgccatcacc caagggagga gggaggaaga gactcctgtt gagtgcttcg   360
agccctcgat gctgaagaag aagcagctaa ctgtcttaga cttgcatcct ggagctggga   420
aaaccaggag agttcttcct gaaatagtcc gtgaagccat aaaaacaaga ctccgtactg   480
tgatcttagc tccaaccagg gttgtcg                                       507
```

<210> 3
<211> 550
<212> DNA
<213> Zika Virus

<400> SEQ ID NO. 3
```
ctgctgaaat ggaggaggcc cttagagggc ttccagtgcg ttatatgaca acagcagtca    60
atgtcaccca ctctggaaca gaaatcgtcg acttaatgtg ccatgccacc ttcacttcac   120
gtctactaca gccaatcaga gtccccaact ataatctgta tattatggat gaggcccact   180
tcacagatcc ctcaagtata gcagcaagag gatacatttc aacaagggtt gagatgggcg   240
aggcggctgc catcttcatg accgccacgc caccaggaac ccgtgacgca tttccggact   300
ccaactcacc aattatggac accgaagtgg aagtcccaga gagagcctgg agctcaggct   360
ttgattgggt gacggatcat tctgaaaaa cagtttggtt tgttccaagc gtgaggaacg   420
gcaatgagat cgcagcttgt ctgacaaagg ctggaaaacg ggtcatacag ctcagcagaa   480
agactttga cacagagttc cagaaaacaa aacatcaaga gtgggacttt gtcgtgacaa   540
ctgacatttc                                                         550
```

<210> 4
<211> 453
<212> DNA
<213> Zika Virus

<400> SEQ ID NO. 4
```
agagatgggc gccaacttta aagctgaccg tgtcatagat tccaggagat gcctaaagcc    60
ggtcatactt gatggcgaga gagtcattct ggctggaccc atgcctgtca cacatgccag   120
cgctgcccag aggagggggc gcataggcag gaatcccaac aaacctggag atgagtatct   180
gtatggaggt gggtgcgcag agactgacga agaccatgca cactggcttg aagcaagaat   240
gctccttgac aatatttacc tccaagatgg cctcatagcc tcgctctatc gacctgaggc   300
cgacaaagta gcagccattg agggagagtt caagcttagg acggagcaaa ggaagacctt   360
tgtggaactc atgaaaagag gagatcttcc tgtttggctg gcctatcagg ttgcatctgc   420
cggaataacc tacacagata gaagatggtg ctt                                453
```

<210> 5
<211> 538

SEQUENCE LISTINGS

<212> DNA
<213> Zika Virus

<400> SEQ ID NO. 5

```
cgaccaacaa caccataatg gaagacagtg tgccggcaga ggtgtggacc agacacggag    60
agaaaagagt gctcaaaccg aggtggatgg acgccagagt ttgttcagat catgcggccc   120
tgaagtcatt caaggagttt gccgctggga aaagaggagc ggcttttgga gtgatggaag   180
ccctgggaac actgccagga cacatgacag agagattcca ggaagccatt gacaacctcg   240
ctgtgctcat gcgggcagag actgaagca ggcttacaa agccgcggcg cccaattgc     300
cggagaccct agagaccata atgctttgg ggttgctggg aacagtctcg ctgggaatct   360
tcttcgtctt gatgaggaac aagggcatag ggaagatggg ctttggaatg gtgactcttg   420
gggccagcgc atggctcatg tggctctcgg aaattgagcc agccagaatt gcatgtgtcc   480
tcattgttgt gttcctattg ctggtggtgc tcatacctga gccagaaaag caaagatc     538
```

<210> 6
<211> 10675
<212> DNA
<213> Zika Virus

<400> SEQ ID NO. 6

```
gttgttgatc tgtgtgaatc agactgcgac agttcgagtt tgaagcgaaa gctagcaaca    60
gtatcaacag gttttatttt ggatttggaa acgagagttt ctggtcatga aaaacccaaa   120
aaagaaatcc ggaggattcc ggattgtcaa tatgctaaaa cgcggagtag cccgtgtgag   180
cccctttggg ggcttgaaga ggctgccagc cggacttctg ctgggtcatg ggcccatcag   240
gatggtcttg gcgattctag ccifittgag attcacggca atcaagccat cactgggtct   300
catcaataga tggggttcag tggggaaaaa agaggctatg gaaacaataa agaagttcaa   360
gaaagatctg gctgccatgc tgagaataat caatgctagg aaggagaaga agagacgagg   420
cgcagatact agtgtcggaa ttgttggcct cctgctgaca acagctatgg cagcggaggt   480
cactagacgt gggagtgcat actatatgta cttggacaga aacgatgctg gggaggccat   540
atcttttcca accacattgg ggatgaataa gtgttatata cagatcatgg atcttggaca   600
catgtgtgat gccaccatga gctatgaatg ccctatgctg gatgaggggg tggaaccaga   660
tgacgtcgat tgttggtgca acacgacgtc aacttgggtt gtgtacggac cctgccatca   720
caaaaaggt gaagcacgga gatctagaag agctgtgacg ctccctccc attccaccag   780
gaagctgcaa acgcggtcgc aaacctggtt ggaatcaaga gaatacacaa agcacttgat   840
tagagtcgaa aattggatat tcaggaaccc tggcttcgcg ttagcagcag ctgccatcgc   900
ttggcttttg ggaagctcaa cgagccataag agtcatatac ttggtcatga tactgctgat   960
tgcccgggca tacagcatca ggtgcatagg agtcagcaat agggactttg tggaaggtat  1020
gtcaggtggg acttgggttg atgttgtctt ggaacatgga ggttgtgtca ccgtaatggc  1080
acaggacaaa ccgactgtcg acatagagct ggttacaaca acagtcagca catggcgga   1140
ggtaagatcc tactgctatg aggcatcaat atcagacatg gcttctgaca gccgctgccc  1200
aacacaaggt gaagcctacc ttgacaagca atcagacact caatatgtct gcaaaagaac  1260
gttagtggac agaggctggg gaaatggatg tggacttttt ggcaaaggga gcctggtgac  1320
atgcgctaag tttgcatgct ccaagaaaat gaccgggaag agcatccagc cagagaatct  1380
ggagtaccgg ataatgctgt cagttcatgg ctcccagcac agtgggatga tcgttaatga  1440
cacaggacat gaaactgatg agaatagagc gaaagttgga ataacgccca ttcaccagg   1500
agccgaagcc accctggggg gttttgaag cctaggactt gattgtgaac cgaggacagg  1560
ccttgacttt tcagatttgt attacttgac tatgaataac aagcactggt tggttcacaa  1620
ggagtggttc cacgacattc cattaccttg gcacgctggg gcagacaccg gaactccaca  1680
ctggaacaac aaagaagcac tggtagagtt caaggacgca catgccaaaa ggcaaactgt  1740
cgtggttcta gggagtcaag aaggagcagt tcacacggcc cttgctgagg ctctggaggc  1800
tgagatggat ggtgcaaagg gaaggctgtc ctctggccac ttgaaatgtc gcctgaaaat  1860
ggataaactt agattgaagg gcgtgtcata ctccttgtgt actgcagcgt tcacattcac  1920
caagatcccg gctgaaacac tgcacggac agtcacagta gaggtacgat acgcagggac  1980
agatggacct tgcaaggttc agctcagat ggcggtggac atgcaaactc tgaccccagt  2040
tgggaggttg ataaccgcta ccccgtaat cactgaaagc actgagaact ctaagatgat  2100
gctgaacttg atccaccat ttgggactc ttacattgtc ataggagtcg gggagaagaa  2160
gatcaccac cactggcaca ggagtggcag caccattgga aaagcatttg aagccactgt  2220
gagaggtgcc aagagaatgg cagtcttggg agacacagca tgggactttg gatcagttgg  2280
aggcgctctc aactcattgg gcaagggcat ccatcaaatt tttggagcag ctttcaaatc  2340
attgtttgga ggaatgtcct ggttctcaca aattctcatt ggaacgttgc tgatgtggtt  2400
gggtctgaac acaagaatg atctatttc ccttatgtgc ttggcttag ggggagtgtt   2460
gatcttctta tccacagccg tctctgctga tgtgggtgc tccgtggcag catgggac    2520
ggagacgaga tgcggtacag gggtgttcgt ctataacgac gttgaagcct ggagggacag  2580
gtacaagtac catcctgact cccccgtag attggcagca gcagtcaagc aagcctggga  2640
agatggtatc tgcgggatct cctctgtttc aagaatggaa aacatcatgt ggagatcagt  2700
agaaggggag ctcaacgcaa tcctggaaga gaatggagtt caactgacgg tcgttgtggg  2760
atctgtaaaa aaccccatgt ggagaggtcc acagagattg cccgtgcctg tgaacgacgt  2820
gcccacggc tggaaggctt gggggaaatc gtatttcgtc agagcagcaa agacaaataa  2880
cagctttgtc gtgatggtg acactcgaa ggaatgccca ctcaaacata gagcatggaa  2940
cagctttctt gtggaggatc atgggttcgg ggtatttcac actagtgtct ggctcaaggt  3000
tagagaagat tattcattag agtgtgatcc agccgttatt ggaacagctg ttaagggaaa  3060
ggaggctgta cacagtgatc taggctactg gattgagagt gagaagaata cacatggaa   3120
gctgaagagg gccatctga tcagatgaa acatgtgaa tggccaaagt cccacacatt   3180
gtggacagat ggaatagaag agagtgatct gatcatacc aagtctttag ctgggccact  3240
cagccatcac aataccagag agggctacag gaccccaaatg aaagggccat ggcacagtga  3300
agagcttgaa attcggttt g aggaatgccc aggcactaag gtccacgtgg aggaaacatg  3360
tggaacaaga ggaccatctc tgagatcaac cactgcaagc ggaagggtga tcgaggaatg  3420
```

| | | | | |
|---|---|---|---|---|
| gtgctgcagg | gagtgcacaa | tgccccact | gtcgttccgg | gctaaagatg | gctgttggta | 3480 |
| tggaatggag | ataaggccca | ggaaagaacc | agaaagcaac | ttagtaaggt | caatggtgac | 3540 |
| tgcaggatca | actgatcaca | tggaccactt | ctcccttgga | gtgcttgtga | tcctgctcat | 3600 |
| ggtgcaggaa | gggctgaaga | agagaatgac | cacaaagatc | atcataagca | catcaatggc | 3660 |
| agtgctggta | gctatgatcc | tgggaggatt | ttcaatgagt | gacctggcta | agcttgcaat | 3720 |
| tttgatgggt | gccaccttcg | cggaaatgaa | cactggagga | gatgtagctc | atctggcgct | 3780 |
| gatagcggca | ttcaaagtca | gaccagcgtt | gctggtatct | ttcatcttca | gagctaattg | 3840 |
| gacaccccgt | gaaagcatgc | tgctgcctt | ggcctcgtgt | cttttgcaaa | ctgcgatctc | 3900 |
| cgccttggaa | ggcgacctga | tggttctcat | caatggtttt | gctttggcct | ggttggcaat | 3960 |
| acgagcgatg | gttgttccac | gcactgataa | catcaccttg | gcaatcctgg | ctgctctgac | 4020 |
| accactggcc | cggggcacac | tgcttgtggc | gtggagagca | ggccttgcta | cttgcggggg | 4080 |
| gtttatgctc | ctctctctga | agggaaaagg | cagtgtgaag | aagaacttac | catttgtcat | 4140 |
| ggccctggga | ctaaccgctg | tgaggctggt | cgaccccatc | aacgtggtgg | gactgctgtt | 4200 |
| gctcacaagg | agtgggaagc | ggagctggcc | ccctagcgaa | gtactcacag | ctgttggcct | 4260 |
| gatatgcgca | ttggctggag | ggttcgccaa | ggcagatata | gagatggctg | ggcccatggc | 4320 |
| cgcggtcggt | ctgctaattg | tcagttacgt | ggtctcagga | aagagtgtgg | acatgtacat | 4380 |
| tgaaagagca | ggtgacatca | catgggaaaa | agatgcggaa | gtcactggaa | acagtccccg | 4440 |
| gctcgatgtg | gcgctagatg | agagtggtga | tttctccctg | gtggaggatg | acggtccccc | 4500 |
| catgagagag | atcatactca | aggtggtcct | gatgaccatc | tgtggcatga | acccaatagc | 4560 |
| cataccctt | gcagctggag | cgtggtacgt | atacgtgaag | actggaaaaa | ggagtggtgc | 4620 |
| tctatgggat | gtgcctgctc | ccaaggaagt | aaaaaagggg | gagaccacag | atggagtgta | 4680 |
| cagagtaatg | actcgtagac | tgctaggttc | aacacaagtt | ggagtgggag | ttatgcaaga | 4740 |
| gggggtcttt | cacactatgt | ggcacgtcac | aaaaggatcc | gcgctgagaa | gcggtgaagg | 4800 |
| gagacttgat | ccatactggg | gagatgtcaa | gcaggatctg | gtgtcatact | gtggtccatg | 4860 |
| gaagctagat | gccgcctggg | atgggcacag | cgaggtgcag | ctcttggccg | tgcccccgg | 4920 |
| agagagagcg | aggaacatcc | agactctgcc | cggaatattt | aagacaaagg | atggggacat | 4980 |
| tggagcggtt | gcgctggatt | acccagcagg | aacttcagga | tctccaatcc | tagacaagtg | 5040 |
| tgggagagtg | ataggacttt | atggcaatgg | ggtcgtgatc | aaaaacggga | gttatgttag | 5100 |
| tgccatcacc | caaggagga | gggaggaaga | gactcctgtt | gagtgcttcg | agccctcgat | 5160 |
| gctgaagaag | aagcagctaa | ctgtcttaga | cttgcatcct | ggagctggga | aaaccaggag | 5220 |
| agttcttcct | gaaatagtcc | gtgaagccat | aaaaacaaga | ctccgtactg | tgatcttagc | 5280 |
| tccaaccagg | gttgtcgctg | ctgaaatgga | ggaggccct | agagggcttc | cagtgcgtta | 5340 |
| tatgacaaca | gcagtcaatg | tcacccactc | tggaacagaa | atcgtcgact | taatgtgcca | 5400 |
| tgccaccttc | acttcacgtc | tactacagcc | aatcagagtc | cccaactata | atctgtatat | 5460 |
| tatggatgag | gcccacttca | cagatccctc | aagtatagca | gcaagaggat | acatttcaac | 5520 |
| aagggttgag | atgggcgagg | cggctgccat | cttcatgacc | gccacgccac | caggaaccg | 5580 |
| tgacgcattt | ccggactcca | actcaccaat | tatggacacc | gaagtggaag | tcccagagag | 5640 |
| agcctgagc | tcaggctttg | attgggtgac | ggatcattct | ggaaaaacag | tttggtttgt | 5700 |
| tccaagcgtg | aggaacggca | atgagatcgc | agcttgtctg | acaaaggctg | gaaaacgggt | 5760 |
| catacagctc | agcagaaaga | cttttgagac | agagttccag | aaaacaaaac | atcaagagtg | 5820 |
| ggacttttgtc | gtgacaactg | acatttcaga | gatgggcgcc | aactttaaag | ctgaccgtgt | 5880 |
| catagattcc | aggagatgcc | taaagccggt | catacttgat | ggcgagagag | tcattctggc | 5940 |
| tggacccatg | cctgtcacac | atgccagcgc | tgcccagagg | aggggggcgca | taggcaggaa | 6000 |
| tcccaacaaa | cctggagatg | agtatctgta | tggaggtggg | tgcgcagaga | ctgacgaaga | 6060 |
| ccatgcacac | tggcttgaag | caagaatgct | ccttgacaat | atttacctcc | aagatggcct | 6120 |
| catagcctcg | ctctatcgac | ctgaggccga | caaagtagca | gccattgagg | gagagttcaa | 6180 |
| gcttaggacg | gagcaaagga | agacctttgt | ggaactcatg | aaaagaggag | atcttcctgt | 6240 |
| ttggctggcc | tatcaggttg | catctgccgg | aataacctac | acagatagaa | gatggtgctt | 6300 |
| tgatgcacg | accaacaaca | ccataatgga | agacagtgtg | ccggcacagg | tgtggaccag | 6360 |
| acacggagag | aaaagagtgc | tcaaaccgag | gtgatggac | gccagagttt | gttcagatca | 6420 |
| tgcggccctg | aagtcattca | aggagtttgc | cgctgggaaa | agaggagcgg | cttttggagt | 6480 |
| gatggaagcc | ctgggaacac | tgccaggaca | catgacagag | agattccagg | aagccattga | 6540 |
| caacctcgct | gtgctcatgc | gggcagagac | tggaagcagg | ccttacaaag | ccgcggcggc | 6600 |
| ccaattgccg | gagaccctag | agaccataat | gctttttggg | ttgctgggaa | cagtctcgct | 6660 |
| gggaatcttc | ttcgtcttga | tgaggaacaa | gggcataggg | aagatgggct | ttggaatggt | 6720 |
| gactcttggg | gccagcgcat | ggctcatgtg | gctctcggaa | attgagccag | ccagaattgc | 6780 |
| atgtgtcctc | attgttgtgt | tcctattgct | ggtggtgctc | atacctgagc | cagaaaagca | 6840 |
| aagatctccc | caggacaacc | aaatggcaat | catcatcatg | gtagcagtag | gtcttctggg | 6900 |
| cttgattacc | gccaatgaac | tcggatggtt | ggagagaaca | aagagtgacc | taagccatct | 6960 |
| aatgggaagg | agagaggagg | gggcaaccat | aggattctca | atggacattg | acctgcggcc | 7020 |
| agcctcagct | tgggccatct | atgctgcctt | gacaactttc | attaccccag | ccgtccaaca | 7080 |
| tgcagtgacc | acctcataca | acaactactc | cttaatggcg | atggccacgc | aagctggagt | 7140 |
| gttgtttggc | atgggcaaag | ggatgccatt | ctacgcatgg | gactttggag | tcccgctgct | 7200 |
| aatgataggt | tgctactcac | aattaacacc | cctgaccta | atagtggcca | tcatttgct | 7260 |
| cgtggcgcac | tacatgtact | tgatcccagg | gctgcaggca | gcagctgcgc | gtgctgccca | 7320 |
| gaagagaacg | gcagctggca | tcatgaagaa | ccctgttgtg | gatggaatag | tggtgactga | 7380 |
| cattgacaca | atgacaattg | acccccaagt | ggagaaaaag | atgggacagg | tgctactcat | 7440 |
| agcagtagcc | gtctccagcg | ccatactgtc | gcgaccgcc | tggggtggg | ggaggctgg | 7500 |
| ggctctgatc | acagccgcaa | cttccactt | gtgggaagc | tctccgaaca | agtactggaa | 7560 |
| ctcctctaca | gccacttcac | tgtgtaacat | ttttaggga | agttacttgg | ctggagcttc | 7620 |
| tctaatctac | acagtaacaa | gaaacgctgg | cttggtcaag | agacgtgggg | gtggaacagg | 7680 |
| agagaccctg | ggagagaaat | ggaaggcccg | cttgaaccag | atgtcggccc | tggagttcta | 7740 |
| ctcctacaaa | aagtcaggca | tcaccgaggt | gtgcagaaa | gaggcccgcc | gcgccctcaa | 7800 |
| ggacggtgtg | gcaacgggag | gccatgctgt | gtcccgagga | agtgcaaagc | tgagatggtt | 7860 |
| ggtgagcgg | ggatacctgc | agccctatgg | aaaggtcatt | gatcttggat | gtggcagagg | 7920 |
| gggctggagt | tactacgtcg | ccaccatccg | caaagttcaa | gaagtgaaag | gatacacaaa | 7980 |
| aggaggccct | ggtcatgaag | aacccgtgtt | ggtgcaaagc | tatgggtgga | acatagtccg | 8040 |

```
tcttaagagt ggggtggacg tctttcatat ggcggctgag ccgtgtgaca cgttgctgtg   8100
tgacataggt gagtcatcat ctagtcctga agtggaagaa gcacggacgc tcagagtcct   8160
ctccatggtg ggggattggc ttgaaaaaag accaggagcc ttttgtataa aagtgttgtg   8220
cccatacacc agcactatga tggaaaccct ggagcgactg cagcgtaggt atggggagg    8280
actggtcaga gtgccactct cccgcaactc tacacatgag atgtactggg tctctggagc   8340
gaaaagcaac accataaaaa gtgtgtccac cacgagccag ctectcttgg ggcgcatgga   8400
cgggcctagg aggccagtga aatatgagga ggatgtgaat ctcggctctg gcacgcgggc   8460
tgtggtaagc tgcgctgaag ctcccaacat gaagatcatt ggtaaccgca ttgaaaggat   8520
ccgcagtgag cacgcggaaa cgtggttctt tgacgagaac cacccatata ggacatgggc   8580
ttaccatgga agctatgagg ccccacaca agggtcagcg tcctctctaa taaacggggt     8640
tgtcaggctc ctgtcaaaac cctgggatgt ggtgactgga gtcacaggaa tagccatgac   8700
cgacaccaca ccgtatggtc agcaaagagt tttcaaggaa aaagtggaca ctagggtgcc   8760
agaccccaa gaaggcactc gtcaggttat gagcatggtc tcttcctggt tgtggaaaga     8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacgaa gaaagagagc accacctgag   9000
aggagagtgc cagagctgtg tgtacaacat gatggggaaa agagaaaaga aacaagggga   9060
atttggaaag gccaagggca gccgcgccat ctggtatatg tggctagggg ctagatttct   9120
agagttcgaa gcccttggat tcttgaacga ggatcactgg atggggagag agaactcagg   9180
aggtgtgtt gaagggctgg gattacaaag actcggatat gtcctagaag agatgagtcg     9240
tataccagga ggaaggatgt atgcagatga cactgctggc tgggacaccc gcattagcag   9300
gtttgatctg gagaatgaag ctcaatcac caaccaaatg gagaaagggc acgggcctt     9360
ggcattggcc ataatcaagt acacatacca aaacaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtggctg ctgcggaggt cagagaaagt   9600
gaccaactgt ttgcagagca acggatggga taggctcaaa cgaatggcag tcagtggaga   9660
tgattcgtt gtgaagccaa ttgatgatag gtttgcacat gccctcaggt tcttgaatga    9720
tatgggaaaa gttaggaagg acacacaaga gtgaaaccc tcaactggat gggacaactg    9780
ggaagaagtt ccgttttgct cccaccactt caacaagctc catctcaagg acgggaggtc   9840
cattgtggtt ccctgccgcc accaagatga actgattggc cgggcccgcg tctctccagg   9900
ggcgggatgg agcatccggg agactgcttg cctagcaaaa tcatatgcgc aaatgtggca   9960
gctcctttat ttccacagaa gggacctccg actgatggcc aatgccattt gttcatctgt   10020
gccagttgac tgggttccaa ctgggagaac tacctggtca atccatgaa agggagaatg    10080
gatgaccact gaagacatgc ttgtggtgtg aacagagtg tggattgagg agaacgacca     10140
catggaagac aagaccccag ttcgaaatg gacagacatt ccctatttgg gaaaaaggga    10200
agacttgtgg tgtggatctc tcatagggca cagaccgcgc accacctggg ctgagaacat   10260
taaaaacaca gtcaacatgg tgcgcaggat cataggtgat gaagaaaagt acatggacta   10320
cctatccacc caagttcgct acttgggtga agaagggtct acacctggag tgctgtaagc   10380
accaatctta atgttgtcag gcctgctagt cagccacagc ttggggaaag ctgtgcagcc   10440
tgtgaccccc ccaggagaag ctgggaaacc aagcctatag tcaggccgga aacgccatg    10500
cacggaagaa gccatgctgc ctgtgagccc ctcagaggac actgagtcaa aaaccccac    10560
gcgcttggag gcgcaggatg ggaaaagaag gtggcgacct tccccaccct tcaatctggg   10620
gcctgaactg gagatcagct gtggatctcc agaagaggga ctagtggtta gagga        10675
```

<210> 7
<211> 149
<212> DNA
<213> *Vibrio cholera*

<400> SEQ ID NO. 7
```
gtgattgaca gagctttgag agtttactg gccgtcaaat ttggttctcg acccgctgtc     60
accaattacg ctgctttttc ctttttatta actcctatac ttgtgtacgc ccaaagccag   120
attgttttgg gcgttttttt atctggttt                                     149
```

---

SEQUENCE LISTING

<160> NUMBER OF SEQ ID NOS: 7

<210> SEQ ID NO 1
<211> LENGTH: 551
<212> TYPE: DNA
<213> ORGANISM: Zika Virus

<400> SEQUENCE: 1

```
cccctagcg aagtactcac agctgttggc ctgatatgcg cattggctgg agggttcgcc     60
aaggcagata tagagatggc tgggcccatg gccgcggtcg gtctgctaat tgtcagttac   120
gtggtctcag gaaagagtgt ggacatgtac attgaaagag caggtgacat cacatgggaa   180
aaagatgcgg aagtcactgg aaacagtccc cggctcgatg tggcgctaga tgagagtggt   240
```

```
gatttctccc tggtggagga tgacggtccc cccatgagag agatcatact caaggtggtc    300
ctgatgacca tctgtggcat gaacccaata gccatacccc ttgcagctgg agcgtggtac    360
gtatacgtga agactggaaa aaggagtggt gctctatggg atgtgcctgc tcccaaggaa    420
gtaaaaaagg gggagaccac agatggagtg tacagagtaa tgactcgtag actgctaggt    480
tcaacacaag ttggagtggg agttatgcaa gaggggtctt tcacactat gtcctctgaa     540 ctaggtatga c                                                        551

<210> SEQ ID NO 2
<211> LENGTH: 507
<212> TYPE: DNA
<213> ORGANISM: Zika Virus

<400> SEQUENCE: 2
gcggtgaagg gagacttgat ccatactggg gagatgtcaa gcaggatctg gtgtcatact     60
gtggtccatg gaagctagat gccgcctggg atgggcacag cgaggtgcag ctcttggccg    120
tgcccccggg agagagagcg aggaacatcc agactctgcc cggaatattt aagacaaagg    180
atggggacat ggagcggtt gcgctggatt acccagcagg aacttcagga tctccaatcc     240
tagacaagtg tgggagagtg ataggactt atggcaatgg ggtcgtgatc aaaaacggga    300
gttatgttag tgccatcacc caagggagga gggaggaaga actcctgtt gagtgcttcg    360 agccctcgat gctgaagaag aagcagctaa ctgtcttaga cttgcatcct ggagctggga    420
aaaccaggag agttcttcct gaaatagtcc gtgaagccat aaaaacaaga ctccgtactg    480
tgatcttagc tccaaccagg gttgtcg                                       507

<210> SEQ ID NO 3
<211> LENGTH: 550
<212> TYPE: DNA
<213> ORGANISM: Zika Virus

<400> SEQUENCE: 3
ctgctgaaat ggaggaggcc cttagagggc ttccagtgcg ttatatgaca acagcagtca     60
atgtcaccca ctctggaaca gaaatcgtcg acttaatgtg ccatgccacc ttcacttcac    120
gtctactaca gccaatcaga gtccccaact ataatctgta tattatggat gaggcccact    180
tcacagatcc ctcaagtata gcagcaagag gatacatttc aacaagggtt gagatggcg     240 aggcggctgc catcttcatg accgccacgc caccaggaac ccgtgacgca tttccggact    300
ccaactcacc aattatggac accgaagtgg aagtcccaga gagagcctgg agctcaggct    360
ttgattgggt gacggatcat tctggaaaaa cagtttggtt tgttccaagc gtgaggaacg    420
gcaatgagat cgcagcttgt ctgacaaagg ctggaaaacg gtcatacag ctcagcagaa     480 agacttttga cagagttc cagaaaacaa acatcaaga gtgggacttt gtcgtgacaa      540
ctgacatttc                                                          550

<210> SEQ ID NO 4
<211> LENGTH: 453
<212> TYPE: DNA
<213> ORGANISM: Zika Virus

<400> SEQUENCE: 4
agagatgggc gccaacttta aagctgaccg tgtcatagat tccaggagat gcctaaagcc     60
ggtcatactt gatggcgaga gagtcattct ggctggaccc atgcctgtca cacatgccag    120
```

| | |
|---|---|
| cgctgcccag aggaggggc gcataggcag gaatcccaac aaacctggag atgagtatct | 180 |
| gtatggaggt gggtgcgcag agactgacga agaccatgca cactggcttg aagcaagaat | 240 |
| gctccttgac aatatttacc tccaagatgg cctcatagcc tcgctctatc gacctgaggc | 300 |
| cgacaaagta gcagccattg agggagagtt caagcttagg acggagcaaa ggaagacctt | 360 |
| tgtggaactc atgaaaagag gagatcttcc tgtttggctg gcctatcagg ttgcatctgc | 420 |
| cggaataacc tacacagata gaagatggtg ctt | 453 |

<210> SEQ ID NO 5
<211> LENGTH: 538
<212> TYPE: DNA
<213> ORGANISM: Zika Virus

<400> SEQUENCE: 5

| | |
|---|---|
| cgaccaacaa caccataatg aagacagtg tgccggcaga ggtgtggacc agacacggag | 60 |
| agaaaagagt gctcaaaccg aggtggatgg acgccagagt ttgttcagat catgcggccc | 120 |
| tgaagtcatt caaggagttt gccgctggga aagaggagc ggcttttgga gtgatggaag | 180 |
| ccctgggaac actgccagga cacatgacag agagattcca ggaagccatt gacaacctcg | 240 |
| ctgtgctcat gcgggcagag actggaagca ggccttacaa agccgcggcg gcccaattgc | 300 |
| cggagaccct agagaccata atgcttttgg ggttgctggg aacagtctcg ctgggaatct | 360 |
| tcttcgtctt gatgaggaac aagggcatag gaagatgggg ctttggaatg gtgactcttg | 420 |
| gggccagcgc atggctcatg tggctctcgg aaattgagcc agccagaatt gcatgtgtcc | 480 |
| tcattgttgt gttcctattg ctggtggtgc tcataccctga gccagaaaag caaagatc | 538 |

<210> SEQ ID NO 6
<211> LENGTH: 10675
<212> TYPE: DNA
<213> ORGANISM: Zika Virus

<400> SEQUENCE: 6

| | |
|---|---|
| gttgttgatc tgtgtgaatc agactgcgac agttcgagtt tgaagcgaaa gctagcaaca | 60 |
| gtatcaacag gttttatttt ggatttggaa acgagagttt ctggtcatga aaaacccaaa | 120 |
| aaagaaatcc ggaggattcc ggattgtcaa tatgctaaaa cgcggagtag cccgtgtgag | 180 |
| cccctttggg ggcttgaaga ggctgccagc cggacttctg ctgggtcatg ggcccatcag | 240 |
| gatggtcttg gcgattctag cctttttgag attcacggca atcaagccat cactgggtct | 300 |
| catcaataga tggggttcag tggggaaaaa agaggctatg gaaacaataa agaagttcaa | 360 |
| gaaagatctg gctgccatgc tgagaataat caatgctagg aaggagaaga gagacgagg | 420 |
| cgcagatact agtgtcggaa ttgttggcct cctgctgacc acagctatgg cagcggaggt | 480 |
| cactagacgt gggagtgcat actatatgta cttggacaga aacgatgctg gggaggccat | 540 |
| atcttttcca accacattgg ggatgaataa gtgttatata cagatcatgg atcttggaca | 600 |
| catgtgtgat gccaccatga gctatgaatg ccctatgctg gatgaggggg tggaaccaga | 660 |
| tgacgtcgat tgttggtgca acacgacgtc aacttgggtt gtgtacggaa cctgccatca | 720 |
| caaaaaggt gaagcacgga gatctagaag agctgtgacg ctcccctccc attccaccag | 780 |
| gaagctgcaa acgcggtcgc aaacctggtt ggaatcaaga gaatacacaa agcacttgat | 840 |
| tagagtcgaa aattggatat tcaggaaccc tggcttcgcg ttagcagcag ctgccatcgc | 900 |
| ttggctttg ggaagctcaa cgagccaaaa agtcatatac ttggtcatga tactgctgat | 960 |
| tgccccggca tacagcatca ggtgcatagg agtcagcaat agggactttg tggaaggtat | 1020 |

```
gtcaggtggg acttgggttg atgttgtctt ggaacatgga ggttgtgtca ccgtaatggc    1080
acaggacaaa ccgactgtcg acatagagct ggttacaaca acagtcagca acatggcgga    1140
ggtaagatcc tactgctatg aggcatcaat atcagacatg gcttctgaca gccgctgccc    1200
aacacaaggt gaagcctacc ttgacaagca atcagacact caatatgtct gcaaaagaac    1260
gttagtggac agaggctggg gaaatggatg tggactttt ggcaagggga gcctggtgac     1320
atgcgctaag tttgcatgct ccaagaaaat gaccgggaag agcatccagc cagagaatct    1380
ggagtaccgg ataatgctgt cagttcatgg ctcccagcac agtgggatga tcgttaatga    1440
cacaggacat gaaactgatg agaatagagc gaaagttgag ataacgccca attcaccgag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgacattc cattaccttg gcacgctggg gcagacaccg gaactccaca    1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgaccccagt    2040
tgggaggttg ataaccgcta accccgtaat cactgaaagc actgagaact ctaagatgat    2100
gctggaactt gatccaccat ttgggactc ttacattgtc ataggagtcg gggagaagaa     2160
gatcacccac cactggcaca ggagtggcag caccattgga aaagcatttg aagccactgt    2220
gagaggtgcc aagagaatgg cagtcttggg agacacagcc tgggactttg gatcagttgg    2280
aggcgctctc aactcattgg gcaagggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggccttag gggagtgtt    2460 gatcttctta tccacagccg tctctgctga tgtggggtgc tcggtggact ctcaaagaa     2520 ggagacgaga tgcggtacag gggtgttcgt ctataacgac gttgaagcct ggagggacag    2580
gtacaagtac catcctgact ccccccgtag attggcagca gcagtcaagc aagcctggga    2640
agatggtatc tgcgggatct cctctgtttc aagaatggaa acatcatgt ggagatcagt     2700 agaaggggag ctcaacgcaa tcctggaaga gaatggagtt caactgacgg tcgttgtggg    2760
atctgtaaaa aaccccatgt ggagaggtcc acagagattg cccgtgcctg tgaacgagct    2820
gccccacggc tggaaggctt ggggggaaatc gtatttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa acatgtgaa tggccaaagt cccacacatt      3180
gtggacagat ggaatagaag agagtgatct gatcataccc aagtctttag ctgggccact    3240
cagccatcac aataccagag agggctacag gacccaaatg aaagggccat ggcacagtga    3300
agagcttgaa attcggtttg aggaatgccc aggcactaag gtccacgtgg aggaaacatg    3360
```

```
tggaacaaga ggaccatctc tgagatcaac cactgcaagc ggaagggtga tcgaggaatg      3420
gtgctgcagg gagtgcacaa tgcccccact gtcgttccgg gctaaagatg gctgttggta      3480
tggaatggag ataaggccca ggaaagaacc agaaagcaac ttagtaaggt caatggtgac      3540
tgcaggatca actgatcaca tggaccactt ctcccttgga gtgcttgtga tcctgctcat      3600
ggtgcaggaa gggctgaaga agagaatgac cacaaagatc atcataagca catcaatggc      3660
agtgctggta gctatgatcc tgggaggatt ttcaatgagt gacctggcta agcttgcaat      3720
tttgatgggt gccaccttcg cggaaatgaa cactggagga gatgtagctc atctggcgct      3780
gatagcggca ttcaaagtca gaccagcgtt gctggtatct ttcatcttca gagctaattg      3840
gacaccccgt gaaagcatgc tgctggcctt ggcctcgtgt cttttgcaaa ctgcgatctc      3900
cgccttggaa ggcgacctga tggttctcat caatggtttt gctttggcct ggttggcaat      3960
acgagcgatg gttgttccac gcactgataa catcaccttg gcaatcctgg ctgctctgac      4020
accactggcc cggggcacac tgcttgtggc gtggagagca ggccttgcta cttgcggggg      4080
gtttatgctc ctctctctga agggaaaagg cagtgtgaag aagaacttac catttgtcat      4140
ggccctggga ctaaccgctg tgaggctggt cgaccccatc aacgtggtgg gactgctgtt      4200
gctcacaagg agtgggaagc ggagctggcc ccctagcgaa gtactcacag ctgttggcct      4260
gatatgcgca ttggctggag ggttcgccaa ggcagatata gagatggctg ggcccatggc      4320
cgcggtcggt ctgctaattg tcagttacgt ggtctcagga aagagtgtgg acatgtacat      4380
tgaaagagca ggtgacatca catgggaaaa agatgcggaa gtcactggaa acagtccccg      4440
gctcgatgtg cgctagatg agagtggtga tttctccctg gtggaggatg acggtccccc      4500
catgagagag atcatactca aggtggtcct gatgaccatc tgtggcatga acccaatagc      4560
catacccttt gcagctggag cgtggtacgt atacgtgaag actggaaaaa ggagtggtgc      4620
tctatgggat gtgcctgctc ccaaggaagt aaaaaagggg gagaccacag atggagtgta      4680
cagagtaatg actcgtagac tgctaggttc aacacaagtt ggagtgggag ttatgcaaga      4740
gggggtcttt cacactatgt ggcacgtcac aaaaggatcc gcgctgagaa gcggtgaagg      4800
gagacttgat ccatactggg gagatgtcaa gcaggatctg gtgtcatact gtggtccatg      4860
gaagctagat gccgcctggg atgggcacag cgaggtgcag ctcttggccg tgccccccgg      4920
agagagagcg aggaacatcc agactctgcc cggaatattt aagacaaagg atggggacat      4980
tggagcggtt gcgctggatt acccagcagg aacttcagga tctccaatcc tagacaagtg      5040
tgggagagtg ataggacttt atggcaatgg ggtcgtgatc aaaaacggga gttatgttag      5100
tgccatcacc caagggagga gggaggaaga gactcctgtt gagtgcttcg agccctcgat      5160
gctgaagaag aagcagctaa ctgtcttaga cttgcatcct ggagctggga aaaccaggag      5220
agttcttcct gaaatagtcc gtgaagccat aaaaacaaga ctccgtactg tgatcttagc      5280
tccaaccagg gttgtcgctg ctgaaatgga ggagccctt agagggcttc cagtgcgtta      5340
tatgacaaca gcagtcaatg tcacccactc tggaacagaa atcgtcgact taatgtgcca      5400
tgccaccttc acttcacgtc tactacagcc aatcagagtc cccaactata atctgtatat      5460
tatggatgag gccacttca cagatccctc aagtatagca gcaagaggat acatttcaac      5520
aagggttgag atgggcgagg cggctgccat cttcatgacc gccacgccac caggaacccg      5580
tgacgcattt ccggactcca actcaccaat tatggacacc gaagtggaag tcccagagag      5640
agcctggagc tcaggctttg attgggtgac ggatcattct ggaaaaacag tttggttgt      5700 tccaagcgtg aggaacggca atgagatcgc agcttgtctg acaaaggctg gaaaacgggt      5760
```

```
catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgcccagagg aggggcgca taggcaggaa     6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga agacctttgt ggaactcatg aaaagaggag atcttcctgt    6240
ttggctggcc tatcaggttg catctgccgg aataacctac acagatagaa gatggtgctt    6300
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt cctattgct ggtggtgctc atacctgagc cagaaaagca     6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
tgcagtgacc acctcataca acaactactc cttaatggcg atgccacgc aagctggagt     7140
gttgtttggc atgggcaaag ggatgccatt ctacgcatgg gactttggag tcccgctgct    7200
aatgataggt tgctactcac aattaacacc cctgacccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccaagt ggagaaaaag atgggacagg tgctactcat     7440
agcagtagcg gtctccagcg ccatactgtc gcggaccgcc tggggtggg gggaggctgg     7500
ggctctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860
ggtggagcgg ggatacctgc agccctatgg aaaggtcatt gatcttggat gtggcagagg    7920
gggctggagt tactacgtcg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgttgctgtg    8100
```

```
tgacataggt gagtcatcat ctagtcctga agtggaagaa gcacggacgc tcagagtcct    8160
ctccatggtg ggggattggc ttgaaaaaag accaggagcc ttttgtataa aagtgttgtg    8220
cccatacacc agcactatga tggaaaccct ggagcgactg cagcgtaggt atggggagg     8280
actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga aatatgagga ggatgtgaat ctcggctctg cacgcgggc    8460
tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taaacggggt    8640
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760
agacccccaa gaaggcactc gtcaggttat gagcatggtc tcttcctggt tgtggaaaga    8820
gctaggcaaa cacaaacggc cacgagtctg caccaaagaa gagttcatca acaaggttcg    8880
tagcaatgca gcattagggg caatatttga gaggaaaaa gagtggaaga ctgcagtgga    8940
agctgtgaac gatccaaggt tctgggctct agtggacaag aaagagagc accacctgag    9000
aggagagtgc cagagctgtg tgtacaacat gatgggaaaa agagaaaaga aacaagggga    9060
atttggaaag gccaagggca gccgcgccat ctggtatatg tggctagggg ctagatttct    9120
agagttcgaa gcccttggat tcttgaacga ggatcactgg atggggagag agaactcagg    9180
aggtggtgtt gaagggctgg gattacaaag actcggatat gtcctagaag atgagtcg     9240
tataccagga ggaaggatgt atgcagatga cactgctggc tgggacaccc gcattagcag    9300
gttgatctg gagaatgaag ctctaatcac caaccaaatg gagaaaggc acagggcctt     9360
ggcattggcc ataatcaagt acacatacca aaacaaagtg gtaaaggtcc ttagaccagc    9420
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960
gctcctttat ttccacagaa gggacctccg actgatggcc aatgccattt gttcatctgt    10020
gccagttgac tgggttccaa ctgggagaac tacctggtca atccatggaa agggagaatg    10080
gatgaccact gaagacatgc ttgtggtgtg aacagagtg tggattgagg agaacgacca     10140
catggaagac aagaccccag ttacgaaatg gacagacatt ccctatttgg gaaaaaggga    10200
agacttgtgg tgtggatctc tcataggca cagaccgcgc accacctggg ctgagaacat    10260
taaaaacaca gtcaacatgg tgcgcaggat cataggtgat gaagaaaagt acatggacta    10320
cctatccacc caagttcgct acttgggtga agaagggtct acacctgag tgctgtaagc    10380
accaatctta atgttgtcag gcctgctagt cagccacagc ttggggaaag ctgtgcagcc    10440
tgtgaccccc ccaggagaag ctgggaaacc aagcctatag tcaggccgag aacgccatgg    10500
```

```
cacggaagaa gccatgctgc ctgtgagccc ctcagaggac actgagtcaa aaaaccccac   10560
gcgcttggag gcgcaggatg ggaaaagaag gtggcgacct tccccaccct tcaatctggg   10620
gcctgaactg gagatcagct gtggatctcc agaagaggga ctagtggtta gagga        10675

<210> SEQ ID NO 7
<211> LENGTH: 149
<212> TYPE: DNA
<213> ORGANISM: Vibrio cholera

<400> SEQUENCE: 7
gtgattgaca gagctttgag agttttactg gccgtcaaat ttggttctcg acccgctgtc      60
accaattacg ctgcttttc cttttatta actcctatac ttgtgtacgc ccaaagccag      120
attgttttgg gcgttttttt atctggttt                                        149
```

What is claimed is:

1. A method of controlling Zika virus in a mosquito comprising the Zika virus, the method comprising the steps of:
   introducing into the mosquito a genetically modified bacteria that colonizes the mosquito, wherein the bacteria comprises an expression control sequence operably linked to a nucleotide sequence encoding a heterologous double stranded RNA (dsRNA) polynucleotide that inhibits expression of an essential gene of the Zika virus; wherein the dsRNA polynucleotide is selected from one of the nucleotide sequences of SEQ ID NO:s. 1, 2, 3, 4 and 5; and
   wherein expression of the dsRNA polynucleotide within the mosquito inhibits expression of the essential gene expression of the Zika virus.

2. The method of claim 1, wherein the mosquito is: a female mosquito that transmits the Zika virus to a mammalian organism, a mosquito larvae, a third instar larva, a pupa, or an adult mosquito.

3. The method of claim 2, wherein the introducing to a mosquito the genetically modified bacteria comprises a method selected from the group consisting of: soaking, spraying, injecting, feeding, introducing to through an aerosolized disbursement, introducing to through an environmental aerosolized disbursement, introducing to through an environmental aerosolized disbursement in water sources, brushing, dressing, dripping, and coating the mosquito and wherein during the introduction the bacteria is lyophilized, freeze-dried, microencapsulated, desiccated, in an aqueous carrier or in a solution.

4. The method of claim 2, wherein the genetically modified bacteria is obtained from a bacteria selected from the group consisting of: an endosymbiotic bacteria that persists through the life-cycle of the mosquito, *Pseudomonas putida* strain Ae171, and *Pseudomonas putida* strain Ae142.

5. The method of claim 4 wherein the genetically modified endosymbiotic bacteria further expresses a heterologous nucleotide encoding a VrrA small-noncoding RNA.

6. The method of claim 1, wherein the essential pathogen gene of the Zika virus is: NS2B, NS3, or NS4.

7. A paratransgenic system for the bio-control of a Zika virus-carrying mosquito comprising the steps of:
   generating a genetically modified endosymbiotic bacteria comprising an expression control sequence operably linked to at least one heterologous nucleotide encoding at least one inhibitory RNA polynucleotide that downregulates expression of at least one Zika virus gene, and wherein the genetically modified endosymbiotic bacteria is paratransgenic with the mosquito;
   introducing into the mosquito an effective amount of the genetically modified endosymbiotic bacteria that colonizes the mosquito and expresses the at least one inhibitory RNA polynucleotide that downregulates expression of the at least one Zika virus gene; and
   wherein the at least one inhibitory RNA polynucleotide is selected from the nucleotide sequences of SEQ ID No:s 1, 2, 3, 4 and 5.

8. The method of claim 7, wherein the mosquito is: *Aedes aegypti*, *Aedes albopictus*, or *Anopheles gambiae*.

9. The method of claim 8, wherein the mosquito is: a female mosquito that transmits the Zika virus to a mammalian organism; a mosquito larvae, a third instar larva, a pupa, or an adult mosquito.

10. The method of claim 9, wherein the introducing to the mosquito an effective amount of the genetically modified endosymbiotic bacteria comprises a method selected from the group consisting of: administering an effective amount of the genetically modified endosymbiotic bacteria through one or more of the following methods selected from the groups consisting of: soaking, spraying, injecting, feeding, introducing to through an aerosolized disbursement, introducing to through an environmental aerosolized disbursement, introducing to through an environmental aerosolized disbursement in water sources, brushing, dressing, dripping, and coating the mosquito and wherein during the introduction the bacteria is lyophilized, freeze-dried, microencapsulated, desiccated, in an aqueous carrier or in a solution.

11. The method of claim 7 wherein the genetically modified endosymbiotic bacteria is obtained from: *E. coli* strain JC8031, an autotropic endosymbiotic enteric bacteria, an RNase III deficient endosymbiotic enteric bacteria, *E. coli* strain HT115, *E. coli* strain HT27, *E. coli* strain JC8031, *Pantoea* strain Ae16, *Serratia* strain AeS1, *Serratia* strain MS5, *Pseudomonas putida* strain Ae076, or *Pseudomonas putida* Ae171.

12. The method of claim 11, wherein said at least one inhibitory RNA polynucleotide is a dsRNA polynucleotide molecule.

13. The method of claim 12, wherein the endosymbiotic bacteria further expresses a heterologous nucleotide encoding a VrrA small-non-coding RNA.

14. The method of claim 12, wherein the at least one Zika virus gene is selected from the group consisting of: NS2B, NS3, and NS4.

* * * * *

UNITED STATES PATENT AND TRADEMARK OFFICE
CERTIFICATE OF CORRECTION

PATENT NO. : 10,294,475 B2
APPLICATION NO. : 15/922904
DATED : May 21, 2019
INVENTOR(S) : Sayre et al.

It is certified that error appears in the above-identified patent and that said Letters Patent is hereby corrected as shown below:

On the Title Page

Item (72), Please add the following Inventors:

Bradley R. Borlee
Fort Collins, CO (US)

Rebekah Kading
Fort Collins, CO (US)

William Black
Fort Collins, CO (US)

Kenneth Olson
Fort Collins, CO (US)

Carol Blair
Fort Collins, CO (US)

Signed and Sealed this
Thirteenth Day of December, 2022

Katherine Kelly Vidal
*Director of the United States Patent and Trademark Office*